United States Patent
Nielsen et al.

(10) Patent No.: US 10,544,414 B2
(45) Date of Patent: Jan. 28, 2020

(54) TWO-CASSETTE REPORTER SYSTEM FOR ASSESSING TARGET GENE TRANSLATION AND TARGET GENE PRODUCT INCLUSION BODY FORMATION

(71) Applicant: Danmarks Tekniske Universitet, Kgs. Lyngby (DK)

(72) Inventors: Alex Toftgaard Nielsen, Kgs. Lyngby (DK); Ariane Zutz, Freigericht (DE); Rebecca Lennen, Holte (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 15 days.

(21) Appl. No.: 15/521,195

(22) PCT Filed: Oct. 22, 2015

(86) PCT No.: PCT/EP2015/074513
§ 371 (c)(1),
(2) Date: Apr. 21, 2017

(87) PCT Pub. No.: WO2016/062819
PCT Pub. Date: Apr. 28, 2016

(65) Prior Publication Data
US 2017/0355983 A1    Dec. 14, 2017

(30) Foreign Application Priority Data
Oct. 22, 2014  (EP) .................................. 14189892

(51) Int. Cl.
*C12N 15/10* (2006.01)
*C12Q 1/6897* (2018.01)
*C12N 15/70* (2006.01)
*G01N 33/50* (2006.01)

(52) U.S. Cl.
CPC ....... *C12N 15/1086* (2013.01); *C12Q 1/6897* (2013.01); *G01N 33/5023* (2013.01)

(58) Field of Classification Search
None
See application file for complete search history.

(56) References Cited

U.S. PATENT DOCUMENTS

2003/0119094 A1  6/2003  Lesley et al.
2004/0078148 A1  4/2004  Waldo

FOREIGN PATENT DOCUMENTS

WO    WO-2002061041    8/2002

OTHER PUBLICATIONS

Ulloa-Aguirre, A. et al., Pharmacoperones: A New Therapeutic Approach for Diseases Caused by Misfolded G Protein-Coupled Receptors; Recent Pat EndocrMetab Immune Drug Discov., 5(1): 13-24, Jan. 2011.
Andersen, J. et al., New Unstable Variants of Green Fluorescent Protein for Studies of Transient Gene Expression in Bacteria, Applied and Environmental Microbiology, 64(6): 2240-2246, 1998.
Butt, T. et al., SUMO Fusion Technology for Difficult-to-Express Proteins. Protein Expression and Purification, 43(1): 1-9, 2005.
Mendez-Perez, D. et al., A Translating-coupling DNA cassette for monitoring protein translation in *Escherichia coli*, Metabolic Engineering; 14(4): 298-305, 2012.
Davis, G. et al., New Fusion Protein Systems Designed to Give Soluble Expression in *Escherichia coli*. Biotechnology and Bioengineering. 65(4): 382-388, 1999.
Gregersen, N. et al., Protein misfolding, aggregation, and degradation in disease. Mol Biotechnol, 31(2):141-50, 2005.
Marblestone, J. et al., Comparison of SUMO Fusion Technology with Traditional Gene Fusion Systems: Enhanced Expression and Solubility with SUMO, Protein Science: a Publication of the Protein Society, 15(1): 182-89, doi:10.1110/ps.051812706, Jan. 2006.
Kraft, M. et al., An online monitoring system based on a synthetic sigma32-dependent tandem promoter for visualization of insoluble proteins in the cytopiasm of *Escherichia coli*, Applied Microbiology and Biotechnology, 75(2): 397-406, 2007.
Dyson, M. et al., Production of Soluble Mammalian Proteins in *Escherichia coli*: Identification of Protein Features That Correlate with Successful Expression, BMC Biotechnology 4, 32, doi:10.1186/1472-6750-4-32, Dec. 14, 2004.
Conn, M. et al., Pharmacoperone identification for therapeutic rescue of misfolded mutant proteins, Frontiers in Endocrinology, 2(6):1-7, 2011.
Ramon, A, et al., Inclusion bodies: not that bad . . . , Front Microbiol, 5(56): 1-6, 2014.
Mattoo, R., Molecular Chaperones are Nanomachines That Catalytically Unfold Misfolded and Alternatively Folded Proteins, Cellular and Molecular Life Sciences: CMLS 71(17): 3311-25, doi:10.1007/s00018-014-1627-y, Sep. 2014.
Vincentelli, R. et al., Automated Expression and Solubility Screening of His-Tagged Proteins in 96-Well Format, Analytical Biochemistry, 346(1): 77-84, oi:10.1016/j.ab.2005.07.039. Nov. 1, 2005.
Rudolph, In vitro folding of inclusion body proteins, The FASEB Journal, 10: 49-56, 1996.
Lesley, S. et al., Gene expression response to misfolded protein as a screen for soluble recombinant protein, Protein Engineering, 15(2), 153-60, 2002.
Shaner et al., A guide to choosing fluorescent proteins, Nature Methods, 2(12): 905-909, Dec. 2005.
Singh, A. et al., Solubilization and refolding of inclusion body proteins, Methods Mol Biol., 1258:283-91. doi: 10.1007/978-1-4939-2205-5_15. Review, 2015.

(Continued)

*Primary Examiner* — Channing S Mahatan
(74) *Attorney, Agent, or Firm* — Julie K. Staple; Dinsmore & Shohl LLP

(57) ABSTRACT

The present invention relates to a dual cassette reporter system capable of assessing target gene translation and target gene product folding. The present invention further relates to vectors and host cells comprising the dual cassette reporter system. In addition the invention relates to the use of the dual cassette reporter system for assessing target gene translation and target gene product folding.

19 Claims, 16 Drawing Sheets

Specification includes a Sequence Listing.

(56) References Cited

OTHER PUBLICATIONS

Schultz, T. et al., The evaluation of the factors that cause aggregation during recombinant expression in *E. coli* is simplified by the employment of an aggregation-sensitive reporter, Microbial Cell Factories, 5:28, 2006.

Shih, Y. et al., High-Throughput Screening of Soluble Recombinant Proteins, Protein Science : a Publication of the Protein Society, 11(7): 1714-19, doi:10.1110/ps.0205202, Jul. 2002.

Wang, Z. et al., Coupled Selection of Protein Solubility in *E. coli* Using Uroporphyrinogen III Methyltransferase as Red Fluorescent Reporter, Journal of Biotechnology, 186: 169-74, doi:10.1016/j.jbiotec.2014.06.025, Jul. 3, 2014.

TWO-CASSETTE REPORTER SYSTEM FOR ASSESSING TARGET GENE TRANSLATION AND TARGET GENE PRODUCT INCLUSION BODY FORMATION

FIELD OF INVENTION

The present invention relates to the field of single cell genetic reporters, in particular to reporters comprising two cassettes, wherein the first cassette is configured to yield a reporter gene mediated signal upon full translation of a target gene, and a second cassette is configured to yield a reporter gene mediated signal in presence of target gene product inclusion bodies.

BACKGROUND OF INVENTION

Expression of heterologous proteins in microbial production organisms can be a challenging process that often requires significant optimization due to misfolding of the proteins. Heterologous proteins are required for a number of processes, including for example metabolic pathway engineering, production of proteins for structure determination as well as biocatalytic processes. In metabolic pathway engineering for production of biochemicals, it is often required to functionally express a larger number of different enzymes. If one individual enzyme of the metabolic pathway is not correctly expressed or folded, the entire process will typically not be working optimally. There is also a very large market for heterologous proteins and peptides produced from microorganisms. Such peptides dependent on correct folding either directly in the production organism or during the subsequent post processing steps. Optimizing the translation, folding and stability of such target proteins is therefore of significant importance.

Although proteins can typically fold by themselves, most organisms have evolved mechanisms for controlling and aiding the process. Molecular chaperones typically assist in protein folding, and they can prevent polypeptide chains from aggregating before the correct protein folding has been achieved. Chaperones can either actively participate in protein folding using an energy dependent mechanism, or they can passively bind peptide chains, thereby preventing unwanted protein aggregation (Rayees et al 2014). Most molecular chaperones fall into a few conserved protein families, including Hsp100s (ClpB), Hsp90s (HtpG), Hsp70/Hsp110 (DnaK), Hsp60/CCTs (GroEL), as well as small heat shock proteins (IbpA/B). The chaperones bind to hydrophobic residues that are abnormally exposed to the cytosolic environment, and are thus prone to associate and form stable inactive aggregates. Chaperones are typically induced during stress conditions, and the proteins are often referred to heat shock proteins (Hsp). Expression of chaperones may differ from organism to organism, and this may contribute to the lack of predictability of folding of heterologously expressed proteins.

Several strategies for improving folding and expression of heterologous proteins are known. These include the use of protein expression and solubility tags, which are either short peptide or protein tags fused to the N-terminus of proteins. Those tags are supposed to function as folding scaffolds thereby helping to increase translation and folding of proteins with poor folding properties (Marblestone et al. 2006). Another strategy for improving protein folding includes the truncation of unstructured hydrophobic parts of the protein (Dyson et al. 2004).

A more efficient way to optimize protein expression would be to screen large random mutant libraries for variants of the enzymes with improved folding. However, generation of random mutant libraries often results in frequent generation of either frame shift mutations or stop codons. When screening for mutants with improved folding, it is therefore necessary to exclude the large number of clones that no longer express the target protein.

Current methods for analyzing protein expression and folding often focus on extraction of protein from the production organism, separating the protein into soluble (folded) and insoluble fractions, and analyzing these fractions using SDS-PAGE, dot blot based technologies, or by fusion of the target proteins to markers (Shih et al. 2002, Vincentelli et al. 2005, Wang et al. 2014). These are often time-consuming processes that are not amenable to screening of larger libraries of production organisms or protein variants at the single cell level. Other methods require the addition of large protein tags that may affect protein folding. For this reason, there is a need for a high throughput method that enables screening for protein folding and also protein translation at the single cell level.

Such a method would require either direct selection of bacterial growth based on for example antibiotics resistance or the possibility of sorting the production organisms based on the expression of for example a fluorescent marker.

SUMMARY OF INVENTION

Protein translation level and the degree of protein misfolding are key components in heterologous protein production. The current technologies are ineffective for assessment of both the protein translation level and the degree of protein misfolding in high-throughput screening methods at the single cell level. The present inventors have solved the challenge of monitoring both protein translation and protein folding in the same cell by a dual reporter system which enables simultaneous assessment of these two important parameters at the single cell level. The present inventors have demonstrated a functional dual reporter system that enables single cell monitoring of both protein translation level and the degree of protein misfolding. The system of the present invention may be used to analyze if heterologously expressed proteins are correctly folded while being fully translated. The system can be used to screen large libraries of proteins for their degree of protein folding. Such mutant variants may include truncation libraries as well as random mutation libraries. The present inventors have demonstrated how the system can be combined with fluorescence activated cell sorting and next generation sequencing for a protein wide identification of mutations important for correct protein translation and folding. In addition the present inventors have demonstrated high throughput screening of various protein solubility tags and their effect on heterologous protein expression and folding.

Thus in a main aspect the present invention concerns a single cell two-cassette reporter system comprising:
  a) a first cassette comprising
    i) a target gene or a target gene cloning site configured for inserting the target gene;
    ii) a first reporter gene or a first reporter gene cloning site configured for inserting a first reporter gene therein, wherein translation of the first reporter gene inserted in the first reporter gene cloning site is translationally linked to the target gene;

b) a second cassette comprising
  i) a protein inclusion body responsive promoter operably linked to a second reporter gene or reporter gene cloning site configured for inserting a second reporter gene therein.

In another aspect the present invention concerns a vector comprising the system as described herein above.

In a further aspect the present invention concerns a host cell comprising the system as described herein above, or the vector as described herein above.

In another aspect the present invention concerns a method of assessing target gene translation and/or target gene product solubility, the method comprising the steps of:
  a) providing the two-cassette reporter system as described in the present invention comprising
    i) a target gene, and
    ii) a first reporter gene, and
    iii) a second reporter gene, and
  b) expressing the two-cassette reporter system in a host cell as described in the present invention, and
  c) assessing the target gene translation and/or target gene product solubility using analysis means as described in the present invention, by comparison to appropriate control host cells.

In another aspect the present invention concerns a kit of parts comprising a) a two-cassette reporter system as described herein, and b) instructions on how to use the two-cassette reporter system.

A further aspect of the present invention concerns a method of assessing the effect of host cell growth conditions on the target gene translation and/or target gene product solubility, comprising the steps of:
  a) providing the two-cassette reporter system described in the present invention comprising
    i) a target gene, and
    ii) a first reporter gene, and
    iii) a second reporter gene, and
  b) expressing the two-cassette reporter system in a host cell described in the present invention under various growth conditions, and
  c) assessing the gene translation and/or target gene product solubility using analysis means described in the present invention, by comparison to appropriate control host cells.

Yet another aspect of the present invention concerns to a method of developing a target gene translation and target gene product solubility prediction algorithm, comprising the steps of:
  a) providing a target gene library comprising a plurality of vectors comprising the system described in the present invention comprising
    i) a target gene, and
    ii) a first reporter gene, and
    iii) a second reporter gene, and
  b) expressing the target gene library in a plurality of host cells described in the present invention, and
  c) assessing the target gene translation and/or target gene product solubility of the host cells using analysis means as described in the present invention by comparison to appropriate control host cells, and
  d) obtaining the polynucleotide sequence of the target gene of the assessed host cells, and
  e) developing a target gene translation and target gene product solubility prediction algorithm.

Yet an aspect of the present invention concerns a protein folding prediction algorithm developed using the method as described herein above or the system as described herein above.

In another aspect the present invention concerns an inclusion body responsive reporter system comprising
  a) a target gene or a target gene cloning site configured for inserting the target gene as described in the present invention; and
  b) a protein inclusion body responsive promoter operably linked to a second reporter gene or second reporter gene cloning site as described in the present invention, wherein the second reporter encodes a second protein capable of generating a second signal.

Another aspect of the present invention concerns a host cell as described in the present invention comprising the inclusion body responsive reporter system as described in the present invention.

A further aspect of the present invention concerns a method of assessing target gene product solubility, the method comprising the steps of:
  a) providing the reporter system as described in the present invention comprising
    i) a target gene as described in the present invention, and
    ii) a second reporter gene encoding a protein as described in the present invention, and
  b) expressing the inclusion body responsive reporter system in a host cell described in the present invention, and
  c) assessing the target gene product solubility using analysis means as described in the present invention, by comparison to appropriate control host cells.

Another aspect of the present invention concerns a kit of parts comprising
  a) an inclusion body responsive reporter system as described herein above, and
  b) instructions on how to use the reporter system.

Yet an aspect of the present invention concerns a method of assessing the effect of host cell growth conditions on the target gene product solubility, comprising the steps of:
  a) providing the inclusion body responsive reporter system as described in the present invention comprising
    i) a target gene described in the present invention, and
    ii) a second reporter gene encoding a second reporter protein capable of generating a second signal described in the present invention, and
  b) expressing inclusion body responsive reporter system in a host cell described in the present invention under various growth conditions, and
  c) assessing the target gene product solubility using analysis means described in the present invention, by comparison to appropriate control host cells.

Another aspect of the present invention concerns a method of developing a target gene product solubility prediction algorithm, comprising the steps of:
  a) providing a target gene library comprising a plurality of vectors comprising the inclusion body responsive reporter system described in the present invention each vector comprising
    i) a target gene described in the present invention, and
    ii) a second reporter gene encoding a second reporter protein capable of generating a second signal described in the present invention, and
  b) expressing the target gene library in a plurality of host cells described in the present invention, and c) assessing the target gene product solubility of the host cells using analysis described in the present invention, by comparison to appropriate control host cells, and d) obtaining the polynucleotide sequence of the target gene of the assessed host cells as described in the present invention, and e) developing a target gene product solubility prediction algorithm as described in the present invention.

Yet an aspect of the present invention concerns a protein folding prediction algorithm developed using the method of developing a target gene product solubility prediction algorithm described herein above or the inclusion body responsive reporter system described in the present invention.

In another aspect is disclosed herein a method for screening pharmacoperones comprising the steps of:

a) providing a host cell expressing a system as described herein above, said system comprising
  i. a target gene described herein above encoding a protein, and
  ii. a second reporter gene comprising a gene encoding a second reporter protein, capable of generating a second signal, and
  iii. optionally, a first reporter gene comprising a gene encoding a first reporter protein, capable of generating a first signal, and b) providing a plurality of molecules to be screened for pharmacoperone activity, c) contacting said host cell with said plurality of molecules, d) analysing the second and optionally the first signal, and optionally sorting the cells based on the second and optionally the first signal, thereby determining which molecules can restore proper folding of the protein.

In yet another aspect is disclosed herein a method for identifying residues important for correct folding of a protein, said method comprising the steps of:

a) providing a target gene library comprising a plurality of vectors comprising the system described herein above, each comprising
  i. a target gene described herein above encoding said protein, and
  ii. a second reporter gene comprising a gene encoding a second reporter protein, capable of generating a second signal, and
  iii. optionally, a first reporter gene comprising a gene encoding a first reporter protein, capable of generating a first signal, and b) expressing the target gene library in a plurality of host cells described herein above, and c) sorting the cells into at least two populations on the basis of the second and optionally of the first signal, d) isolating the vectors comprised in the cells of the sorted populations, and e) identifying the sequence of the target genes comprised within said isolated vectors, f) comparing the sequences of the target genes of the two sorted populations, thereby identifying the sites in said sequences which differ in the two sorted populations.

Figure 1:
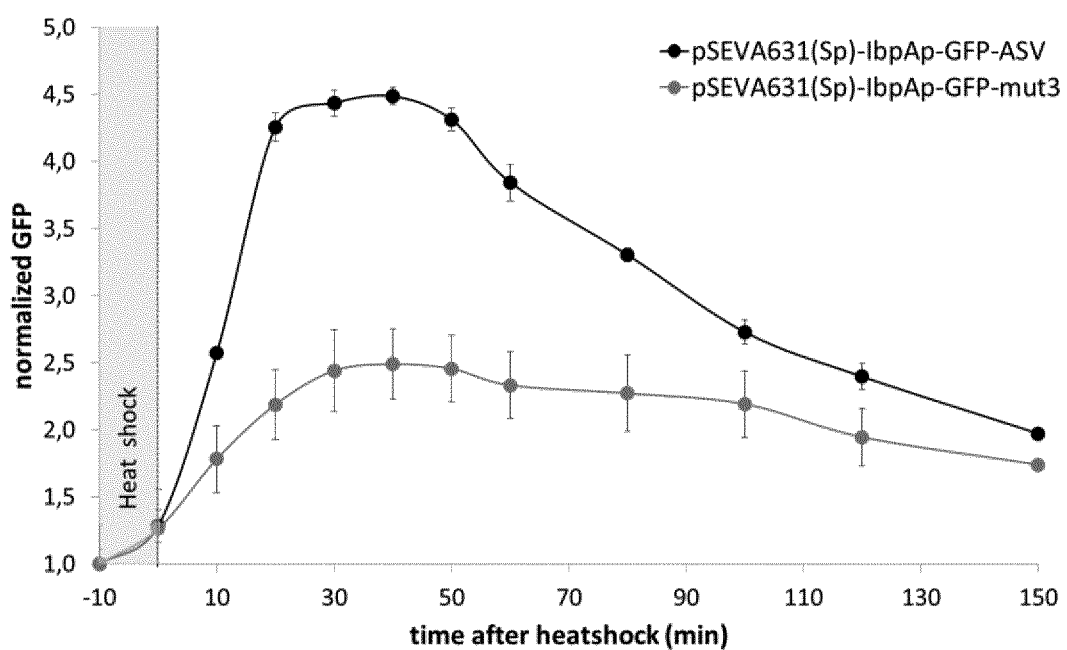
FIG. 1: Monitoring heat shock-induced inclusion body formation

Time-dependent stimulation of the IbpAp-GFP-ASV (dark grey) and the IbpAp-GFP-mut3 (light grey) reporter genes by heat shock-induced inclusion body formation. The induction of the IbpA promoter is monitored by changes in the GFP signal using flow cytometry. The GFP signals (FITC-A, X-mean) are normalized to the respective background signal at each time-point. Each measurement was performed in triplicates (average±SD).

FIG. 2: Dual sensor system for monitoring recombinant protein expression and folding in E. coli The activation of the protein translation (A) and protein folding (B) sensor by over-expression of recombinant proteins in Rosetta2(DE3)pLysS is analyzed 1 hour after induction with IPTG at 30° C. The mCherry (PE-Texas Red-A) and the GFP (FITC-A) signals are monitored by flow cytometry and X-mean values are normalized to the respective PARP1-BRCT signal. Each experiment was performed with n≥5 (average±SD). The subcellular localization of recombinant proteins is shown in C. The total fraction (total), including soluble and insoluble proteins, and the soluble protein fraction (sol) are analyzed by SDS-PAGE and subsequent InstantBlue staining (RunBlue 4-20%, upper panel) and immunoblotting (NuPAGE® Bis-Tris gel 4-12%, anti-His antibody, lower panel). For Instant blue staining samples were analyzed 3 hours and for immunoblotting 1 hour after induction at 30° C.

FIG. 3: Impact of the plasmid backbone on the sensitivity of the protein folding sensor Folding of BRCA1-BRCT and PARP1-BRCT was analyzed using pSEVA631(Sp)-IbpAp-GFP-ASV (dark grey bars) or pSEVA441-IbpAp-GFP-ASV (light grey bars) as a protein folding sensor. Cells transformed with an empty pET22b vector were used for determination of the background GFP signal. The stimulation of the protein folding sensors by over-expression of the recombinant proteins is analyzed 1 hour after induction with IPTG at 30° C. GFP signal was monitored by flow cytometry and X-mean values (FITC-A) are normalized to the respective PARP1-BRCT signal. Each experiment was done in triplicates (average±SD).

FIG. 4: High-throughput screening and next generation sequencing of protein mutant libraries (A) Fluorescence-activated cell sorting (FACS) histogram plot for with pET22b (light grey) and PARP1-BRCT (dark grey) transformed Rosetta2(DE3)pLysS cells harboring the protein folding sensor pSEVA631(Sp)-IbpAp-GFP-ASV. Sorting gate1 (left panel) defines the cell population with a mCherry (PE-Texas Red-A) signal higher than the pET22b background signal. Sub-gate 2 (right panel) includes all cells with a GFP signal (FITC-A) above background. (B) The histogram plots for cells expressing PARP1-BRCT (dark grey) and the PARP1-BRCT mutant library (light grey) in presence of the protein folding sensor. Cells included in gate1 (left panel; mCherry) as well as gate 2 (right panel; GFP) were sorted and further characterized. (C) Histogram plots of PARP1-BRCT (dark grey) and the sorted PARP1-BRCT-library (light grey) 1 hour (left panel) and 2.5 hours (right panel) after induction of protein expression at 30° C. (D) Subcellular localization of PARP1-BRCT (dark grey) and the sorted PARP1-BRCT-library 1 hour after induction of protein expression. The total fraction (total), including soluble and insoluble proteins, the soluble protein fraction (sol), and the inclusion body fraction (IB) were analyzed by SDS-PAGE (Run Blue 4-20%) and immunoblotting using an anti-His antibody. (E) and (F) Next generation sequencing analysis of the sorted PARP1-BRCT-library. The bar graph provides an overview of amino acids that are enriched or deprived at each individual position in the sorted fraction of the protein library.

FIG. 5: Improving the folding properties of proteins by random mutagenesis

Rosetta2(DE3)pLysS cells were co-transformed with the protein folding sensor (pSEVA631(Sp)-IbpAp-GFP-ASV) and with pET22-BRCA1-BRCT-trans-mCherry, pET22-BRCA1-BRCT-Stop-trans-mCherry, pET22-BRCA1-BRCT mutant library 1 or pET22-BRCA1-BRCT mutant library 2. 1 hour after induction of protein expression at 30° C. cells were analyzed and sorted by FACS. (A) FACS histogram plot of BRCA1-BRCT expressing cells. Sorting gate1 defines the cell population with a GFP signal (FITC-A) that is lower than the signal observed after expression of BRCA1-BRCT. Histogram plots of cells expressing BRCA1-BRCT library 1 (B) and BRCA1-BRCT library 2 (C), respectively. Cells exhibiting a GFP-signal lower than BRCA1-BRCT-trans-mCherry control (gate1, defined in A) were sorted. The mCherry signal (PE-Texas red-A) of the sorted cell population is shown in the respective right panel (B & C). (D) FACS histrogram plots of BRCA1-BRCT-trans-mCherry (dark grey) and BRCA1-BRCT-Stop-trans-mCherry (light grey). Gate1 (left panel) defines the cell population with a mCherry (PE-Texas red-A) signal higher than BRCA1-BRCT-Stop-trans-mCherry background signal. Sub-gate 2 (right panel) includes all cells with a GFP signal (FITC-A) that is lower than the signal observed after expression of BRCA1-BRCT. FACS histogram plots (PE-Texas Red-A, left panel; FITC-A, middle panel) of cells expressing library 1 (E) and library 2 (F), respectively. The two gates for mCherry and GFP that are defined in (D) were used for sorting. The mCherry signal (PE-Texas Red-A) of the sorted cell population is shown in the respective right panel (E & F). (G) Translation and folding of sorted BRCA1-BRCT mutants (single mutants) is analyzed after sorting (E & F). Cells co-transformed with pSEVA631(Sp)-IbpAp-GFP-ASV and pET22, pET22-BRCA1-BRCT-trans-mCherry or pET22-BRCA-BRCT-Stop-trans-mCherry, were used as control (control experiments were performed in triplicates (average±SD)). Protein translation and activation of the folding sensor was analyzed by flow cytometry 1 hour after induction with IPTG at 30° C. The mCherry (PE-Texas Red-A) and the GFP (FITC-A) signals were monitored by flow cytometry and X-mean values were normalized to the BRCA1-BRCT signal.

Figure 6A:
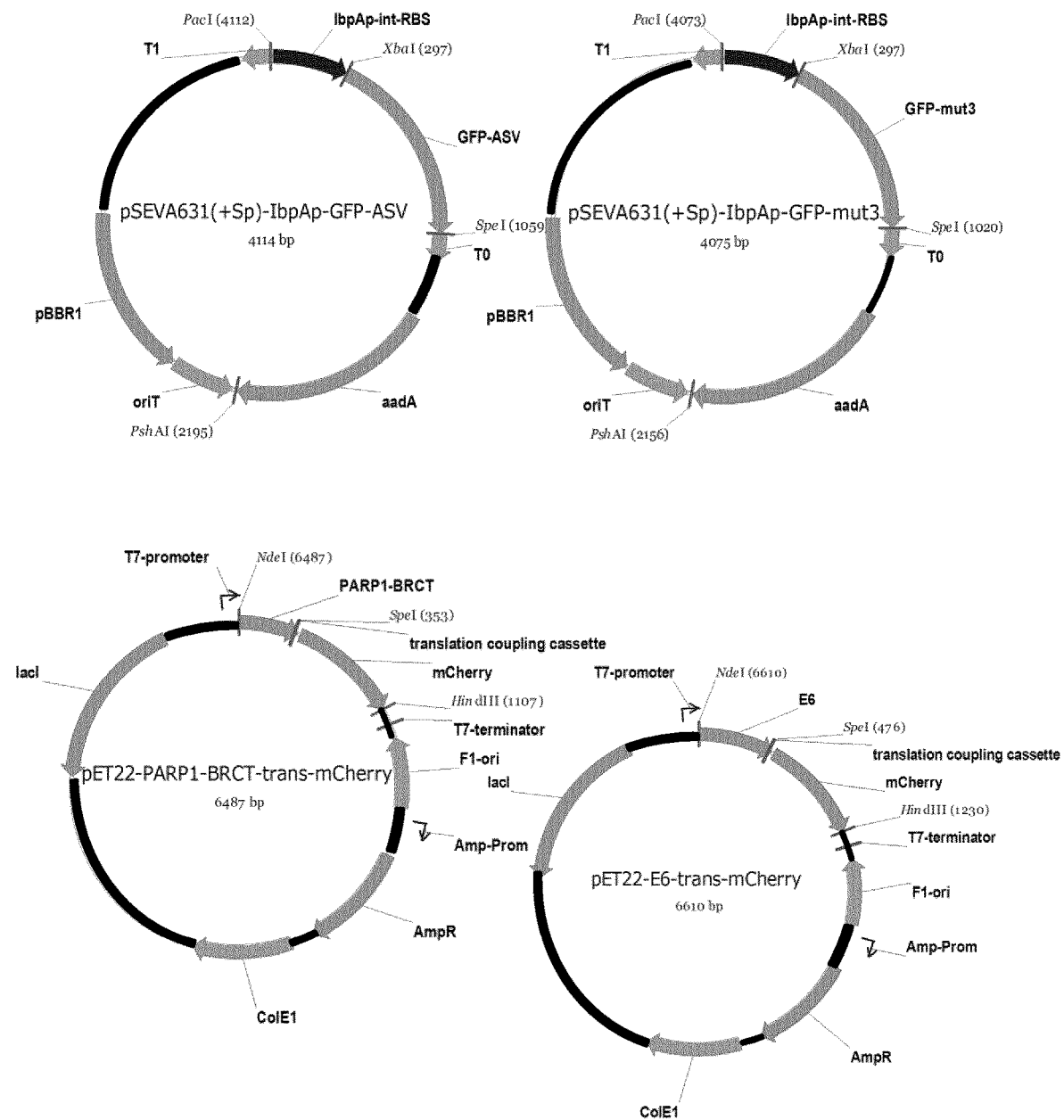
Figure 6B:
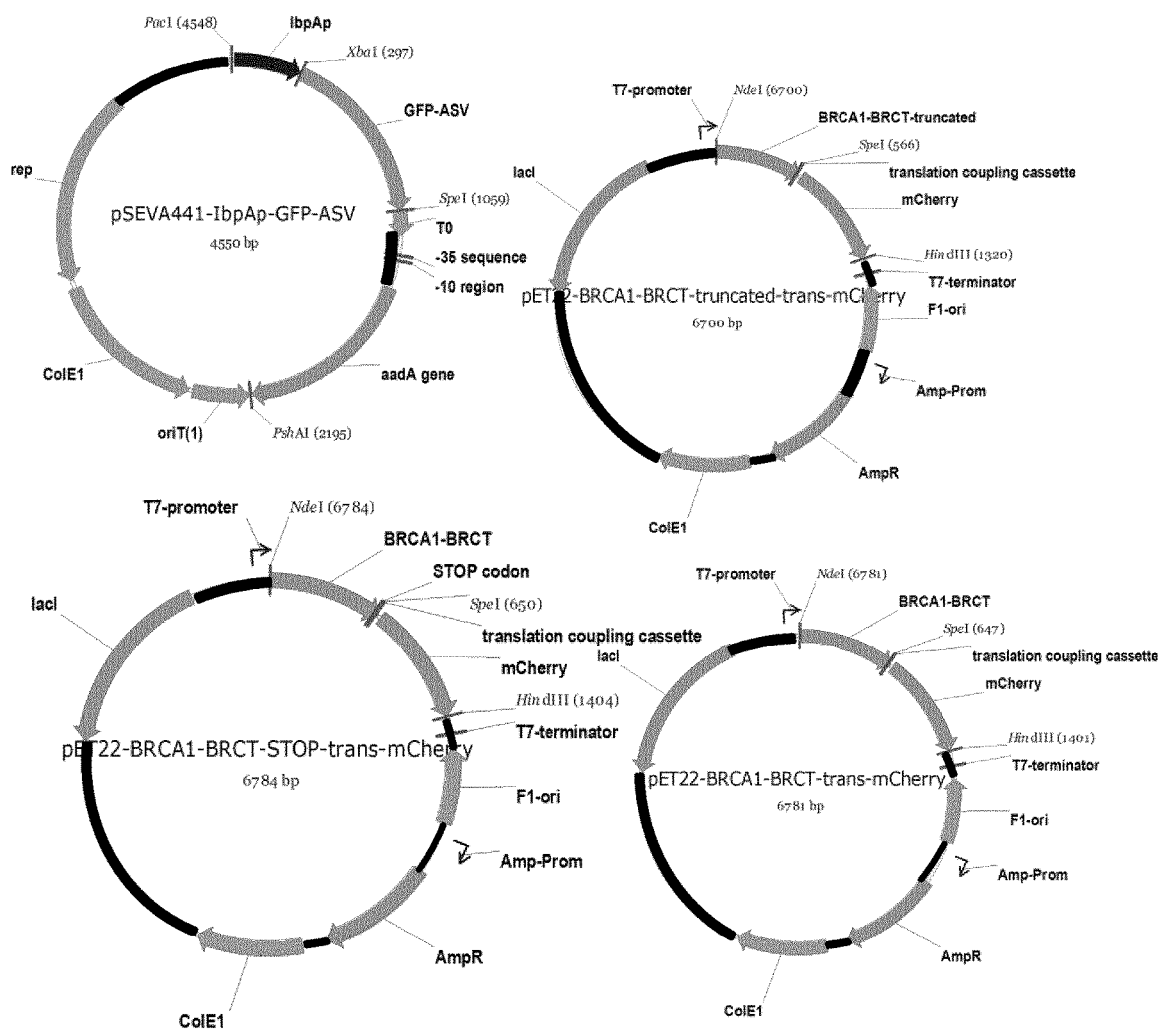
Figure 6C:
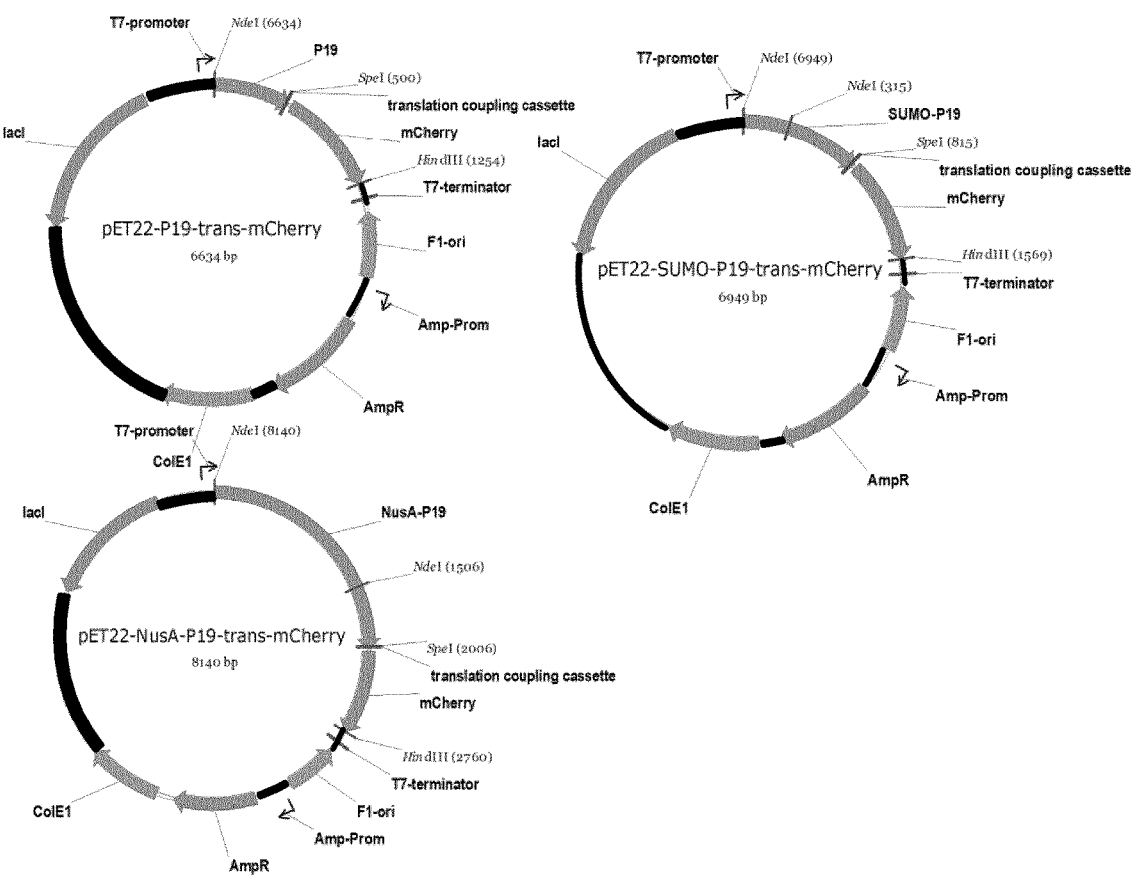

FIG. 6: Plasmid maps. An overview of the plasmids used to test the reporter of the present invention.

Figure 7:
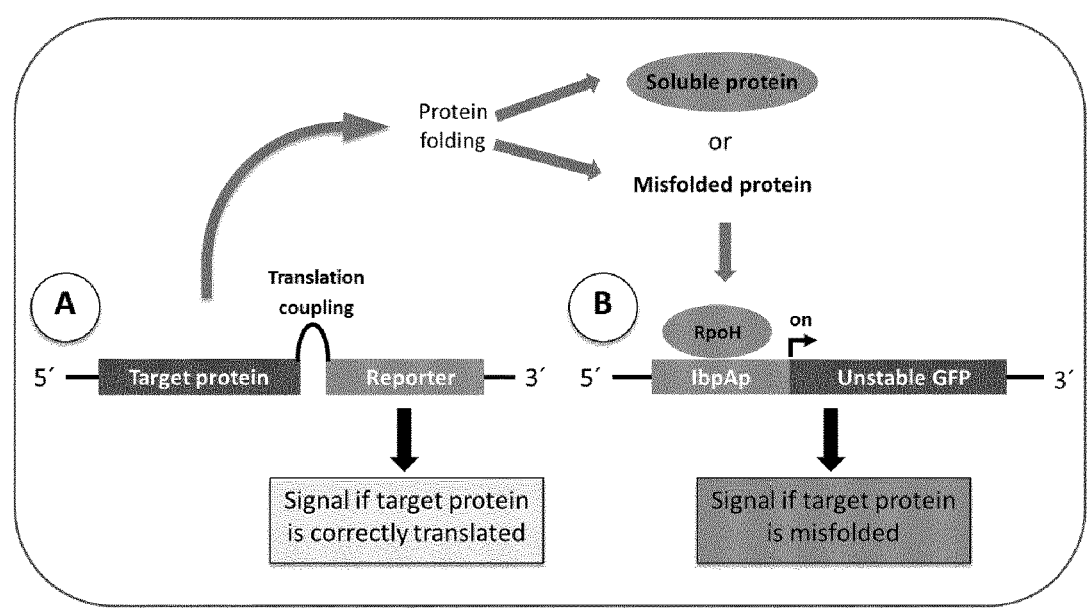

FIG. 7: Schematic overview of the dual sensor system. (A) The translation coupling sensor is comprised of a target protein, a translation coupling cassette and a reporter gene. If the target protein is fully translated, the reporter gene is expressed, resulting in for example a signal. After translation, the target protein may either be proper folded, which typically results in soluble protein, or it can be misfolded. As a consequence of misfolding, the protein aggregates and accumulates in inclusion bodies. (B) Inclusion body formation increases the level of free RpoH (heat shock sigma-factor sigma32), which binds to RpoH inducible promoter, such as the IbpAp promoter, which activates the expression of an unstable GFP, resulting in a green fluorescent signal. The combined system allows simultaneous monitoring of both protein translation and protein folding at the single cell level.

DETAILED DESCRIPTION OF THE INVENTION

As outlined above protein translation level and the degree of protein misfolding are key parameters in heterologous protein production. The current technologies are ineffective for assessment of both parameters in high-throughput screening methods at the single cell level. The present inventors have solved the challenged of monitoring both protein translation and protein folding at the single cell level by a dual reporter system which enables single cell monitoring these two important parameters simultaneously.

Definitions

The term "mutagenesis" as used herein refers to a process by which the genetic information of an organism is changed in a stable manner, resulting in a mutation. The genetic information may be modified, either naturally or artificially, by a number of physical, chemical and biological agents, resulting in mutations. In addition several random and targeted approaches for changing the genetic information exist. Common molecular biology methods exist for generating mutant gene libraries or targeted mutations.

The term "random protein tag" as used herein refers to an peptide and/or polypeptide tag wherein the polypeptide sequence may be any peptide and/or polypeptide sequence. Random peptide tags are often the gene product encoded by a random polynucleotide sequence.

The term "protein" as used herein refers to a polynucleotide sequence. The term protein may be used interchangeably for peptide. A protein tag may therefore also refer to a peptide tag. Likewise a peptide tag may as well refer to a protein tag.

The term "folding" as used herein refers to protein folding and the process by which a protein structure assumes its functional shape or conformation. It is the physical process by which a polypeptide folds into its characteristic and functional three-dimensional structure from random coil.

The term "inclusion body or inclusion bodies" as used herein refers to dense electron-refractile particles of aggregated protein found in both the cytoplasmic and periplasmic spaces of heterologous hosts during high-level expression of heterologous protein. It is generally assumed that high level expression of non-native and/or highly hydrophobic protein is more prone to lead to accumulation as inclusion bodies in heterologous expression hosts. Inclusion bodies may also be referred to as protein aggregates. Inclusion bodies contain very little host protein, ribosomal components or DNA/RNA fragments. They often almost exclusively contain the over expressed protein. The inclusion bodies may therefore mainly derive from high level expression of heterologous proteins. Protein inclusion bodies may contain misfolded protein. However, correctly folded proteins may also form inclusion bodies.

The term "protein solubility" as used herein refers to the degree of inclusion body forming proteins which are insoluble compared to the fraction of soluble proteins. Protein solubility is therefore indicative of the inclusion body level which may be indicative of the degree of protein misfolding.

The term "destabilized" as used herein refers to reporter genes with decreased half-lives such as ranging from minutes to a few hours. Destabilized fluorescent proteins may be more susceptible to the action of indigenous proteases and yield a shorter half-life as described in Andersen et al. 1998. Mutagenesis of reporter proteins may yield destabilized versions with shorter half-life.

The term "operably linked" or "operatively linked" as used herein refers to two nucleic acid sequences wherein expression of the second nucleic acid sequence is dependent on the first nucleic acid sequence.

The term "plasmid copy number" as used herein refers to the number of copies of a plasmid present per chromosome in a cell.

The term "low copy number plasmid" as used herein refers to the number of plasmids/vectors per cell. The copy number of a plasmid is depending on the origin of replication (ORI) inter alia. The different ORIs regulate the replication mechanism of the plasmid. A low copy number plasmid typically yields 1-10 plasmids per chromosome in a cell.

The term "medium copy number plasmid" as used herein refers to the number of plasmids/vectors per cell. The copy number of a plasmid is depending on the origin of replication (ORI) inter alia. The different ORIs regulate the replication mechanism of the plasmid. A medium copy number plasmid typically yields 11-20 plasmids per chromosome in a cell.

The term "high copy number plasmid" as used herein refers to the number of plasmids/vectors per cell. The copy number of a plasmid is depending on the origin of replication (ORI) inter alia. The different ORIs regulate the replication mechanism of the plasmid. A high copy number plasmid typically yields more than 21 plasmids per chromosome in a cell.

The term "target gene" as used herein refers to any gene from any origin including genes which have been mutated using mutagenesis means. A target gene may be from a cDNA library or a mutated cDNA library.

The term "translationally linked" as used herein refers to the linkage of two genes, wherein the translation for the second gene (e.g the first reporter gene of the present invention) is dependent of complete translation of the first gene (e.g. the target gene of the present invention).

Single Cell Two-cassette Reporter System

The present invention concerns two reporter genes and a target gene. One example of the general concept of the single cell two-cassette reporter system of the present invention is illustrated in FIG. 7. The first reporter gene is associated with the first cassette of the single cell two-cassette reporter system described in the present invention. The first reporter gene of the present invention is translationally linked to the target gene. The translational coupling of the first reporter gene to the target gene ensures that the first reporter gene is only translated upon complete translation of the target gene. A multitude of strategies for translational coupling of two genes exist. Some examples of strategies for translational coupling of two genes are secondary structure mediated translational coupling, direct protein fusion mediated translational coupling, split-GFP based strategies, linkage by polynucleotide sequences encoding a polypeptide which induces a proteolytic action separating the fusion protein post translation and/or linkage by a polynucleotide which induces ribosomal skipping.

The target gene and the first reporter gene may be translationally linked by a first reporter gene translation control element and a secondary structure-forming sequence that reversibly forms a secondary structure that masks the first reporter gene translation control element. Full translation of the target gene triggers unfolding of the secondary structure-forming sequence, which unmasks the first reporter gene translation control element. Hence the first reporter gene is translated only if the target is fully translated. The signal of the first reporter gene indicates full translation of the target gene, and is assessed by comparison to appropriate controls. A weak signal of the first reporter gene product is indicative of no, partial and/or inefficient translation of the target gene. On the other hand a strong signal of the first reporter gene product is indicative of efficient and complete translation of the target gene. Therefore the first cassette of the single cell two-cassette reporter system may be referred to as a translation sensor. The general concept of a translation sensor is illustrated in FIG. 7a.

The second reporter gene of the second cassette of the single cell two-cassette reporter system is controlled by an inclusion body responsive promoter. The signal from the second reporter gene product is thus indicative of target gene product inclusion bodies, and is assessed by comparison to appropriate controls. Therefore the second cassette of the single cell two-cassette reporter system may be referred to as an inclusion body sensor. The general concept of a inclusion body sensor is illustrated in FIG. 7b.

In a main aspect the present invention concerns a single cell two-cassette reporter system comprising:
  a) a first cassette comprising
    i) a target gene or a target gene cloning site configured for inserting the target gene;
    ii) a first reporter gene or a first reporter gene cloning site configured for inserting a first reporter gene therein, wherein translation of the first reporter gene inserted in the first reporter gene cloning site is translationally linked to the target gene;
  b) a second cassette comprising
    i) a protein inclusion body responsive promoter operably linked to a second reporter gene or reporter gene cloning site configured for inserting a second reporter gene therein.

In another embodiment of the present invention concerns the single cell two-cassette reporter system comprising: a) a first cassette comprising i) a target gene or a target gene cloning site configured for inserting the target gene; ii) a first reporter gene or a first reporter gene cloning site configured for inserting a first reporter gene therein; iii) a first reporter gene translation control element that, in a transcript of the translation-coupling cassette, controls translation of the first reporter gene or a first reporter gene inserted in the first reporter gene cloning site; iv) a secondary structure-forming sequence that reversibly forms a secondary structure that masks the first reporter gene translation control element and encompasses at least a portion of the 3' end of the coding sequence of the target gene, wherein at least part of the secondary structure-forming sequence is translationally linked with the target gene cloning site or the target gene, wherein target gene translation induce unmasking of the first reporter gene translation control element, and b) a second cassette comprising i) a protein inclusion body responsive promoter operably linked to a second reporter gene or reporter gene cloning site.

In a further embodiment the present invention concerns a method of assessing target gene translation and/or target gene product solubility, the method comprising the steps of:
  a) providing the two-cassette reporter system as described herein above comprising
    i) a target gene, and
    ii) a first reporter gene encoding a first reporter protein capable of generating a first signal, and
    iii) a second reporter gene encoding a second reporter protein capable of generating a second signal, and
  b) expressing the two-cassette reporter system in a host described herein, and
  c) determining the first and/or the second signal using analysis means, and
  d) assessing the target gene translation on the basis of the first signal and/or assessing target gene product solubility on the basis of the second signal by comparison to appropriate control host cells.

In another embodiment the present invention concerns a method of assessing target gene translation and/or target gene product solubility, the method comprising the steps of:
a) providing the two-cassette reporter system of the present invention comprising
   i) a target gene, and
   ii) a first reporter gene encoding a first reporter protein capable of generating a first signal, and
   iii) a second reporter gene encoding a second reporter protein capable of generating a second signal, and
b) expressing the two-cassette reporter system in a host cell described herein, and
c) determining the first and/or the second signal using analysis means, and
d) assessing the target gene translation on the basis of the first signal and/or assessing target gene product solubility on the basis of the second signal, wherein the presence of the first signal is indicative of complete target gene translation and the presence of the second signal is indicative of target gene product inclusion body formation, wherein the signals are assessed by comparison to appropriate control host cells.

The reporter system of the present invention may be applied in combination with other reporters. Thus in an embodiment the reporter system of the present invention is used together and/or simultaneously with any other reporter system.

Target Gene

The target gene of the present may be characterized with respect to the target gene translation and/or the target gene product solubility using the reporter system of the present invention. The target gene of the present invention may be any gene encoding a target polypeptide, which may be a polypeptide fragment and/or domain. Thus in one embodiment the target gene of the present invention comprises a target polypeptide. In another embodiment target polypeptide comprises a protein fragment. In a further embodiment protein fragment comprises a protein domain.

Protein and/or peptide tags have multiple applications some of which facilitate purification of the tagged protein and/or identification of the tagged protein. It is also known that protein and/or peptide tags fused to proteins may increase translation and folding of proteins. Thus in an embodiment of the present invention the target gene further comprises at least one protein and/or peptide tag. In another embodiment the target gene further comprise protein tag-encoding sequence, wherein the protein tag-encoding sequence forms or is configured to form part of the 5' and/or 3' end of the target gene coding sequence. In another embodiment the target gene further comprises a protein tag-encoding sequence, wherein the protein tag-encoding sequence forms or is configured to form part of the 3' end of the target gene coding sequence. A non-exhaustive list of protein tags which may be used in the present invention includes polyhistidine tag, MBP-tag, Calmodulin-tag, polyglutamate tag, E-tag, SUMO-tag, NusA-tag, N-tag, FLAG-tag, HA-tag, Myc-tag, S-tag, SBP-tag, Softag 1, Softag 3, Strep-tag, Strep-tag II, TC tag, V5 tag, VSV-tag, and/or Xpress tag. Other tags such as random protein tag encoding sequences may be operationally linked to the target gene. Thus in an embodiment the protein tag-encoding sequence encodes a protein tag selected from the group consisting of a polyhistidine tag, MBP-tag, Calmodulin-tag, polyglutamate tag, E-tag, SUMO-tag, NusA-tag, N-tag, FLAG-tag, HA-tag, Myc-tag, S-tag, SBP-tag, Softag 1, Softag 3, Strep-tag, Strep-tag II, TC tag, V5 tag, VSV-tag, and/or Xpress tag. In a further embodiment the protein tag-encoding sequence comprises a polyhistidine tag. In another embodiment the protein tag-encoding sequence encodes a random protein.

The present invention may be used to test translation and folding in an expression library of target genes. An expression library may be generated using genetic material such as cDNA from one or more organisms. Generation of a target gene library may involve target gene mutagenesis means. Thus in one embodiment of the present invention the target gene is or has been mutated using mutagenesis means. In a further embodiment the target gene originate from a cDNA library or any other gene library. The target genes of the present invention may originate from a target gene expression library. Such expression library may be generated using mutagenesis means, cDNA libraries, other expression libraries, and/or a combination hereof. The genes of such expression library may derive from a multitude of organisms. Thus in an embodiment of the present invention the target gene originate from a gene library generated using mutagenesis means, cDNA library and/or any other type of expression library, and/or a combination hereof. In a further embodiment the target gene may originate from any organism.

It is known that codon usage may influence gene translation and/or gene product folding. Codon usage may be altered by mutagenesis means or by obtaining a synthetic gene. Thus in one embodiment of the present invention the target gene is codon optimized. In another embodiment the target gene is synthetic. The target gene of the present invention may originate from any organism. In an embodiment the target gene of the present invention is heterologous to the host cell in which the target gene is expressed. In another embodiment the target gene is from the same species as the host cell in which the target gene is expressed. In yet an embodiment the target gene may be a synthetic gene and/or a fusion gene.

To facilitate expression control of the target gene, a promoter may be operatively linked to the target gene of the present invention. Promoter type and/or strength may influence translation and folding of the target protein. Hence in an embodiment the reporter system described herein above further comprises a promoter operatively linked to the target gene. Two major classes of promoters exist: constitutive promoters and inducible promoters. Expression of the target gene may occur in a transient manner. Transient expression may be facilitated by an inducible promoter. The promoter operatively linked to the target gene used in the invention is not limited to any specific promoter and any promoter could be tested using the present invention. Thus in an embodiment the promoter operatively linked to the target gene is constitutive or inducible. Constitutive and/or inducible promoters are known in the art. In another embodiment promoter operatively linked to the target gene is from any organism. In a preferred embodiment the promoter operatively linked to the target gene of the present invention is of prokaryotic origin. In a further embodiment the promoter operatively linked to the target gene comprises a T7 promoter. In another embodiment the target gene promoter of the present invention is of eukaryotic origin.

Other strategies to increase and/or optimize the expression and/or folding of the target gene and/or target gene product may be co-expression of e.g. chaperone proteins or other proteins and/or co-factors which are known to aid folding of gene products such as chaperones. Thus in an embodiment the system of the present invention further comprises co-expression of chaperones and or other proteins and/or co-factors which are known to aid folding of gene products. Thus in an embodiment the system of the present invention further comprises co-expression of chaperones.

The reporter system of the present invention may be optimized for expression in various host cells. One way of optimizing expression of e.g. the target gene, the first reporter gene, and/or the second reporter gene is to change the codons used. Thus an embodiment of the present invention the target gene, the first reporter gene, and/or the second reporter gene are codon-optimized. Codon-optimization may also include changed codons, which result in lower and/or higher expression levels. Codon optimization methods are known in the art and allow optimized expression in a heterologous host organism or cell.

Reporter Genes

The present invention concerns a two-component reporter comprising a translation sensor comprising a first reporter gene and a folding sensor comprising a second reporter gene. The reporter gene product signals are dependent on the translation of a target gene and/or folding of a target gene or target gene product. Use of two different reporters for each of the two sensor components facilitates that simultaneous signals from the two reporters can be distinguished using analysis means. Thus in one embodiment of the present invention the first and second reporter gene are different. In a preferred embodiment the first and second reporter gene product can be distinguished using analysis means. In another embodiment the first and second reporter gene are identical.

Multiple reporter genes may be used in the present invention such as reporter genes encoding metabolic enzymes, antibiotic resistance proteins, luminescent proteins, chemiluminescent proteins, and/or fluorescent proteins. All of the reporter gene products of the present invention are suitable for detection. Thus in one embodiment of the present invention the first and/or the second reporter gene encodes a polypeptide, which upon expression is suitable for detection. In an embodiment the detectable polypeptide is selected from the group consisting of a metabolic enzyme, antibiotic resistance protein, luminescent protein, chemiluminescent protein, and fluorescent protein. In an embodiment the detectable polypeptide is a galactosidase. In another embodiment the detectable polypeptide comprises a luminescent and/or fluorescent protein. In a preferred embodiment the detectable polypeptide comprises a fluorescent protein.

Indirect reporter systems may also be used with any of the methods disclosed herein. An indirect reporter system is such that the reporter gene encodes a regulatory element such as a transcriptional activator or a transcriptional repressor and thus functions as an indirect reporter. Upon proper translation and/or improper folding of target protein, said regulatory elements can induce or repress transcription of a direct reporter gene, such as described above. For example, direct reporter genes preferably encode metabolic enzymes, antibiotic resistance proteins, luminescent proteins, chemiluminescent proteins, and/or fluorescent proteins. The expression of these direct reporter proteins thus reflects whether or not the target protein is fully translated and/or properly folded.

First Reporter Gene

The first reporter gene of the present invention is translationally linked to the target gene. The translational coupling of the first reporter gene to the target gene ensures that the first reporter gene is only translated upon complete translation of the target gene. A multitude of strategies for translational coupling of two genes exist. Some examples of translational coupling strategies are secondary structure mediated translational coupling, direct protein fusion mediated translational coupling, split-GFP based strategies, linkage by polynucleotide sequences encoding a polypeptide which induces a proteolytic action separating the fusion protein post translation and/or linkage by a polynucleotide which induces ribosomal skipping.

The first cassette of the single cell two-cassette reporter system of the present invention is associated with the first reporter gene. In absence of target gene translation the secondary structure-forming sequence masks the first reporter gene translation control element. The secondary mRNA structure of the secondary structure-forming sequence may be a hairpin, which is able to outcompete base-paring between the 16 S rRNA and the first reporter gene translation control element (e.g. a ribosomal binding site). Consequently the secondary structure of the secondary structure forming sequence inhibits translation of the first reporter gene. Incomplete or partial translation of the target gene does not induce unmasking of the first reporter translation control element. In this way partial or incomplete translation of the target gene does not induce translation of the first reporter gene and prevents ribosome recruitment and translation of the first reporter gene. Only when the target gene is fully translated the secondary of the secondary structure-forming sequence is disrupted and unmasks the first reporter translation control element. The ribosome is known to have RNA helicase activity and is able to translate mRNA with significant secondary structure. Consequently translation of the target gene allows the 16 S rRNA to outcompete the base-pairing of the secondary structure-forming sequence which is unfolded by the RNA helicase activity of the target gene translating ribosome. Unfolding of the secondary structure-forming sequence unmasks the first reporter gene translation control element which allow ribosome docking to the first reporter gene translation control element resulting in translation of the first reporter gene. Presence of the first reporter gene product is therefore indicative of complete target gene translation. The first cassette of the single cell two-cassette reporter system may therefore be described as a target gene translation sensor.

As described herein above multiple reporter genes may be used in the present invention. Thus in an embodiment of the present invention the first reporter gene encodes a polypeptide selected from the group consisting of a metabolic enzyme, antibiotic resistance protein, luminescent protein, chemiluminescent protein, and fluorescent protein. In an embodiment the detectable polypeptide is a galactosidase. In another embodiment the first reporter gene encodes a fluorescent protein. Shaner et al. 2005 presents a guide to choosing fluorescent proteins. A non-exhaustive list of fluorescent proteins which may be used in the present invention are mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean and/or T-Sapphire as listed in table 1 of Shaner et al. 2005. Other fluorescent proteins may be used as reporters in the present invention. In a further embodiment the first reporter gene encodes a mCherry polypeptide. In a further embodiment the mCherry polypeptide is at least 75% identical, such as 80%, such as 85%, such as 90%, such as 95%, such as 96%, such as 97%, such as 98%, such as 99% identical to the polypeptide sequence of SEQ ID NO: 5. In another embodiment the mCherry polypeptide comprises SEQ ID NO: 16.

The first reporter gene of the present invention may encode a selectable marker. Two categories of selective markers exist: positive and negative selection markers. Positive selectable markers are selectable markers that confer selective advantage to the host organism. An example would be antibiotic resistance gene, which allows the host organism to survive antibiotic selection. Use of a positive selective markers as the first reporter gene may eliminate colonies e.g. without complete target gene translation. Such elimination could be facilitated by using an antibiotic resistance gene as the first reporter gene. In such case survival on antibiotic containing media would indicate complete translation of the target gene. Negative selectable markers are selectable markers that eliminate or inhibit growth of the host organism upon selection. An example would be expression of the sacB gene, which makes the host sensitive to sucrose selection. Thus in an embodiment of the present invention the first reporter gene encodes a positive and/or negative selectable marker.

Other methods for assessing complete translation of a target gene exist. One other method is the use of a split-GFP based sensor as the first reporter gene of the present invention. In another embodiment the first reporter gene of the present invention encodes a first part of a split-GFP based sensor. In a further embodiment the first reporter gene encodes a first part of a split-GFP based sensor, wherein the two-cassette reporter system further comprising a cassette expressing a second part of a split-GFP based sensor, wherein the first and the second part of the split-GFP based sensor are capable of forming a fluorescent protein and/or similar detectable protein tags. Fusion proteins may also be able to indicate complete translation of the target gene of the present invention. Thus in another embodiment the target gene and the first reporter gene encodes a fusion protein. In a further embodiment the first and first reporter gene and the target gene of the present invention is linked by a nucleic acid sequence encoding a polypeptide sequence which induces a proteolytic action separating the target gene product from the first reporter gene product. In a further embodiment the first and first reporter gene and the target gene of the present invention is linked by a nucleic acid sequence encoding a polypeptide sequence which induces a ribosomal skip. In an embodiment the polypeptide sequence which induces a ribosomal skip is a 2A/2B polyprotein cleavage site.

The first reporter gene may encode an indirect reporter, such as a regulatory element, as described above.

Second Reporter Gene

The second reporter gene is associated with the second cassette of the single cell two-cassette reporter system described in the present invention. As described herein above multiple reporter genes may be used in the present invention. Thus in an embodiment of the present invention the second reporter gene encodes a polypeptide selected from the group consisting of a metabolic enzyme, antibiotic resistance protein, luminescent protein, chemiluminescent protein, and fluorescent protein. In an embodiment the polypeptide is a galactosidase. In an embodiment the second reporter gene encodes a fluorescent protein. Shaner et al. 2005 presents a guide to choosing fluorescent proteins. A non-exhaustive list of fluorescent proteins which may be used in the present invention are mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean and/or T-Sapphire as listed in table 1 of Shaner et al. 2005. Other fluorescent proteins may be used as reporters in the present invention.

The present inventors have demonstrated that the sensitivity of the inclusion body sensor can be significantly improved by using a destabilized version of GFP. Hence using a destabilized version of GFP in the inclusion body sensor did result in an improved signal to noise ratio. Other destabilized fluorescent proteins may yield a similar signal to noise ratio. Thus in an embodiment the second reporter gene encodes a destabilized fluorescent protein. In a further embodiment the destabilized protein has a half life between 40 minutes to 24 hours, such as 70 minutes to 12 hours, such as 70 minutes to 6 hours, such as 70 minutes to 240 minutes, such as 70 min to 150 minutes, such as 40 minutes to 120 minutes. In an embodiment the destabilized fluorescent protein is a destabilized GFP. In a further embodiment the destabilized GFP is at least 75% identical, such as 80%, such as 85%, such as 90%, such as 95%, such as 96%, such as 97%, such as 98%, such as 99% identical to the polypeptide sequence of SEQ ID NO: 14. In another embodiment the destabilized GFP polypeptide comprises SEQ ID NO: 14.

In another embodiment the second reporter gene encodes fluorescent protein. In another embodiment the fluorescent protein is a GFP family protein. In another embodiment the fluorescent protein is a GFP protein. In a further embodiment the GFP protein is at least 75% identical, such as 80%, such as 85%, such as 90%, such as 95%, such as 96%, such as 97%, such as 98%, such as 99% identical to the polypeptide sequence of SEQ ID NO: 15. In a further embodiment GFP protein comprises SEQ ID NO: 15.

The second reporter gene of the present invention may encode a selectable marker. Two categories of selective markers exist: positive and negative selection markers. Positive selectable markers are selectable markers that confer selective advantage to the host organism. An example would be antibiotic resistance gene, which allows the host organism to survive antibiotic selection. Negative selectable markers are selectable markers that eliminate or inhibit growth of the host organism upon selection. An example would be sacB kinase, which makes the host sensitive to sucrose selection. Thus in an embodiment of the present invention the second reporter gene encodes a positive and/or negative selectable marker.

The second reporter gene may encode an indirect reporter, such as a regulatory element, as described above.

Cloning Sites

The single cell two-cassette reporter system may, instead of a target gene, comprise a target gene cloning site configured for inserting the target gene in the first cassette. Likewise, the single cell two-cassette reporter system may, instead of a first reporter gene, comprise a reporter gene cloning site configured for inserting the first reporter gene or for inserting the first reporter gene therein. The reporter system may also, instead of a second reporter gene, comprise a reporter gene cloning site configured for inserting the second reporter gene, or for inserting the second reporter gene therein.

A target gene cloning site configured for inserting the target gene is, as is known to the skilled person, any site allowing insertion of the target gene therein. For example, a target gene cloning site configured for inserting a target gene may comprise a multiple cloning site (MCS). In other words, in some embodiments, one or both of the first and second cassettes of the single cell two-cassette reporter system does not comprise a target gene, but instead comprises a target gene cloning site configured for inserting the target gene. This may be a multiple cloning site or any recognition site allowing integration of the target gene therein. Examples of target gene cloning sites are multiple cloning sites allowing integration of a gene after enzymatic digestion of the cloning site; recognition sites for an endonuclease such as a Zinc-finger nuclease or a TALEN or a CRISPR/Cas-derived system. The skilled person knows how to design a target gene cloning site allowing integration of the target gene.

Accordingly, in some embodiments, the single cell two-cassette reporter system comprises:
a) a first cassette comprising
  i) a target gene cloning site configured for inserting the target gene;
  ii) a first reporter gene, wherein translation of the first reporter gene is translationally linked to the target gene;
b) a second cassette comprising
  i) a protein inclusion body responsive promoter operably linked to a second reporter gene.

In other embodiments, the single cell two-cassette reporter system comprises:
a) a first cassette comprising
  i) a target gene;
  ii) a first reporter gene cloning site configured for inserting a first reporter gene therein, wherein translation of the first reporter gene is translationally linked to the target gene;
c) a second cassette comprising
  i) a protein inclusion body responsive promoter operably linked to a second reporter gene.

In other embodiments, the single cell two-cassette reporter system comprises:
a) a first cassette comprising
  i) a target gene;
  ii) a first reporter gene, wherein translation of the first reporter gene is translationally linked to the target gene;
b) a second cassette comprising
  i) a protein inclusion body responsive promoter operably linked to a second reporter gene cloning site configured for inserting a second reporter gene therein.

In other embodiments, the single cell two-cassette reporter system comprises:
a) a first cassette comprising
  i) a target gene cloning site configured for inserting the target gene;
  ii) a first reporter gene cloning site configured for inserting the first reporter gene therein, wherein translation of the first reporter gene is translationally linked to the target gene;
b) a second cassette comprising
  i) a protein inclusion body responsive promoter operably linked to a second reporter gene.

In other embodiments, the single cell two-cassette reporter system comprises:
a) a first cassette comprising
  i) a target gene cloning site configured for inserting the target gene;
  ii) a first reporter gene, wherein translation of the first reporter gene is translationally linked to the target gene;
b) a second cassette comprising
  i) a protein inclusion body responsive promoter operably linked to a second reporter gene cloning site configured for inserting a second reporter gene therein.

In other embodiments, the single cell two-cassette reporter system comprises:
a) a first cassette comprising
  i) a target gene;
  ii) a first reporter gene cloning site configured for inserting a first reporter gene therein, wherein translation of the first reporter gene is translationally linked to the target gene;
b) a second cassette comprising
  ii) a protein inclusion body responsive promoter operably linked to a second reporter gene cloning site configured for inserting a second reporter gene therein.

In other embodiments, the single cell two-cassette reporter system comprises:
a) a first cassette comprising
  i) a target gene;
  ii) a first reporter gene, wherein translation of the first reporter gene is translationally linked to the target gene;
b) a second cassette comprising
  i) a protein inclusion body responsive promoter operably linked to a second reporter gene.

In other embodiments, the single cell two-cassette reporter system comprises:
a) a first cassette comprising
  i) a target gene cloning site configured for inserting the target gene;
  ii) a first reporter gene cloning site configured for inserting a first reporter gene therein, wherein translation of the first reporter gene is translationally linked to the target gene;
b) a second cassette comprising
  i) a protein inclusion body responsive promoter operably linked to a second reporter gene cloning site configured for inserting a second reporter gene therein.

By the use of cloning sites configured for inserting or inserting the target gene, the first reporter gene and/or the second reporter gene, the present systems allow great flexibility of use and can be adapted to various target genes and reporter genes. The skilled person is well aware that cloning sites configured for inserting or inserting a gene can be used with many different genes, e.g. by adapting the sequence of these genes.

A multiple cloning site, also called a polylinker, is a short segment of DNA, which contains many (up to ~50) restriction sites and is a standard feature of engineered plasmids. Thus in an embodiment of the present invention the target gene cloning site and/or the reporter gene cloning site includes a multiple cloning site. In another embodiment any of the cloning sites of the present invention may be a multiple cloning site.

Another cloning strategy is ligation-independent cloning. Ligation-independent cloning is a form of molecular cloning that is able to be performed without the use of restriction endonucleases or DNA ligase. This allows genes that have restriction sites to be cloned without being limited by the presence/absence of specific restriction sites. Many strategies for ligation independent cloning exist and are known to the skilled person. Most of the ligation independent cloning systems may be used in the present invention. Thus in an embodiment of the present invention target gene cloning site and/or the reporter gene cloning site(s) includes a ligation-independent cloning site. In another embodiment any of the cloning sites of the present invention may be a ligation-independent cloning site.

The cloning sites of the present invention may be a combination of cloning sites. Thus in an embodiment the cloning sites of the present invention are different from each other. In another embodiment the cloning sites of the present invention is a combination of multiple cloning sites and ligation independent cloning sites.

First Reporter Gene Translation Control Element

In absence of target gene translation the secondary structure-forming sequence masks the first reporter gene translation control element. The secondary mRNA structure of the secondary structure-forming sequence may be a hairpin, which is able to outcompete base-paring between the 16 S rRNA and the first reporter gene translation control element (e.g. a ribosomal binding site). Consequently the secondary structure inhibits translation of the first reporter gene. Incomplete or partial translation of the target gene may not induce unmasking of the first reporter translation control element. In this way partial or incomplete translation of the target gene does not induce translation of the first reporter gene and prevents ribosome recruitment and translation of the first reporter gene. Only when the target gene is fully translated the secondary of the secondary structure-forming sequence is disrupted and unmasks the first reporter translation control element. The ribosome is known to have RNA helicase activity and is able to translate mRNA with significant secondary structure such as a stem loop and/or hairpin structure formation. Consequently translation of the target gene allows the 16 S rRNA to outcompete the base-pairing of the secondary structure-forming sequence which is unfolded by the RNA helicase activity of the target gene translating ribosome. Unfolding of the secondary structure-forming sequence unmasks the first reporter gene translation control element which allow ribosome docking and first reporter gene translation. Presence of the first reporter gene product is therefore indicative of complete target gene translation. The first cassette of the single cell two-cassette reporter system may therefore be described as a target gene translation sensor wherein the first reporter gene translation control element controls the translation of the first reporter gene by means of translational linking means. Thus in an embodiment of the present invention the first reporter gene translation control element is translationally linked to the target gene cloning site or the target gene.

Translation of mRNA into polypeptides is mediated by the ribosomes. Prior to translation the ribosome searches for a mRNA binding site through base-pairing of nucleotides. A ribosomal binding site (RBS) is a sequence on mRNA that is bound by the ribosome when initiating protein translation. Thus in an embodiment of the present invention the first reporter gene translation control element comprises a ribosome binding site.

A ribosome binding site in a prokaryotic organism may be a region 6-7 nucleotides upstream of the start codon AUG called the Shine-Dalgarno sequence which sequence is complementary to the 3' end of prokaryotic rRNA. Thus in one embodiment of the present invention the ribosome binding site comprises a Shine-Dalgarno sequence or derivative thereof. Shine-Dalgano sequence derivatives are known to the skilled person.

A ribosome binding site in an eukaryotic organism can be the 5' cap of a messenger RNA which sequence is complementary to the 3' end of the eukaryotic rRNA. After finding the ribosome binding site in eukaryotes, the ribosome recognizes the Kozak consensus sequence and begins translation at the +1 AUG codon. Thus in one embodiment of the present invention the first reporter gene translation control element further comprises a kozak consensus sequence or derivative thereof. Kozak consensus sequence derivatives are known to the skilled person.

To facilitate the hairpin formation of the secondary forming sequence the target gene and the first reporter gene translation control element may be complementary to at least a portion of the 3' end of the coding sequence of the target gene. Consequently a linker sequence between the first reporter gene translation control element and the reporter gene or the reporter gene cloning site may be used. Thus an embodiment of the present invention the first cassette further comprises a linker disposed between the first reporter gene translation control element and the first reporter gene or the first reporter gene cloning site. The linker sequence is configured to form a hairpin structure with the 3' end of the coding sequence of the target gene.

Secondary Structure-forming Sequence

The secondary structure of the secondary structure forming sequence is configured to inhibit translation of the first reporter gene by preventing ribosome recruitment to the first reporter gene control element. The secondary structure of the secondary structure forming sequence may be a stem loop and/or hairpin structure capable of reversibly outcompeting the base-pair binding between the rRNA and the ribosomal binding site of the first reporter gene translation control element. Thus an embodiment of the present invention the secondary structure formed by the secondary structure-forming sequence in the transcript comprises a stem loop structure. In a further embodiment the secondary structure formed by the secondary structure-forming sequence in the transcript comprises a hairpin structure.

To allow disruption of the secondary structure of the secondary structure forming sequence upon translation the secondary structure forming sequence of the present invention encompasses at least a portion of the 3' end of the coding sequence of the target gene. This allows the ribosomal helicase activity following complete target gene translation to disrupt the secondary structure of the secondary structure forming sequence. When the structure of the secondary structure forming sequence is disrupted rRNA may outcompete the base-pair binding between the secondary structure and the ribosomal binding site of the first reporter gene translation control element. Thus in an embodiment of the present invention the secondary structure-forming sequence at least partially includes the first reporter gene translation control element. In another embodiment the secondary structure-forming sequence further includes a stop codon, the stop codon being translationally linked to the target gene cloning site or translationally linked in-frame with the target gene.

To design the secondary structure forming sequence comprising the 3' end of the target gene coding sequence and the first reporter gene translation control element a multitude of prediction software and computational tools exist. Simple RNA structure prediction such as stem-loop and/or hairpin formation prediction is known to the skilled person. A non-exhaustive list of RNA structure prediction software may be found at the World Wide Web such as at Wikipedia.org: http://en.wikipedia.org/wiki/List_of_RNA_structure_prediction_software. Use of this software can aid to design the 3' end of the target gene coding sequence and the first reporter gene translation control element to facilitate secondary structure formation in the secondary structure forming sequence. Thus in an embodiment of the present invention the secondary structure-forming sequence comprises a sequence that forms secondary structure in the transcript of the first cassette. In a further embodiment the secondary structure-forming sequence comprises at least one nucleotide which, in the transcript of the first cassette, base pairs directly with at least a portion of the first reporter gene translation control element, wherein the at least one nucleotide is translationally linked to the target gene cloning site or the target gene. In another embodiment the secondary structure-forming sequence as described herein above is determined on the basis of the 3' end of the target gene coding sequence.

Inclusion Body Responsive Promoter

Although proteins can typically fold by themselves, most organisms have evolved mechanisms for controlling and aiding the process. Molecular chaperones typically assist in protein folding, and they can prevent polypeptide chains from aggregating before the correct protein folding has been achieved. Chaperones can either actively participate in protein folding using an energy dependent mechanism, or they can passively bind peptide chains, thereby preventing unwanted protein aggregation (Goloubinoff et al 2014). Most molecular chaperones fall into a few conserved protein families, including Hsp100s (ClpB), Hsp90s (HtpG), Hsp70/Hsp110 (DnaK), Hsp60/CCTs (GroEL), as well as small heat shock proteins (IbpA/B). The chaperones bind to hydrophobic residues that are abnormally exposed to the cytosolic environment, and are thus prone to associate and form stable inactive aggregates. Chaperones are typically induced during stress conditions, and the proteins are often referred to heat shock proteins (Hsp). Expression of chaperones may differ from organism to organism, and this may contribute to the lack of predictability of folding of heterologously expressed proteins.

The second cassette of the present invention comprises an inclusion body responsive promoter. Many inclusion body chaperones have been described, some are from prokaryotes including Hsp100s (ClpB), Hsp90s (HtpG), Hsp70/Hsp110 (DnaK), Hsp60/CCTs (GroEL), as well as small heat shock proteins (IbpA/B) and others are from eukaryotes. Table 1 of Lesley et. Al. 2002 provides a list of genes, which are induced upon presence of misfolded proteins in *E. coli*. All promoters that are induced by protein misfolding may be used in the present invention. In an embodiment of the present invention the an inclusion body responsive promoter is selected from the group consisting the promoter controlling the expression of the ibpAB, yrfH, yccV, fsxA, dnaK, htpG, groEL, yhdN, yagU, yciS, ybeD, clpB and araE gene from *E. coli*. The reporter of the present invention may be used in both prokaryotic and eukaryotic expression systems. Thus in an embodiment of the present invention the protein inclusion body responsive promoter comprises a prokaryotic promoter. In another embodiment the protein inclusion body responsive promoter comprises a Gram negative bacterial promoter. In an embodiment the Gram negative bacteria is a member of the family Enterobacteriaceae. In an embodiment the member of the family Enterobacteriaceae is selected from the group consisting of the genera *Escherichia, Salmonella, Shigella, Klebsiella* and *Enterobacter*. In a preferred embodiment the wherein the Gram negative bacteria is *E. coli*. In a more preferred embodiment the protein inclusion body responsive promoter is from *E. coli*.

The protein inclusion body responsive promoter of the present invention may be from a gram positive bacteria. Thus in an embodiment of the present invention the protein inclusion body responsive promoter comprises a Gram positive bacterial promoter. In another embodiment the protein inclusion body responsive promoter is of gram positive bacterial origin.

The protein inclusion body responsive promoter of the present invention may be from an eukaryotic organism. Thus in an embodiment of the present invention the protein inclusion body responsive promoter comprises an eukaryotic promoter. In another embodiment the protein inclusion body responsive promoter is of eukaryotic origin. In a further embodiment the protein inclusion body responsive promoter comprises a mammalian, plant, insect, fungal, or yeast promoter. In another embodiment the protein inclusion body responsive promoter is from the group selected from a mammal, plant, insect, fungal, or yeast. In another embodiment the protein inclusion body responsive promoter comprises a mammalian, plant, insect, fungal, or yeast promoter.

Inclusion body responsive promoters are often involved in the heat shock response of a cell. The alternative sigma factor $\sigma^{32}$ (RpoH) may be referred to as the heat shock sigma factor which is induced when a bacteria is exposed to heat. Heat may cause inclusion body formation, which may induce alternative sigma factor $\sigma^{32}$ dependent promoters. Thus in an embodiment of the present invention the protein inclusion body responsive promoter comprises an alternative sigma factor $\sigma^{32}$ (RpoH) controlled promoter. In another embodiment the inclusion body responsive promoter is a promoter which is RpoH induced. Some alternative sigma factor $\sigma^{32}$ dependent promoters are heat shock promoters which may also be used in the present invention. Thus in an embodiment of the present invention the protein inclusion body responsive promoter comprises a heat shock protein promoter. In another embodiment the protein inclusion body responsive promoter comprises an Hsp100s (ClpB), Hsp90s (HtpG), Hsp70/Hsp110 (DnaK), Hsp60/CCTs (GroEL) ibpAB and/or fxsA promoter. In another embodiment the protein inclusion body responsive promoter comprises an ibpAB and/or fxsA promoter. The ibpAB operon encodes two small heat-shock proteins, the inclusion-body-binding proteins IbpA and IbpB. Thus in an embodiment of the present invention protein inclusion body responsive promoter comprises an ibpAB promoter. In another embodiment of the present invention protein inclusion body responsive promoter comprises an ibpAB promoter from *E. coli*. In a further embodiment the protein inclusion body responsive promoter comprises a polynucleotide sequence at least 75% identical, such as 80%, such as 85%, such as 90%, such as 95%, such as 96%, such as 97%, such as 98%, such as 99% identical to the polynucleotide of SEQ ID NO: 1. In yet an embodiment the protein inclusion body responsive promoter comprises a polynucleotide comprising SEQ ID NO: 1.

The inclusion body responsive promoter may be induced upon the presence of target gene product inclusion bodies such as the ibpAB promoter. Thus in an embodiment the protein inclusion body responsive promoter of the present invention is induced when the target gene product forms inclusion bodies inter alia. The inclusion body responsive promoter of the present invention may suppressed by the presence of inclusion bodies. Thus in an embodiment of the present invention protein inclusion body responsive promoter is suppressed when the target gene product forms inclusion bodies.

Vector

The present invention further concerns a vector comprising the reporter system of the present invention. In molecular cloning, a vector is a DNA molecule used as a vehicle to artificially carry foreign genetic material into a cell, where it can be replicated and/or expressed. The four major types of vectors are plasmids, viral vectors, cosmids, and artificial chromosomes. The vector itself is generally a DNA sequence that comprises one or more inserts (transgenes) and a larger sequence that serves as the "backbone" of the vector. The purpose of a vector which transfers genetic information to another cell is typically to isolate, multiply, or express the insert in the target cell. Expression vectors (expression constructs) specifically are for the expression of transgenes in target cells, and generally have a promoter sequence that drives expression of the transgenes.

Thus an aspect of the present invention concerns a vector comprising the two-cassette reporter system described herein above. The present invention concerns two cassettes each comprising a sensor element. The two cassettes of the present invention may be situated on the same vector or on separate vectors. Thus in an embodiment the first and second cassette of the two-cassette system described herein above are located on the same vector. In another embodiment the first and second cassettes are located on separate vectors. Any vector may be used in the present invention. The inventors have demonstrated that the vector backbone impacts the functionality of the folding reporter system. According to the result a medium copy number plasmid (pBPR1) resulted in a 5-fold increase of the signal to noise ratio in comparison with a high copy number plasmid with the ColE1 origin of replication. This result indicates that medium and/or low copy number plasmids may be preferable over high copy number plasmids. Thus in an embodiment the vector comprising the second cassette is a medium and/or low copy number plasmid. In another embodiment the vector comprising the second cassette is a medium copy number plasmid. In another embodiment the vector of the present invention is derived from the pBBR1 vector and/or the p15A vector. In another embodiment the vector of the present invention is derived from the pBBR1 vector. In another embodiment the vector of the present invention is derived from the p15A vector.

The vector and/or vectors of the present invention may be used to introduce parts of the two-component reporter into the genome of the host cell described herein above and in the following section. Thus in an embodiment the vector of the present invention may be used to introduce the two-component reporter of the present invention into the genome of the host cell described in the present invention. Other non-vector based approaches for introducing DNA into the genome of a host organism exist. Thus in an embodiment of the present invention the reporter or parts hereof are introduced into the genome of a host cell by means of non-vector based transformation. Vector and non-vector based transformation protocols of all host cells are known to the skilled person.

The single cell two-cassette reporter system as described herein above may be located on one and/or two vectors suitable for being introduced into a host cell. In an embodiment of the present invention the first and the second cassettes are included within one and/or two vectors capable of being introduced in a host cell.

Host Cell

To facilitate single cell assays the present invention further concerns a host cell comprising the two-reporter system of the present invention and/or a vector comprising the two-reporter system of the present invention. The inventors have experimentally shown that the reporter of the present invention can be used in bacteria such as E. coli. However, the concept of the present invention may be implemented into other host cells such as other prokaryotes, other bacteria, yeast cells, fungal cells, insect cells, plant cells, and/or mammalian cells. Thus in an embodiment of the present invention the host cell comprising the reporter system described herein above is selected from the group consisting of prokaryotes, bacteria, yeast, fungal, insect, plant, and/or mammalian host cells. In a further embodiment the host cell of the present invention is a prokaryotic organism. In another embodiment the host cell is a bacteria.

In another embodiment the host cell comprising the system of the present invention is E. coli. In another embodiment the host cell comprising the system of the present invention is a yeast. In yet an embodiment the host cell comprising the system of the present invention is an eukaryotic organism.

The target gene of the present invention may originate from any organism. In an embodiment the target gene of the present invention is heterologous to the host cell. In another embodiment the target gene is from the same species as the host cell. In yet an embodiment the target gene may be a synthetic gene and/or a fusion gene.

Variants of the two-cassette reporter system may be generated e.g. sensors having different reporter genes, promoters, vector backbones etc. may be used separately and/or simultaneously. Thus in an embodiment the host cell described herein above further comprising at least one other two-cassette reporter system of the present invention.

In a further embodiment the host cell is mutated using mutagenesis means prior to inserting the two-cassette reporter system of the present invention. This would enable improvement of the protein production and/or protein folding capacity in the host cell. In a further embodiment the target gene translation and/or target gene product folding is assessed in said mutated host cell comprising the two-cassette reporter system, wherein the assessment is carried out using analysis means as described herein. In a further embodiment the folding of the target gene product is assessed in said mutated host cell comprising the second reporter cassette system, wherein the assessment of protein folding is carried out using analysis means as described herein. In a further embodiment a polynucleotide sequence information of the mutated host cell comprising the reporter system as described herein is obtained. In an embodiment the polynucleotide sequence information comprises obtaining genome polynucleotide information and/or transcriptome polynucleotide information from the host cell.

In a further embodiment the host cell further comprising at least two-cassette reporter systems, such as three, such as four two-cassette reporter systems described in the present invention.

A Method of Assessing Translation and Folding

The inventors have shown that the present invention may be used to assess translation and/or folding of a target gene and/or target gene product. Expression and folding are two crucial factors in heterologous protein production. Thus a major aspect of the present invention relates to a method of assessing target gene translation and/or target gene product solubility and/or folding, the method comprising the steps of:

a) providing the two-cassette reporter system as described herein above comprising
   i) a target gene as described herein above, and
   ii) a first reporter gene as described herein above, and
   iii) a second reporter gene as described herein above, and
b) expressing the two-cassette reporter system in a host cell as described herein above, and
c) assessing the target gene translation and/or target gene product solubility and/or folding using analysis means by comparison to appropriate control host cells.

Anther embodiment of the present invention relates to a method of assessing target gene translation and/or target gene product solubility and/or folding, the method comprising the steps of:

a) providing the two-cassette reporter system as described herein above comprising
  i) a target gene as described herein above, and
  ii) a first reporter gene as described herein above, and
  iii) a second reporter gene as described herein above, and
b) expressing the two-cassette reporter system in a host cell as described herein above, and
c) determining the first and/or the second signal using analysis means, and
d) assessing the target gene translation on the basis of the first signal and/or assessing target gene product solubility on the basis of the second signal, wherein the presence of the first signal is indicative of complete target gene translation and the presence of the second signal is indicative of target gene product inclusion body formation, wherein the assessment is conducted by comparison to appropriate control host cells.

The analysis means of the method described herein above is dependent on the features of the first and/or second reporter gene. Analysis means may be fluorescence based methods. If the first and/or second reporter gene encodes a fluorescent polypeptide as described herein above fluorescent based analysis means may be used. Thus in an embodiment the analysis means described herein is a fluorescence based method. In another embodiment of the analysis means in the method described herein above are fluorescence based. In a further embodiment the analysis means is selected from the group consisting of fluorescence plate reading means, fluorescence microscopy means, fluorescence based colony pick means, fluorescent based imaging means, micro-droplet based microfluidic cell sorting means, flow cytometry means. Other fluorescence based analysis means may be used in the present invention. The present inventors have shown how cell sorting may be used to select host cells with desirable features. Cell sorting may for example be used to separate cells with altered target gene translation and/or target gene product solubility. As shown by the inventors cell sorting may be used to enrich a sample with improved solubility and/or folding while assuring that the selected cells have complete target gene translation. Thus in an embodiment of the present invention host cells are subjected to cell sorting. In another embodiment of the present invention host cell is subjected to cell sorting to separate cells with altered target gene translation and/or target gene product solubility. Several cell sorting methods exist such as fluorescence activated cell sorting (FACS) as shown by the present inventions. Thus in an embodiment of the present invention the cell sorting comprises fluorescence activated cell sorting (FACS).

It may be desirable to obtain genomic information about host cells which have been analysed. Genomic information may include the polynucleotide sequence of the target gene, transcription level of the target gene, transcription level of other genes in the host cell, and/or the polynucleotide sequence of the host cell genome and/or parts hereof. DNA/RNA sequencing methods are known in the art. Thus in an embodiment the method described herein above further comprising obtaining a polynucleotide sequence information of at least one host cell comprising the reporter system as described herein. In another embodiment the method as described herein above further comprises obtaining a polynucleotide sequence of the target gene in at least one cell line.

Kit of Parts

The present invention may be used to optimize gene translation and/or gene product folding. The present invention may be utilized to test translation and folding of any target gene or target gene product, respectively. Thus an aspect of the present invention concerns a kit of parts comprising
  a) a two-cassette reporter system as described herein above, and
  b) instructions on how to use the two-cassette reporter system.

Variants of the two-cassette reporter system may be generated e.g. sensors having different reporter genes, promoters, vector backbones etc. may be used separately and/or simultaneously. Thus in an embodiment the kit of parts described herein above further comprising at least one other two-cassette reporter system as described herein above.

Method of Assessing Translation and/or Folding in an Expression Library

The inventors have shown that the present two-cassette reporter system may be used for high-throughput screening of an expression library comprising mutants of a specific gene. Such high-throughput screening enables rapid optimization and/or assessment of the translation and/or folding of a specific target polypeptide. The present invention may be used to identify and/or characterize host cells with increased concentration of correctly folded target gene products. Thus an aspect of the present invention relates to a method of assessing target gene translation and/or target gene product solubility and/or folding in a target gene library to identify library members that express target genes with altered translation and/or target gene product solubility, the method comprising the steps of
  a) providing a target gene library described herein above comprising a plurality of vectors comprising the two-cassette reporter system described herein above, each vector comprising
    i) a target gene described herein above, and
    ii) a first reporter gene described herein above, and
    iii) a second reporter gene described herein above, and
  b) expressing the target gene library in a plurality of host cells described herein above, and
  c) assessing the target gene translation and/or target gene product solubility of the host cells using analysis means describe herein above, by comparison to appropriate control host cells.

In an embodiment the present invention relates to a method of assessing target gene translation and/or target gene product solubility and/or folding in a target gene library to identify library members that express target genes with altered translation and/or target gene product solubility, the method comprising the steps of
  a) providing a target gene library described herein above comprising a plurality of vectors comprising the two-cassette reporter system described herein above, each comprising
    i) a target gene described herein above, and
    ii) a first reporter gene described herein above, and
    iii) a second reporter gene described herein above, and
  b) expressing the target gene library in a plurality of host cells described herein above, and
  c) assessing the target gene translation and/or target gene product solubility of the host cells using analysis means describe herein above, by comparison to appropriate control host cells.

In another embodiment the present invention concerns a method of assessing target gene translation and/or target gene product solubility, the method comprising the steps of:

a) providing the two-cassette reporter system as described herein above comprising
   i) a target gene, and
   ii) a first reporter gene encoding a first reporter protein capable of generating a first signal, and
   iii) a second reporter gene encoding a second reporter protein capable of generating a second signal, and
b) expressing the two-cassette reporter system in a host cell described herein, and
c) determining the first and/or the second signal using analysis means, and
d) assessing the target gene translation on the basis of the first signal and/or assessing target gene product solubility on the basis of the second signal, wherein the presence of the first signal is indicative of complete target gene translation and the presence of the second signal is indicative of target gene product inclusion body formation, wherein the assessment is conducted by comparison to appropriate control host cells.

It may be desirable to obtain genomic information about host cells which have been analysed. Genomic information may include the polynucleotide sequence of the target gene, transcription level of the target gene, transcription level of other genes in the host cell, and/or the polynucleotide sequence of the host cell genome or parts hereof. DNA/RNA sequencing methods are known in the art. Thus in an embodiment the method described herein above further comprising obtaining a polynucleotide sequence information of at least one host cell comprising the reporter system of the present invention. In another embodiment the method as described herein above further comprises obtaining a polynucleotide sequence of the target gene in at least one host cell.

In order to generate an expression library to test the translation and folding of multiple target genes mutated gene libraries may be generated. Thus in one embodiment of the present invention the target gene and/or the target gene library has been mutated using mutagenesis means. In another embodiment of the present invention the target gene has been mutated using mutagenesis means. In a further embodiment the target gene originate from a cDNA library or any other gene library. The target genes of the present invention may originate from a target gene expression library. Such expression library may be generated using mutagenesis means, cDNA libraries, other expression libraries, and/or a combination hereof. The genes of such expression library may derive from a multitude of organisms. Thus in one embodiment of the present invention the target gene originate from a gene library generated using mutagenesis means, cDNA library, any other type of expression library, and/or a combination hereof. In another embodiment the target gene library described herein above has been mutated using mutagenesis means. In a further embodiment the target gene may originate from any organism.

Method of Assessing Effects of Growth Conditions on Translation and/or Folding

It is known that the growth conditions of a host cell can affect the gene expression, translation and/or gene product folding. The two-cassette reporter of the present invention may be used to assess the effects of growth conditions on translation and/or folding of a target polypeptide. Thus an aspect of the present invention relates to a method of assessing the effect of host cell growth conditions on target gene translation and/or target gene product solubility, comprising the steps of:

a) providing the two-cassette reporter system described herein above comprising
   i) a target gene described herein above, and
   ii) a first reporter gene described herein above, and
   iii) a second reporter gene described herein above, and
b) expressing the two-cassette reporter system in a host cell described herein above under various growth conditions, and
c) assessing the gene translation and/or target gene product solubility using analysis means described herein above, by comparison to appropriate control host cells.

In another embodiment the present invention relates to a method of assessing the effect of host cell growth conditions on target gene translation and/or target gene product solubility, comprising the steps of:

a) providing the two-cassette reporter system described herein above comprising
   i) a target gene described herein above, and
   ii) a first reporter gene described herein above, and
   iii) a second reporter gene described herein above, and
b) expressing the two-cassette reporter system in a host cell above under various growth conditions, and
c) determining the first and/or the second signal using analysis means, and
d) assessing the target gene translation on the basis of the first signal and/or assessing target gene product solubility on the basis of the second signal, wherein the presence of the first signal is indicative of complete target gene translation and the presence of the second signal is indicative of target gene product inclusion body formation, wherein the assessment is conducted by comparison to appropriate control host cells.

It is known to the skilled person which growth condition parameters may influence the translation of a target gene and/or folding of a target protein. Growth condition parameters which may be tested are: temperature, pH, agitation rate, growth media composition, co-factors, light conditions, atmosphere composition, co-culturing, co-expression of proteins, and/or host cell organism etc. However, other parameters may be tested as well.

Method of Developing a Translation and/or Folding Algorithm.

The understanding of the relationship between nucleotide sequence, protein translation and/or protein folding is not well understood. The present invention represents a high-throughput tool for investigating this relationship. Thus an aspect of the present invention relates to a method of developing a target gene translation and target gene product solubility prediction algorithm, comprising the steps of:

a) providing a target gene library as described herein above comprising a plurality of vectors comprising the system as described herein above each comprising
   i) a target gene as described herein, and
   ii) a first reporter gene as described herein, and
   iii) a second reporter gene as described herein, and
b) expressing the target gene library in a plurality of host cells as described herein, and
c) assessing the target gene translation and/or target gene product solubility of the host cells using analysis means as described herein, and
d) optionally obtaining the polynucleotide sequence of the target gene of the assessed host cells as described herein, and
e) developing a target gene translation and target gene product solubility prediction algorithm.

A gene translation and target gene product solubility prediction algorithm developed as described above may be used for prediction of gene translation and target gene product solubility. Thus another aspect of the present invention relates to a protein translation and/or folding prediction algorithm developed using the method described herein above and/or the reporter system of the present invention.

Inclusion Body Sensor

It may be desirable to only to use the second cassette comprising the inclusion body sensor of the present invention for assessing the formation of inclusion bodies. Thus an aspect of the present invention concerns an inclusion body responsive reporter system comprising
  a) a target gene or a target gene cloning site configured for inserting the target gene as described herein above; and
  b) a protein inclusion body responsive promoter operably linked to a second reporter gene or reporter gene cloning site as described herein, wherein the second reporter gene encodes a second protein capable of generating a second signal as described herein above.

In an embodiment the second reporter gene encodes a fluorescent protein. Shaner et al. 2005 presents a guide to choosing fluorescent proteins. Fluorescent proteins which may be used in the present invention are mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean and/or T-Sapphire as listed in table 1 of Shaner et al. 2005. Other fluorescent proteins may be used as the second reporter gene in the inclusion body sensor of the present invention.

The present inventors have demonstrated that the sensitivity of the inclusion body sensor can be significantly improved by using a destabilized version of GFP. Hence using a destabilized version of GFP in the inclusion body sensor did result in an improved signal to noise ratio. Other destabilized fluorescent proteins may yield a similar signal to noise ratio. Thus in an embodiment the second reporter gene encodes a destabilized fluorescent protein. In an embodiment the destabilized fluorescent protein is a destabilized GFP. In a further embodiment the destabilized GFP is at least 75% identical, such as at least 80%, such as at least 85%, such as at least 90%, such as at least 95%, such as at least 96%, such as at least 97%, such as at least 98%, such as at least 99% identical to the polypeptide sequence of SEQ ID NO: 14. In another embodiment the destabilized GFP polypeptide comprises or consists of SEQ ID NO: 14.

In another embodiment the fluorescent protein is a GFP family protein. In another embodiment the fluorescent protein is a GFP protein. In a further embodiment the GFP protein is at least 75% identical such as 75%, such as at least 80%, such as at least 85%, such as at least 90%, such as at least 95%, such as at least 96%, such as at least 97%, such as at least 98%, such as at least 99% identical to the polypeptide sequence of SEQ ID NO: 15. In a further embodiment GFP protein comprises or consists of SEQ ID NO: 15.

Host Cell with Inclusion Body Sensor

Another aspect of the present invention concerns a host cell as described herein above comprising the inclusion body responsive reporter system as described herein above. Such sensor may be desirable to utilize if only the target gene product folding is to be assessed.

A Method of Assessing Inclusion Body Formation

Another aspect of the present invention concerns a method of assessing target gene product inclusion bodies, the method comprising the steps of:
  a) providing the inclusion body responsive reporter system descried herein above comprising
    i) a target gene described herein above, and
    ii) a second reporter gene, comprising a gene encoding a second reporter protein capable of generating a second signal described herein above, and
  b) expressing the inclusion body responsive reporter system in a host cell described herein above, and
  c) assessing the target gene product solubility using analysis means described herein above, wherein the assessment is conducted by comparison to appropriate control host cells.

Kit of Parts Comprising an Inclusion Body Sensor

Another aspect of the present invention concerns a kit of parts comprising
  a) an inclusion body responsive reporter described herein above, and
  b) instructions on how to use the reporter system.

A Method for Identifying Residues Important for Correct Folding

The systems and methods described herein are also useful for predicting the structure of a protein of interest.

Accordingly, there is provided a method for identifying residues important for correct folding of a protein, said method comprising the steps of:
  a) providing a target gene library comprising a plurality of vectors comprising the system described herein above, each comprising
    i) a target gene described herein above encoding said protein, and
    ii) a second reporter gene comprising a gene encoding a second protein, capable of generating a second signal, and
    iii) optionally, a first reporter gene comprising a gene encoding a first protein, capable of generating a first signal, and
  b) expressing the target gene library in a plurality of host cells described herein above, and
  c) sorting the cells into at least two populations on the basis of the second and optionally of the first signal,
  d) isolating the vectors comprised in the cells of the sorted populations, and
  e) identifying the sequence of the target genes comprised within said isolated vectors,
  f) comparing the sequences of the target genes of the two sorted populations,
thereby identifying the sites in said sequences which differ in the two sorted populations.

Such methods can be used to identify mutations leading to misfolding.

In some embodiments, the second reporter gene and the first reporter gene are as described herein elsewhere. The second reporter gene acts as a protein folding sensor and generates a second signal when the protein encoded by the target gene is in an insoluble or in a poorly soluble form. The first reporter gene acts as a translation sensor and generates a first signal when the protein encoded by the target gene is fully translated. Preferably, the first and/or second reporter gene encodes a first and/or a second fluorescent protein. Preferably, the first and second fluorescent proteins are different and emit a first signal and a second signal that can be discriminated.

In some embodiments, the present method may thus be used by sorting the cells in two populations, where the first population comprises the cells that do not emit the first signal corresponding to poor solubility or insolubility of the protein, while the second population comprises the cells that do emit the first signal. The vectors comprised within the cells of each population are then isolated and sequenced in order to identify the mutations potentially over represented in either population. By mapping said mutations, and optionally analysing their frequency, the user can identify codons in which mutations lead to misfolding of the corresponding protein.

The method may comprise an additional step of sorting the cells based on the intensity of the optional first signal, which preferably reflects the translation of the protein. Thus in some embodiments, the first signal is as described herein elsewhere, and a positive first signal indicates that the protein is fully translated, while a negative first signal indicates that the protein is not fully translated. The analysis and prediction of mutations leading to misfolding of the proteins may be facilitated if the cells expressing proteins which are not fully translated are removed from the population. Such cells can be removed either prior to, or simultaneously with, the cells being sorted according to the intensity of the second signal.

It will be understood that the cells may be sorted in more than two populations, in particular where it might be desirable to investigate which amino acid residues are responsible for partial decrease of solubility.

Such a method may be useful not only for gaining knowledge about which residues are important for correct folding of a protein, but also for diagnostic purposes. Some disorders are known to be due to misfolding of proteins, some of which might be caused by e.g. SNPs (small nucleotide polymorphism). The present methods may be used to identify amino acid residues responsible for or correlated to specific disorders or diseases. The present methods may also be used to confirm or infirm that a subject, from which the target gene is isolated or derived, and which is suspected of suffering from a disorder or disease, is indeed suffering from said disorder or disease. Several diseases and disorders are linked to misfolding of proteins, for example because of aggregation of misfolded proteins or because of lack of protein function. Such decreases including for example cancers, diabetes, cystic fibrosis, phenylketonuria, Parkinson's disease, α-1-antitrypsin deficiency, prion diseases and Alzheimer's disease (Gregersen et al., 2005).

Such methods can be performed in a high-throughput manner.

A Method for Screening Pharmacoperones

Another method described herein is a method for screening libraries of small chaperone molecules, also known as pharmacological chaperones or pharmacoperones. Pharmacoperones are small molecules which are able to enter a cell and act as a scaffold to restore proper folding of otherwise misfolded proteins.

Accordingly, in one aspect, is provided a method for screening pharmacoperones comprising the steps of:
a) providing a host cell expressing a system as described herein above, said system comprising
  i. a target gene described herein above encoding a protein, and
  ii. a second reporter gene comprising a gene encoding a second reporter protein, capable of generating a second signal, and
  iii. optionally, a second reporter gene comprising a gene encoding a first reporter protein, capable of generating a first signal, and
b) providing a plurality of molecules to be screened for pharmacoperone activity,
c) contacting said host cell with said plurality of molecules,
d) analysing the second and optionally the first signal, and optionally sorting the cells based on the second and optionally the first signal, thereby determining which molecules can restore proper folding of the protein.

The plurality of molecules to be screened for pharmacoperone activity may be tested simultaneously or sequentially. If simultaneous screening is performed, it may be convenient to use microtiter plates where each well comprises one candidate pharmacoperone. Micro-droplets can also be used for simultaneous screening.

As described earlier in the paragraph "Second reporter gene", the second reporter gene may act as a protein folding sensor and generates a second signal when the protein encoded by the target gene is in an insoluble or in a poorly soluble form.

The first reporter gene and the corresponding signal may be reporter of incomplete translation and may thus facilitate the above method by allowing sorting of the cells in which translation is incomplete, thereby reducing the background signal. The first reporter gene may be as described in the paragraph "First reporter gene".

The first and/or second reporter genes may be a first and a second fluorescent protein. They may also be genes coding for proteins involved in antibiotics resistance.

It will be understood that it is also possible to test whether a molecule can act as a pharmacoperone for a given protein or for a plurality of proteins. For example, in some embodiments, only one molecule to be screened for pharmacoperone activity is provided, and its activity is tested by contacting it with a target gene library as described in the paragraph "a method for predicting protein structure" above. In this case, it is possible to identify for which proteins the molecule acts as a pharmacoperone by restoring their folding.

Accordingly, herein is also described a method for identifying the target proteins of a pharmacoperone, comprising the steps of:
a) providing a target gene library comprising a plurality of vectors comprising the system described herein above, each comprising
  i. a target gene described herein above encoding a protein, and
  ii. a second reporter gene comprising a gene encoding a second reporter protein, capable of generating a second signal, and
  iii. optionally, a first reporter gene comprising a gene encoding a first reporter protein, capable of generating a first signal, and
b) expressing the target gene library in a plurality of host cells described herein above, and
c) providing a pharmacoperone and contacting it with said plurality of host cells,
d) sorting the cells into at least two populations on the basis of the second and optionally of the first signal,
e) isolating the vectors comprised in the cells at least one of of the sorted populations, and
f) identifying the sequence of the target genes comprised within said isolated vectors, thereby identifying the proteins for which proper folding is restored by the pharmacoperone.

The target gene library may be a library of mutants of one protein, in which case the above method can be used to test the activity of a pharmacoperone on different mutants. In particular, the library may be a part of a library obtained after sorting the cells where the target proteins misfold, so that the library only comprises misfolded proteins.

For example, in one embodiment, the cell population is sorted to obtain a first population comprising vectors encoding proteins toward which the pharmacoperone is capable of restoring proper folding, and a second population comprising vectors encoding proteins toward which the pharmacoperone is not capable of restoring proper folding.

Such methods can be performed in a high-throughput manner.

The method may be adapted to identify the proteins for which the molecule being tested as pharmacoperone is not capable of restoring proper folding, if this is desirable.

A Method for Enriching a Cell Population

The present systems may also be useful for enriching a cell population for cells having certain characteristics, in particular:
- cells where the proteins are expressed in a soluble form and fully translated;
- cells where the proteins are expressed in an insoluble form, e.g. as inclusion bodies, and fully translated;
- cells where the proteins are expressed in a soluble form and not fully translated;
- cells where the proteins are expressed in an insoluble form, e.g. as inclusion bodies, and not fully translated,
- cells that express increased amounts of a target protein that is correctly folded compared to the original cell population,
- cells that express increased amounts of a target protein that is expressed in an insoluble form, e.g. as inclusion bodies, and fully translated.

In some instances, it may be desirable to sort cells as described above, where the desired population comprises the cells that are able to express the protein encoded by the target gene in a soluble form.

However, the desired population may also in some embodiments comprise the cells that are able to express the protein encoded by the target gene in an insoluble form, and particularly as inclusion bodies (Ramon et al., 2014). Inclusion bodies often contain relatively pure target protein, which may facilitate the purification process. Methods for purifying inclusion bodies and the proteins comprised therein followed by subsequent refolding of the proteins are known in the art. The inclusion bodies can for example be isolated by solid/liquid separation. Inclusion bodies are often solubilized using high concentration (6-8 M) of chaotropes like urea and guanidine hydrochloride. After solubilisation, the native proteins can for example be refolded in vitro by removal of the chaotropic agents and other salts by dialysis or dilution of the solubilized protein directly into the renaturation buffer (Rudolph et al., 1996; Singh et al., 2015).

A Method of Assessing Target Gene Product Inclusion Body Formation

Yet an aspect of the present invention concerns a method of assessing target gene product solubility in a target gene library to identify library members that express target genes with altered target gene product solubility and/or folding, the method comprising the steps of
  a) providing a target gene library comprising a plurality of vectors comprising the system described herein above each comprising
    i) a target gene described herein above, and
    ii) a second reporter gene comprising a gene encoding a second reporter protein described herein, capable of generating a second signal, and
  b) expressing the target gene library in a plurality of host cells described herein above, and
  c) determining the second signal using analysis means as described herein above, and
  d) assessing the target gene product solubility on the basis of the second signal, wherein the assessment is conducted by comparison to appropriate control host cells.

In some embodiments, the second reporter protein is a fluorescent protein.

In an embodiment of the present invention concerns a method of assessing target gene product solubility in a target gene library, the method comprising the steps of
  a) providing a target gene library comprising a plurality of vectors comprising the system described herein above each comprising
    i) a target gene described herein above, and
    ii) a second reporter gene comprising a gene encoding a second reporter protein capable of generating a second signal as described herein, capable of generating a second signal, and
  b) expressing the target gene library in a plurality of host cells described herein above, and
  c) determining the second signal using analysis means as described herein above, and
  d) assessing the target gene product solubility on the basis of the second signal, wherein the assessment is conducted by comparison to appropriate control host cells.

A Method of Assessing Effects of Growth Conditions on Folding

Another aspect of the present invention concerns a method of assessing the effect of host cell growth conditions on the target gene product solubility and/or folding, comprising the steps of:
  a) providing the inclusion body responsive reporter system described herein above comprising
    i) a target gene described herein above, and
    ii) a second reporter gene comprising a gene encoding a second reporter protein described herein, capable of generating a second signal, and
  b) expressing the inclusion body responsive reporter system in a host cell described herein above under various growth conditions, and
  c) determining the second signal using analysis means as described herein above, and
  d) assessing the target gene product solubility on the basis of the second signal, wherein the assessment is conducted by comparison to appropriate control host cells.

In some embodiments, the second reporter protein is a fluorescent protein.

Method of Developing a Target Gene Product Solubility Prediction Algorithm

A further aspect of the present invention relates to a method of developing a target gene product solubility prediction algorithm, comprising the steps of:
  a) providing a target gene library comprising a plurality of vectors comprising the inclusion body responsive reporter system described herein above each comprising
    i) a target gene described herein above, and
    ii) a second reporter gene comprising a gene encoding a second protein described herein, capable of generating a second signal, and
  b) expressing the target gene library in a plurality of host cells described herein above and
  c) determining the second signal using analysis means as described herein above, and
  d) assessing the target gene product solubility on the basis of the second signal, wherein the assessment is conducted by comparison to appropriate control host cells, and e) optionally obtaining the polynucleotide sequence of the target gene of the assessed host cells described herein above, and f) developing a target gene product solubility prediction algorithm described herein above.

In one embodiment, the second protein is a fluorescent protein. In another embodiment, the second protein is a protein involved in antibiotics resistance.

Another aspect of the present invention relates to a protein folding prediction algorithm developed using the method of developing a target gene product solubility prediction algorithm described herein above or the inclusion body responsive reporter system described herein above.

EXAMPLES

Example 1—Construction of a Fluorescence Based Protein Folding Reporter

This example demonstrates the construction of a fluorescence-based system for reporting on protein misfolding at the single cell level. Both a stable and a destabilized variant of GFP were fused to a chaperone promoter, and the system was tested using heat shock experiment.

For construction of a protein folding sensor that reports on the formation of inclusion bodies (IB), the IbpA promoter (SEQ ID NO: 1) from *E. coli* MG1655 was fused to a destabilized version of GFP (GFP-ASV; SEQ ID NO: 2), and a stable GFP (GFP-mut3; SEQ ID NO: 3), respectively. The GFP-ASV and GFP-mut3 were amplified by polymerase chain reaction (PCR) using the primer pair and template indicated in table 1. The PCR products were cloned into pSEVA441 (GenBank: JX560339.1) using the XbaI and SpeI restriction sites, resulting in either pSEVA441-GFP-ASV (FIG. 6b) or pSEVA441-GFP-mut3. The *E. coli* IbpA promoter was amplified by PCR (Table 1) and cloned via the PacI and XbaI restriction sites into pSEVA441-GFP-ASV or pSEVA441-GFP-mut3, respectively. The resulting final plasmids were named pSEVA441-IbpAp-GFP-ASV and pSEVA441-IbpAp-GFP-mut3. To generate pSEVA631(Sp)-IbpAp-GFP-ASV (FIG. 6a) and pSEVA631(Sp)-IbpAp-GFP-mut3 (FIG. 6a), respectively, the IbpAp-GFP reporter gene was cut with PacI and SpeI and subcloned into the pSEVA631 (GenBank: JX560348.1). Finally, the gentamycin cassette of pSEVA631 was replaced by the spectinomycin cassette of pSEVA441 using the SpeI and PshAI retriction sites. To analyze the impact of inclusion body (IB) formation on activity of the different IbpAp-GFP variants, pSEVA631(Sp)-IbpAp-GFP-ASV or pSEVA631(Sp)-IbpAp-GFP-mut3 were co-transformed with pET22b in *E. coli* Rosetta2™ (DE3)pLysS (Novagen®).

Transformants were selected on LB plates containing 25 μg/mL chloramphenicol, 50 μg/mL spectinomycin, and 100 μg/mL ampicillin. Single clones were inoculated in LB medium supplemented with the corresponding antibiotics and grown at 37° C. and 300 rpm to an $OD_{600}$ of 0.5. IB formation in *E. coli* was induced by performing a heat-shock for 10 min at 42° C. After heat shock, the cells were grown for an additional 2.5 hours at 37° C. and 300 rpm. Induction of the IbpA promoter by IBs in single cells was monitored over time by changes of the GFP signal using flow cytometry (Instrument: BD FACS-Aria™ SORP cell sorter; Laser: 488 nm; >50 mW; Filter: 505LP, 515/20-nm FITC). As a control, the GFP signal in un-induced cells was monitored at each time point. All measurements were performed in triplicates. For data analysis the GFP (FITC-A, X-mean) values at each time point were normalized to the corresponding background GFP signal.

As shown in FIG. 1, both IpbAp-GFP reporter gene constructs are activated by heat-shock-induced protein aggregation, reaching a maximum of activation 20 min after heat shock. However, the fluorescent signal after the heat shock response of IbpAp-ASV was two-fold higher compared to IbpAp-mut3. The data demonstrate that the sensitivity of the sensor can be significantly increased by using a destabilized version of GFP.

TABLE 1

Overview of primer pairs and templates used in the examples

| Name | Primer pair (table 1a) | Template |
|---|---|---|
| GFP-ASV | GFP-fwd<br>GFP-ASV-rev | pJBA120<br>(Andersen et al. 1998, 2240-2246) |
| GFP-mut3 | GFP-fwd<br>GFP-mut3-rev | pJBA28<br>(Andersen et al. 1998, 2240-2246) |
| IbpAp | IbpAp-fwd<br>IbpAp-rev | genomic DNA of *E. coli* MG1655 |
| mCherry | mCherry-fwd<br>mCherry-rev | synthetic DNA (codon optimized for *E. coli*) |
| PARP1-BRCT | PARP1-BRCT-fwd<br>PARP1-BRCT-fwd | pCMV-SPORT6-PARP1 (Orfeome) |
| BRCA1-BRCT | BRCA-BRCT-fwd<br>BRCA-BRCT-rev-1 | pCR-BluntII-TOPO-Q1RMC1 (Orfeome) |
| BRCA1-BRCT-STOP | BRCA-BRCT-fwd<br>BRCA-BRCT-STOP-rev | pCR-BluntII-TOPO-Q1RMC1 (Orfeome) |
| BRCA1-BRCT-truncated | BRCA-BRCT-fwd<br>BRCA-BRCT-rev-2 | pCR-BluntII-TOPO-Q1RMC1 (Orfeome) |
| P19 | P19-fwd<br>coupling cassette-rev | synthetic DNA (codon optimized for *E. coli*) |
| E6 | E6-fwd<br>coupling cassette-rev | synthetic DNA |
| NusA | NusA-fwd<br>NusA-rev | genomic DNA of *E. coli* MG1655 |
| SUMO | SUMO-fwd<br>SUMO-rev | synthetic DNA |
| PARP1-BRCT mutant library | Mut-PARP1-BRCT-fwd<br>Mutagenesis-rev | pET22-PARP1-BRCT-trans-mCherry |
| BRCA1-BRCT mutant library | Mutagenesis-fwd<br>Mutagenesis-rev | pET22-BRCA1-BRCT-trans-mCherry |
| PARP1-BRCT-NextGenSeq fragment 1 | Library-seq-fwd<br>PARP1-BRCT-int-rev | Sorted pET22-PARP1-BRCT-trans-mCherry mutant library |
| PARP1-BRCT-NextGenSeq fragment 2 | PARP1-BRCT-int-fwd<br>Library-seq-rev | Sorted pET22-PARP1-BRCT-trans-mCherry mutant library |

TABLE 1a

Primers

| Primer name | Primer sequence (5'-3') |
|---|---|
| GFP-fwd | SEQ ID No: 25 |
| GFP-ASV-rev | SEQ ID No: 26 |
| GFP-mut3-rev | SEQ ID No: 27 |
| IbpAp-fwd | SEQ ID No: 28 |
| IbpAp-rev | SEQ ID No: 29 |
| mCherry-fwd | SEQ ID No: 30 |
| mCherry-rev | SEQ ID No: 31 |
| BRCA-BRCT-fwd | SEQ ID No: 32 |
| BRCA-BRCT-rev-1 | SEQ ID No: 33 |
| BRCA-BRCT-rev-2 | SEQ ID No: 34 |
| BRCA1-BRCT-STOP-rev | SEQ ID No: 35 |

TABLE 1a-continued

Primers

| Primer name | Primer sequence (5'-3') |
| --- | --- |
| PARP1-BRCT-fwd | SEQ ID No: 36 |
| PARP1-BRCT-rev | SEQ ID No: 37 |
| E6-fwd | SEQ ID No: 38 |
| P19-fwd | SEQ ID No: 39 |
| coupling cassette-rev | SEQ ID No: 40 |
| NusA-fwd | SEQ ID No: 41 |
| NusA-rev | SEQ ID No: 42 |
| SUMO-fwd | SEQ ID No: 43 |
| SUMO-rev | SEQ ID No: 44 |
| Mut-PARP1-BRCT-fwd | SEQ ID No: 45 |
| Mutagenesis-fwd | SEQ ID No: 46 |
| Mutagenesis-rev | SEQ ID No: 47 |
| Library-seq-fwd | SEQ ID No: 48 |
| PARP1-BRCT-int-rev | SEQ ID No: 49 |
| PARP1-BRCT-int-fwd | SEQ ID No: 50 |
| Library-seq-rev | SEQ ID No: 51 |

Example 2—Dual Reporter System for Monitoring Recombinant Protein Expression and Folding in *E. coli*

This example demonstrates the creation of a dual reporter system that enables analysis of both protein expression and protein folding at the single cell level. The functional system was used to screen the effect of various protein expression and folding tags. The protein folding sensor system described in example 1 was combined with a translation sensor, which determines if a target enzyme is fully translated (Mendez-Perez et al. 2012, 298-305). Here, the translation of the target protein results in the translation of mCherry that is used as reporter. The recombinant protein as well as the reporter gene is located on one single mRNA that forms a secondary structure (translation-coupling cassette) in the absence of recombinant protein translation. If translation of the target protein is successful, the secondary structure of the mRNA is changed, a ribosomal binding site upstream of the mCherry coding sequence is released and the fluorescent reporter protein is translated. Thus, expression of the protein of interest can be monitored by changes in the mCherry signal.

A set of proteins, which are known to have different folding properties in *E. coli*, were fused to the translation coupling cassette (SEQ ID No: 4) followed by mCherry (SEQ ID No: 5). The BRCT-domain of human Poly [ADP-ribose] polymerase 1 (PARP1, SEQ ID No: 6), the BRCT-domain of human breast cancer 1, early onset (BRCA-1, SEQ ID No: 7, SEQ ID No: 9), the human cyclin-dependent kinase 4 inhibitor D (p19, SEQ ID No: 10) and protein E6 from human papillomavirus type 16 (SEQ ID No: 11) were amplified by PCR using the primers and templates as indicated in table 1. Additionally, mCherry was amplified by PCR (see table 1). Each human protein was assembled with mCherry and pET22b (Novagen), which has been digested with NdeI and Hind III, using Gibson reaction (New England Biolabs). The resulting expression vectors (listed in table 2) comprise the coding sequence of the respective human protein, which is linked via a C-terminal translation coupling cassette (Mendez-Perez et al. 2012, 298-305), to the open reading frame (ORF) of mCherry. p19 was fused with two additional N-terminal protein tags, NusA (SEQ ID No: 12) and SUMO (SEQ ID No: 13) which are both known to improve folding of various proteins (Butt et al. 2005, 1-9; Davis et al. 1999, 382-388). For cloning, NusA and SUMO were amplified by PCR using the primers indicated in table 1 and inserted into pET22-P19-trans-mCherry via the NdeI restriction site. The final protein expression reporter plasmids are listed in table 2.

To analyze the combined reporter system, pSEVA631 (Sp)-IbpAp-GFP-ASV and the protein expression reporter plasmids (table 2) were co-transformed into chemically competent *E. coli* Rosetta2™(DE3)pLysS (Novagen®). Transformants were selected on LB plates containing 25 µg/mL chloramphenicol, 50 µg/mL spectinomycin, and 100 µg/mL ampicilin. Single clones were grown in LB medium (supplemented with the corresponding antibiotics) at 37° C. and 300 rpm to an $OD_{600}$ of 0.5-0.7 and expression of the human proteins was induced by addition of 0.5 mM IPTG. Directly after induction, the growth temperature was changed to 30° C. Protein expression and folding was analyzed 1 h after induction using flow cytometry (Instrument: BD FACS-Aria™ SORP cell sorter; Laser 1: 488 nm: >50 mW, Filter: 505LP, 515/20-nm FITC; Laser 2: 561 nm: >50 mW; Filter: 600LP, 610/20-nm PE-Texas Red®). A minimum of five independent samples were analyzed for each plasmid combination. For data analysis, the GFP (FITC-A, X-mean) signal as well as the mCherry signal (PE-Texas Red-A, X-mean) was normalized to the corresponding PARP1-BRCT signal. The intracellular localization of the proteins was further analyzed by fractionated cell disruption. Here, cells (1 mL) were harvested either 1 h (for immunoblot analysis) or 3 h (for InstantBlue staining) after induction of protein expression. The cell pellet was resuspended in 50 µL Buffer A (20 mM Tris/HCl pH7.5, 150 mM NaCl; 10 mM EDTA, 1×HP-protease inhibitor mix (Serva)) and cells were broken by repeating cycles of freeze and thaw. The broken cells were incubated for 20 min on ice. Afterwards, the cells were resuspended in Buffer B (20 mM Tris/HCl pH7.5, 150 mM NaCl, 10 mM EDTA, 50 mM $MgCl_2$, 1×HP-protease inhibitor mix (Serva)) to a final $OD_{600}$ of 5 and supplemented with benzonase (20 units/ml; Merck). After 20 min incubation on ice, cells were spun-down for 1 min at 500×g to remove the cell debris. The supernatant containing all soluble and insoluble proteins was transferred to a fresh reaction tube. An aliquot of the supernatant was taken, representing the total protein fraction (total). The remaining cell lysate was spun-down twice for 15 min at 20000×g and the supernatant containing all soluble proteins was transferred into a new reaction tube (sol). The isolated fractions were separated on SDS-PAGE (RunBlue 4-20%, Expedeon; NuPAGE® Bis-Tris gel 4-12%, Invitrogen) and analyzed by InstantBlue staining (Expedeon) and quantitative immunoblotting using an anti-His antibody (Novagen).

Figure 2A:
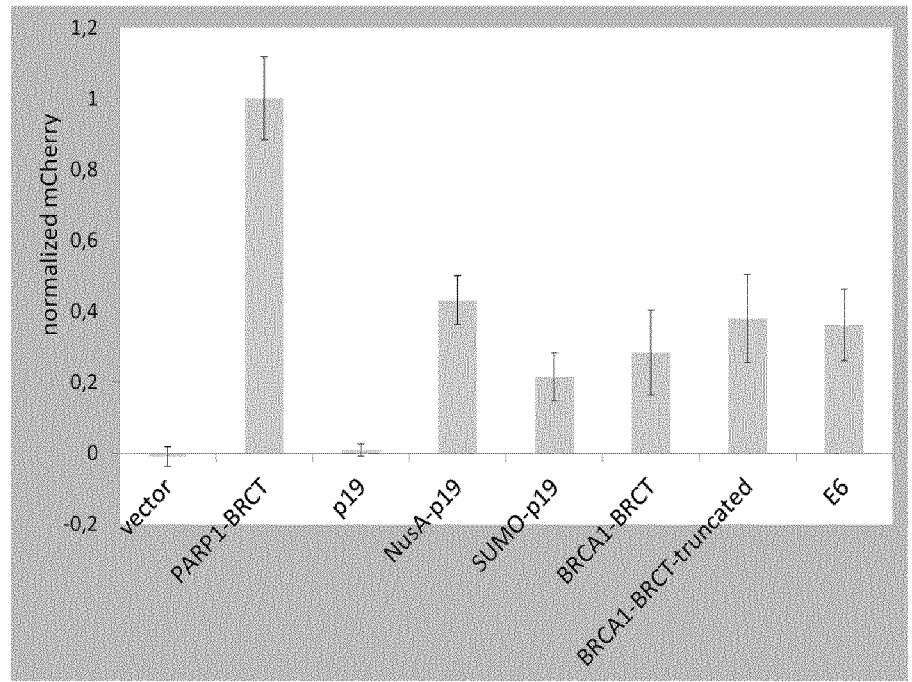
Figure 2B:
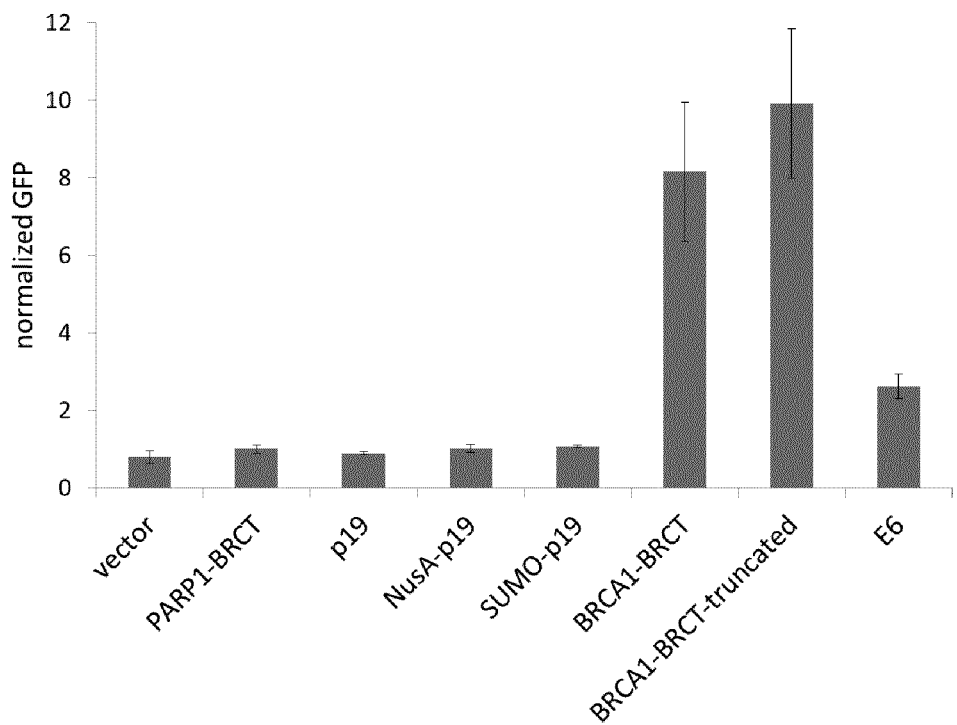
Figure 2C:
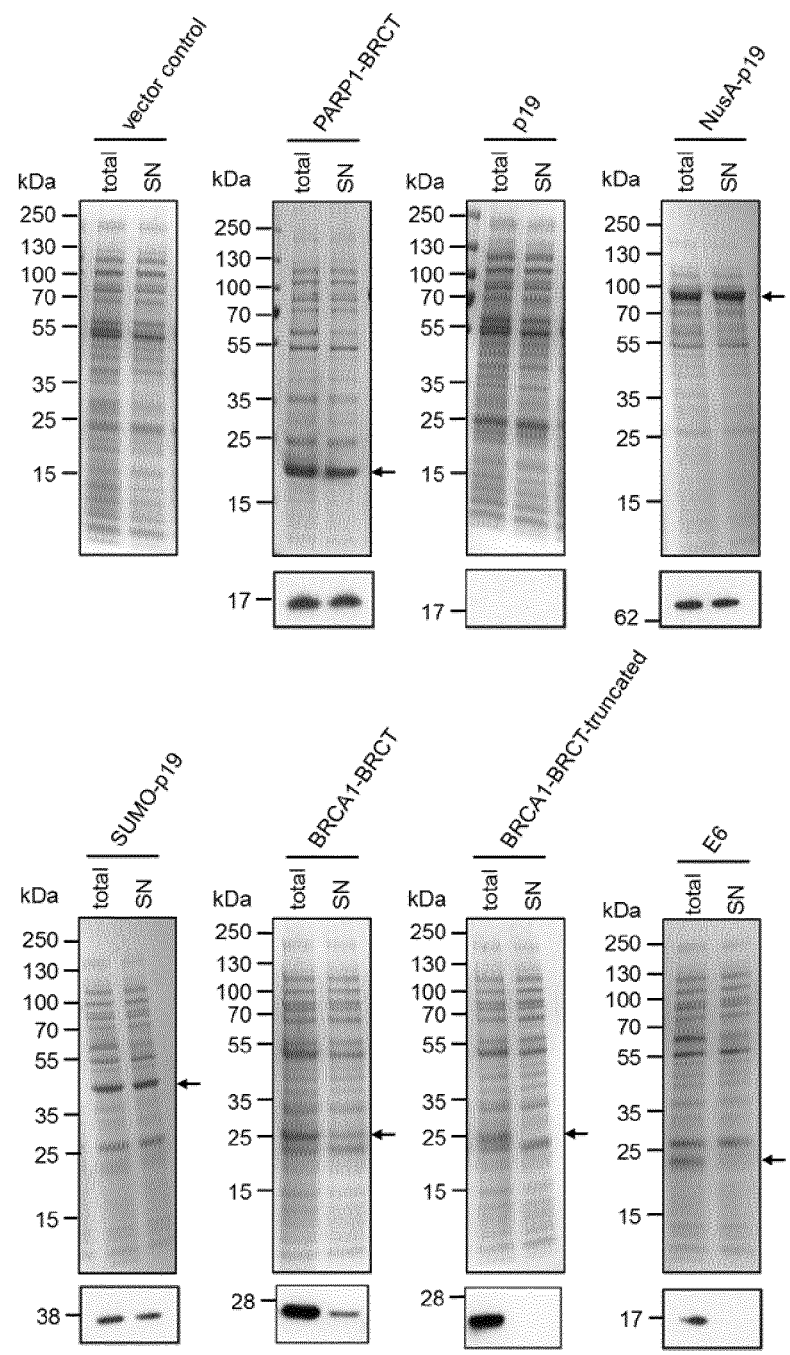

As shown in FIG. 2A & FIG. 2B, the PARP1-BRCT-domain is expressed and correctly folded in *E. coli* as indicated by a background GFP level and an increased mCherry signal. The protein, p19, is only expressed when a solubility tag (NusA or SUMO) is fused to the N-terminus of the protein. However, both tagged p19 versions were found to be properly folded. Both BRCA-BRCT variants as well as the protein E6 were expressed in *E. coli*, but expression resulted in an increased GFP signal, suggesting that the proteins aggregate and are stored in inclusion bodies. The results of the combined sensor system could be verified by analysis of the subcellular protein localization using fractionated cell disruption (FIG. 2C), demonstrating that the combined sensor system is functional.

TABLE 2

Overview of plasmids used for co-transformation
in Rosetta2(DE3)pLysS (FIG. 6).

| Plasmid 1 (protein folding sensor) | Plasmid 2 (protein expression reporter plasmid) |
|---|---|
| pSEVA631(Sp)-IbpAp-GFP-ASV | pET22b |
| pSEVA631(Sp)-IbpAp-GFP-ASV | pET22-PARP1-BRCT-trans-mCherry |
| pSEVA631(Sp)-IbpAp-GFP-ASV | pET22-p19-trans-mCherry |
| pSEVA631(Sp)-IbpAp-GFP-ASV | pET22-NusA-p19-trans-mCherry |
| pSEVA631(Sp)-IbpAp-GFP-ASV | pET22-SUMO-p19-trans-mCherry |
| pSEVA631(Sp)-IbpAp-GFP-ASV | pET22-BRCA1-BRCT-trans-mCherry |
| pSEVA631(Sp)-IbpAp-GFP-ASV | pET22-BRCA1-BRCT-truncated-trans-mCherry |
| pSEVA631(Sp)-IbpAp-GFP-ASV | pET22-E6-trans-mCherry |

Example 3—Impact of the Plasmid Backbone on the Sensitivity of the Protein Folding Sensor This example demonstrates that plasmid backbone impacts the functionality of the folding reporter system.

To analyze the impact of the vector backbone on IbpAp-GFP-ASV activity, pSEVA 631(Sp)-IbpAp-GFP-ASV (pBBR1 origin) and pSEVA441-IbpAp-GFP-ASV (ColE1 origin) (for construction see Example 1), respectively, were co-transformed with pET22b in E. coli Rosetta2™ (DE3) pLysS (Novagen®). Transformants were selected on LB plates containing 25 µg/mL chloramphenicol, 100 µg/mL ampicillin, and 50 µg/mL spectinomycin. Single clones were inoculated in LB medium supplemented with the corresponding antibiotics and grown at 37° C. and 300 rpm to an $OD_{600}$ of 0.5. Protein aggregation in E. coli was induced by performing a heat-shock for 10 min at 42° C. After heat shock, cells were grown at 37° C. and 300 rpm. Induction of the IbpA promoter by IBs in single cells was monitored after 40 min by changes of the GFP signal using flow cytometry (Instrument: BD FACS-Aria™ SORP cell sorter; Laser: 488 nm: >50 mW; Filter: 505LP, 515/20-nm FITC). As a control, the GFP signal in un-induced cells was monitored.

Figure 3A:
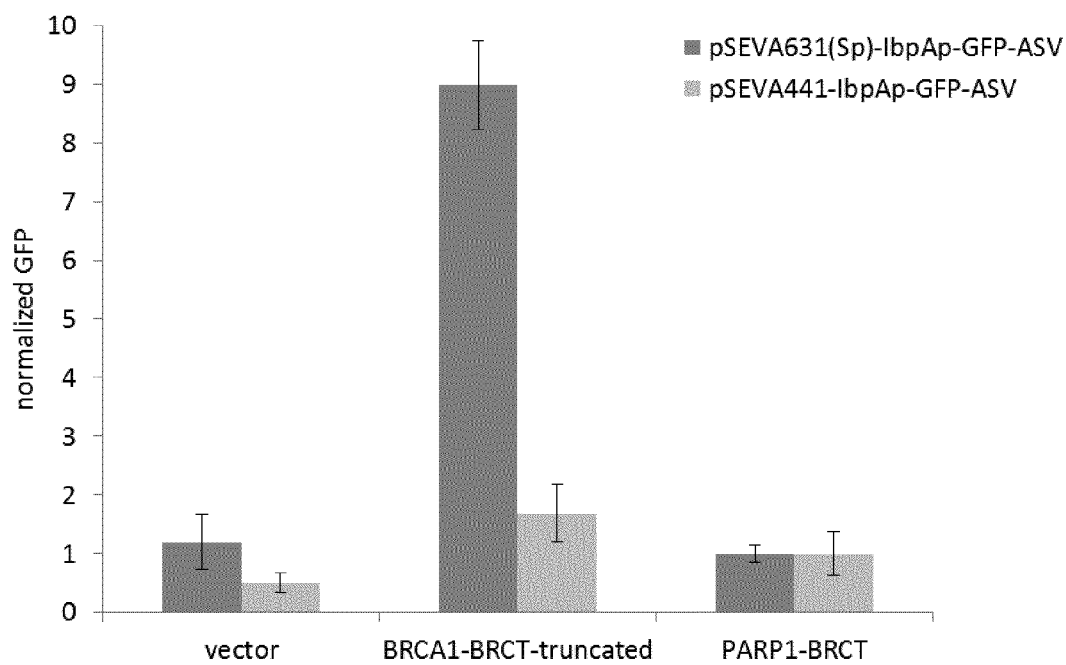
Figure 3B:
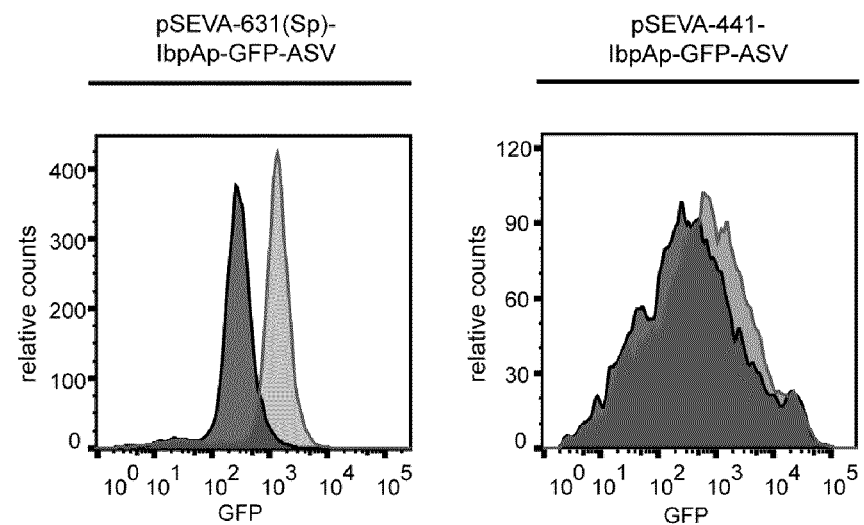

As shown in FIG. 3b pSEVA631(Sp)-IbpAp-GFP-ASV and pSEVA441-IbpAp-GFP-ASV are induced by heat shock, demonstrated by an increased GFP signal. However, the shift of the GFP signal is much more pronounced when the reporter gene is located on a plasmid backbone harboring the pBBR1 origin. In case of pSEVA441-IbpAp-GFP-ASV the E. coli population shows already a broad distribution of GFP levels in the untreated control cells, thus the sensitivity of the reporter gene is much lower compared to the pSEVA631(Sp)-IbpAp-GFP-ASV. The data suggests, that the copy number and origin of the plasmid can help achieve a low background GFP-level and a good signal to noise ratio.

To further investigate the impact of the plasmid backbone on the sensitivity of the IbpAp-GFP reporter gene, pSEVA631(Sp)-IbpAp-GFP-ASV and pSEVA441-IbpAp-GFP-ASV, respectively, were co-transformed with either pET22b, pET22-PARP1-BRCT-trans-mCherry or pET22-BRCA1-BRCT-trans-mCherry into E. coli Rosetta2™ (DE3)pLysS (Novagen®). Transformants were selected on LB plates containing 25 µg/mL chloramphenicol, 50 µg/mL spectinomycin, and 100 µg/mL ampicillin. Single clones were grown at 37° C. and 300 rpm in LB medium supplemented with the corresponding antibiotics. At $OD_{600}$ of 0.5-0.7 the expression of the human proteins was induced by addition of 0.5 mM IPTG. Directly after induction the growth temperature was changed to 30° C. Induction of the IbpAp-GFPs by misfolding of proteins was analyzed 1 h after induction using flow cytometry (Instrument: BD FACS-Aria™ SORP cell sorter; Laser: 488 nm: >50 mW; Filter: 505LP, 515/20-nm FITC). All measurements were performed with n=3 (FIG. 3a) and n≥3 (FIG. 3c), respectively. For data analysis the GFP-signal (FITC-A, X-mean) was normalized to the respective GFP-signal of PARP1-BRCT (FIG. 3a) or the vector control (FIG. 3c).

Figure 3C:
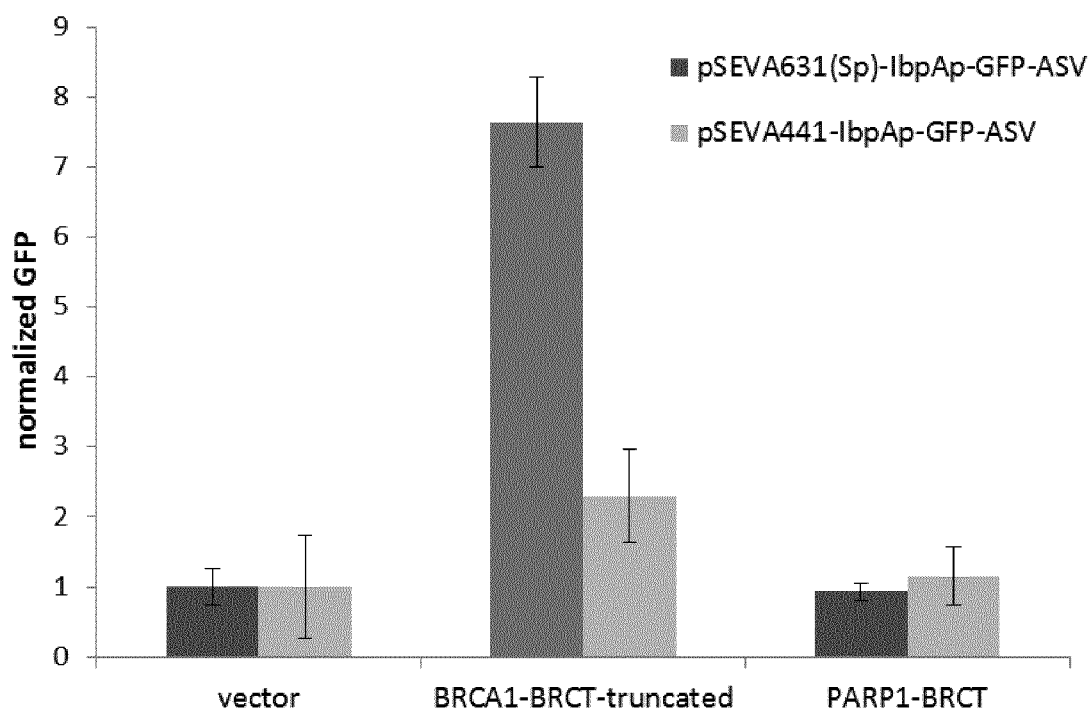

As shown in FIG. 3a and FIG. 3c, misfolding of BRCA1-BRCT causes a 9-fold increase of the GFP signal compared to the background signal if pSEVA631(Sp) is used as plasmid backbone. In comparison the GFP signal was only 2-fold increased, when the IbpAp-GFP-ASV was located on pSEVA441, demonstrating that sensitivity of the folding sensor is strongly affected by the plasmid backbone.

Example 4—High-throughput Screening and Next Generation Sequencing of Protein Mutant Libraries This example demonstrates how the dual reporter system for protein folding and expression can be used for screening large libraries of random protein mutants. By sorting and sequencing subsets of protein mutant libraries with different folding properties, this example demonstrated how it is possible to determine mutations and amino acid positions that are important for protein expression and folding.

The protein expression and folding system was used to screen for PARP1-BRCT protein variants with altered folding properties, which was further characterized by next generation sequencing. The PARP1-BRCT domain was randomly mutated, aiming at a mutation rate of 1 to 3 mutations per construct, using the GeneMorph II random mutagenesis kit (Agilent) according to manufacturer's instructions. Primers and templates used for the reactions are indicated in table 1. A megawhop reaction was performed with the random mutated PCR product as megaprimer and pET22-PARP1-BRCT-trans-mCherry as template. The resulting linear DNA fragment was transformed into MegaX DH10B™ T1R Electrocomp™ cells (Invitrogen) and transformants were selected on LB plates supplemented with 100 µg/mL ampicillin. The colonies (library size >100000) were pooled from the plates and the plasmids were directly purified without further growing of the culture.

The vectors pET22b, pET22-PARP1-BRCT-trans-mCherry and the created pET22-PARP1-BRCT-trans-mCherry mutant library were transformed into electro-competent Rosetta2(DE3)pLysS cells harboring the protein folding sensor (pSEVA631(Sp)-IbpAp-GFP-ASV). After recovery, the transformants were directly inoculated into 2 mL LB medium containing 20 µg/mL chloramphenicol, 50 µg/mL spectinomycin, 100 µg/mL ampicillin, and grown overnight at 37° C. and 300 rpm. Cells were transferred into fresh medium and grown at 37° C. and 300 to an $OD_{600}$ of 0.5-0.7. Expression of the human proteins was induced by addition of 0.5 mM IPTG and the growth temperature of the culture was shifted to 30° C.

1 h after induction cells were analyzed by flow cytometry (Instrument: BD FACS-Aria™ SORP cell sorter; Laser 1: 488 nm: >50 mW, Filter: 505LP, 515/20-nm FITC; Laser 2: 561 nm: >50 mW; Filter: 600LP, 610/20-nm PE-Texas Red®). 150000 cells expressing a PARP1-BRCT mutant protein with increased GFP signal were sorted in 1 mL LB medium supplemented with antibiotics and grown overnight at 37° C. and 300 rpm. To further enrich the E. coli fraction harboring proteins with altered folding properties, protein expression was induced again and cells (150000 events) were sorted as described above.

The following day, the sorted cell population was analyzed 1 hour after induction of protein expression by flow cytometry (Instrument: BD FACS-Aria™ SORP cell sorter; Laser 1: 488 nm: >50 mW, Filter: 505LP, 515/20-nm FITC; Laser 2: 561 nm: >50 mW; Filter: 600LP, 610/20-nm PE-Texas Red®).

To determine the intracellular localization of the proteins, cells were harvested 1 hour after induction and a fractionated cell disruption was performed as described in example 2 with the following changes. The total cell lysate (total) was spun-down for 20 min at 20000×g. The supernatant containing the soluble protein fraction was transferred into a new reaction tube (sol). The remaining pellet containing the inclusion body fraction (IB) was washed and resuspended in buffer B.

The resulting protein fractions were supplemented with SDS-loading dye and analyzed by SDS-PAGE (RunBlue 4-20%, Expedeon) and subsequent immunoblotting using and anti-His antibody (Novagen).

For next generation sequencing, plasmids were isolated from the sorted E. coli population. As control, plasmids were isolated from the PARP1-BRCT mutant library, which was used as starting material for sorting. Two 300 bp DNA fragments were amplified from the PARP1-BRCT library using a high fidelity polymerase and the primers indicated in table 1. The amplified fragments were purified using AMPure XP beads (Beckman Coulter) to remove free primers and primer dimer species. The PCR-products were mixed in a one-to-one ratio.

In the next step, a PCR reaction was performed to attach Illumina sequencing adapters (Nextera XT Index Kit, Illumina) to the DNA fragments. For the reaction a KAPA HiFi HotStart Polymerase (Kapa Biosystems) was used. The resulting PCR products were purified with AMPure beads. The product size of the PCR reaction was verified on a Bioanalyzer DNA 1000 chip and the DNA was quantified using a Qubit® 2.0 Fluorometer. DNA fragments were normalized to 10 nM in 10 mM Tris pH8.5 0.1% Tween 20. In order to reduce the background signal the sample was spiked with 5% Phi-X control DNA (Illumina). The DNA was loaded onto the flow cell provided in the MiSeq Reagent kit v2, subjected to 300 cycles (Illumina), and sequenced on a MiSeq sequencing system.

Figure 4A:
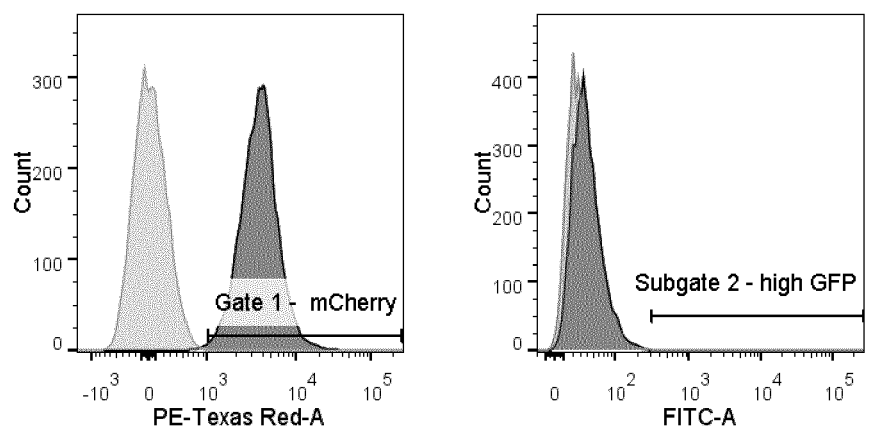
Figure 4B:
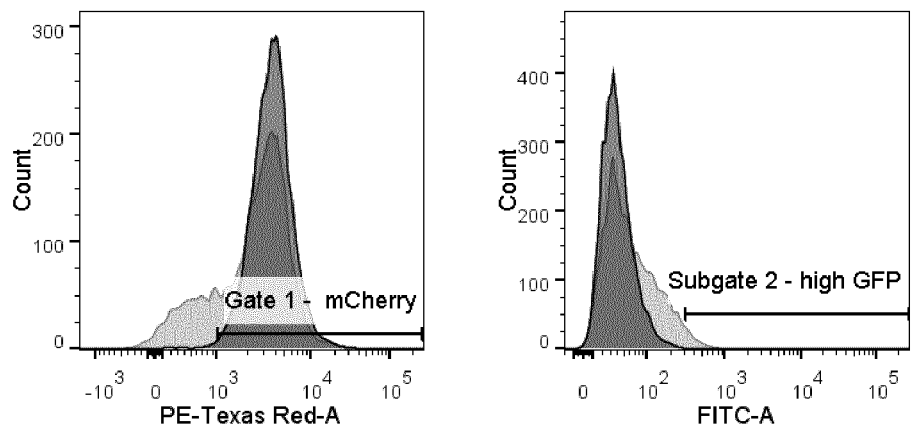

FIG. 4A shows the definition of the gates used for sorting. The first gate includes all cells which have a mCherry signal that is higher than the pET22 background mCherry signal (FIG. 4A left panel, Gate 1). These cells are expected to express the target protein. Gate 2, which is defined as a sub-gate of gate 1, includes all cells with a GFP signal higher than pET22 and PARP1-BRCT background GFP signals (FIG. 4A right panel, Gate 2). Cells in this gate express a protein that aggregates in inclusion bodies. A comparison of the mCherry (left panel) and the GFP (right panel) signal of the PARP1-BRCT mutant library (light grey) and the PARP1-BRCT wild-type construct (dark grey) is displayed in FIG. 4B. 150000 cells of the mutant library which were represented in gate 1 as well as in sub-gate 2 were sorted. Sorting was repeated one day later.

Figure 4C:
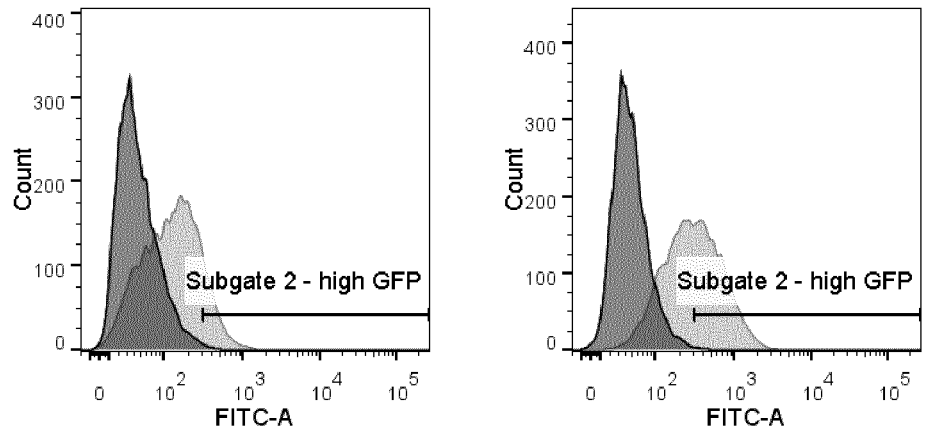

After the second sorting, the protein expression and folding was analyzed again via flow cytometry. As shown in FIG. 4C (left panel), the sorted PARP1-BRCT-population (light grey) shows a significant shift of the GFP signal one hour after induction compared to the wild-type protein (dark grey). This shift is getting larger 2.5 hours after induction (FIG. 4C, right panel), suggesting that PARP1-BRCT-mutant protein variants in the sorted population are insoluble and accumulate in inclusion bodies over time. This observation was verified by fractionated cell disruption and subsequent immunoblotting.

Figure 4D:
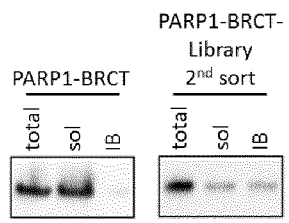

As shown in FIG. 4D, the PARP1-BRCT wild-type protein is exclusively found in the soluble fraction (sol) one hour after induction. In comparison, the sorted E. coli fraction expresses PARP1-BRCT-mutant variants which are partially insoluble.

By using next generation sequencing, the sequences of the sorted PARP1-BRCT mutants were further investigated.

Figure 4E:
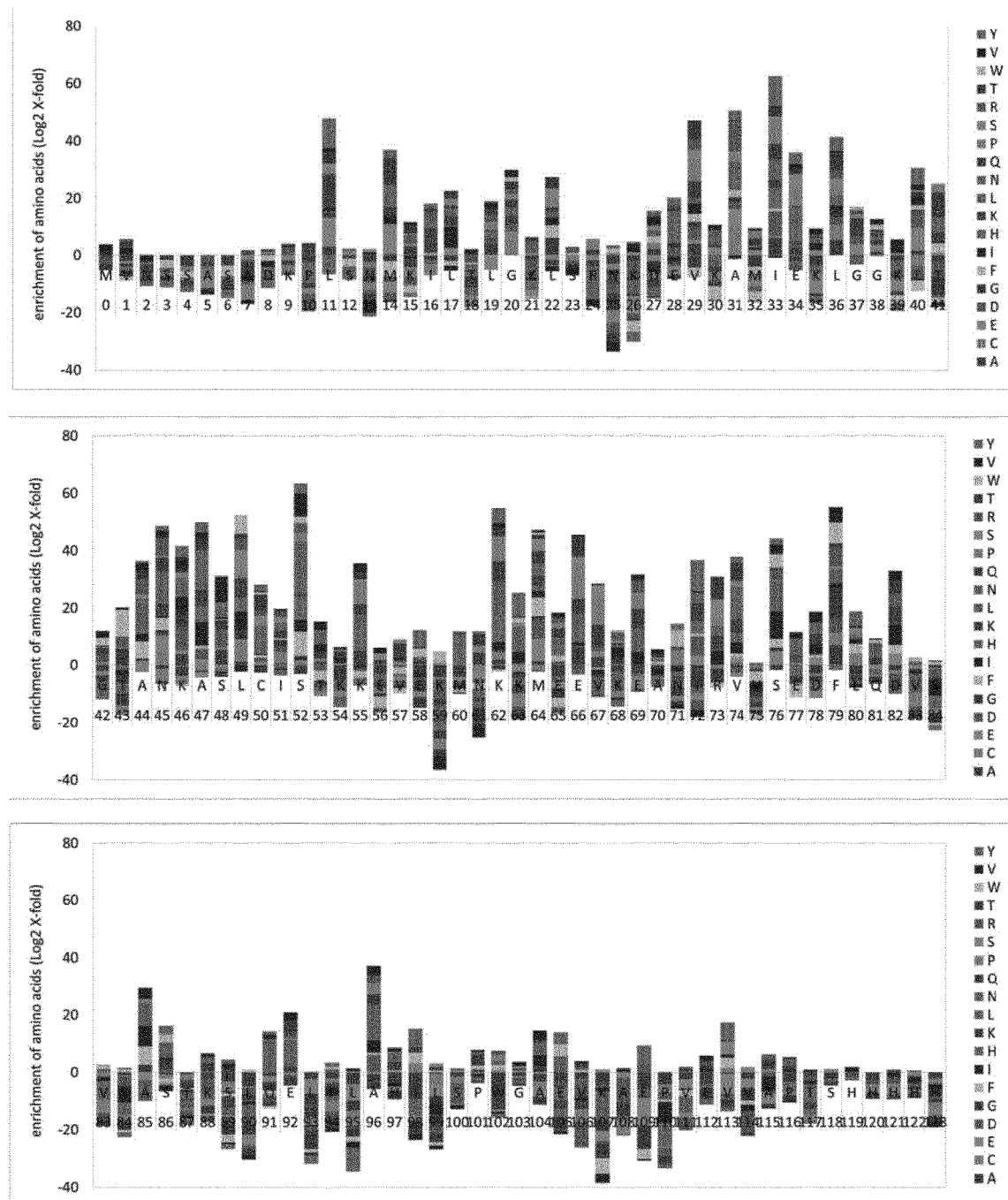
Figure 4F:
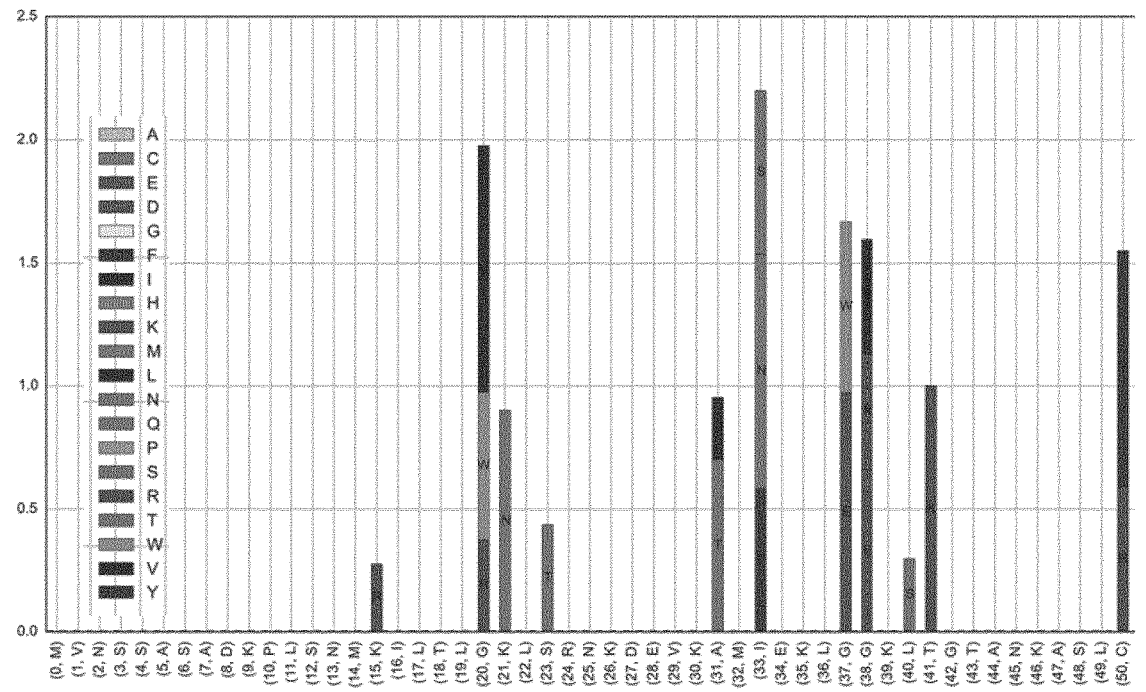
Figure 4F:
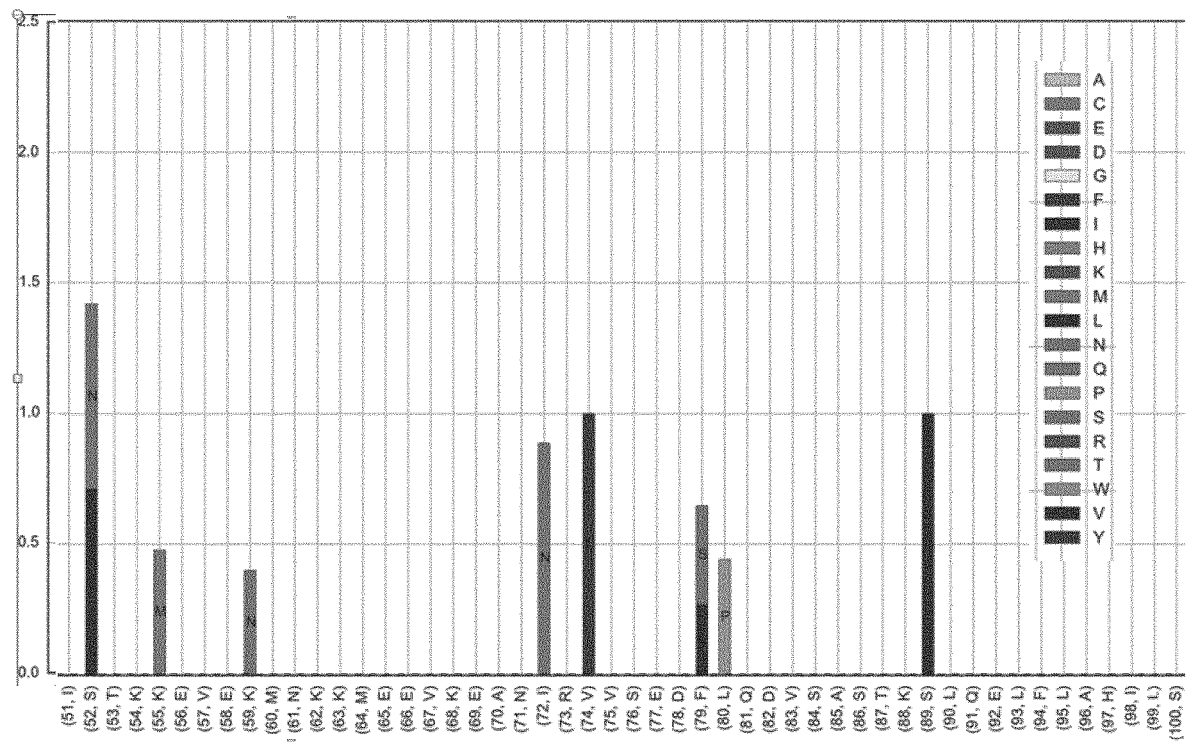
Figure 4F:
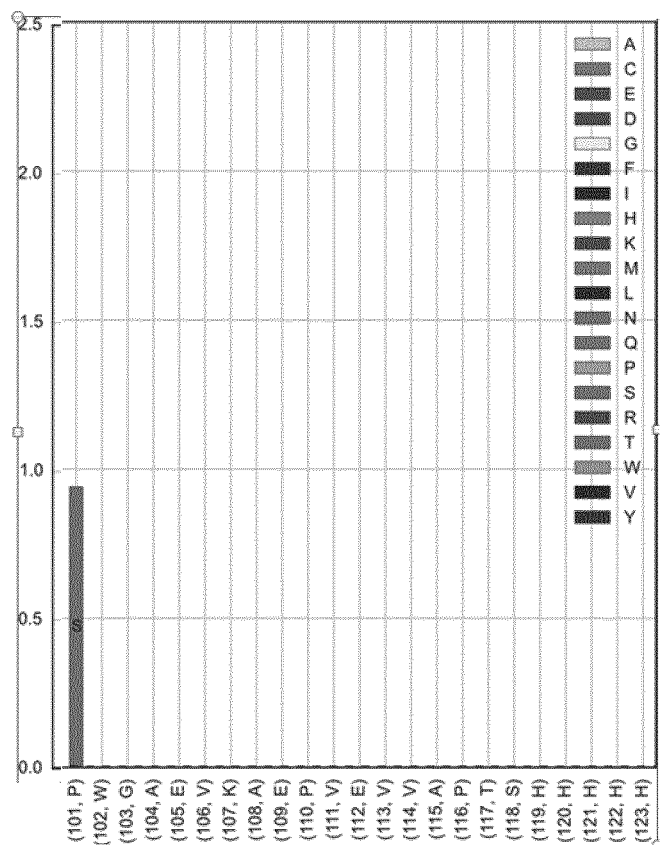

As shown in FIGS. 4E and 4F, the sequencing results provide an overview of amino acids that are enriched or deprived at each individual position of the protein. The enriched amino acids are expected to play a critical role in folding of the PARP1-BRCT domain.

The difference between FIG. 4E and FIG. 4F is only the filtering and processing of the next generation sequencing data. In particular, a python module named Pandas was used for the data analysis depicted in FIG. 4F. Each sequencing dataset was initially normalized by calculating the frequency of each sequence in percent. A threshold (0.003) was introduced in order to remove noise from the deep sequencing data. Enrichment of a certain mutation was calculated by dividing the frequency of the given sequence in the sorted library with the frequency in the control library. Finally, mutations identified in the sorted population, which were not identified in the control library (possibly because it was below the noise filtering threshold), were given an arbitrary value of 100%. This approach ensures an efficient filtering of the data and enables the detection of amino acids important for protein folding.

Altogether, the data shows that the combination of the protein expression and folding sensor enables sorting of proteins with impaired folding properties. The combination of sorting and next generation sequencing can be used as a tool to gain a global understanding of protein folding in general.

Example 5—Improving the Folding Properties of Proteins by Random Mutagenesis

For screening and identification of proteins with improved folding properties, the BRCA1-BRCT domain was randomly mutated. The BRCA1-BRCT domain does not normally fold correctly when expressed in E. coli, and it is therefore of interest to identify variants with improved folding.

Two libraries were constructed using the GeneMorph II random mutagenesis kit (Agilent) according to manufacturer's instructions. Primer and template used for the reaction are indicated in table 1. Library 1 exhibits a mutation rate of 1 to 3 mutations per construct and library 2 a mutation rate of 4-6 mutations per construct. Megawhop reactions were performed with the random mutated PCR products as megaprimer and pET22-BRCA1-BRCT-trans-mCherry as template. The resulting linear DNA fragment was transformed into MegaX DH10B™ T1R Electrocomp™ cells (Invitrogen) and transformants were selected on LB plates supplemented with 100 µg/mL ampicillin. The colonies (library size >100000) were scratched off the plates and the plasmids were directly purified without further growing of the culture.

A BRCA1-BRCT-trans-mCherry version harboring a stop codon in front of the translation cassette (SEQ ID No: 8) was cloned and used as control in the following experiment. For cloning of pET22-BRCA1-BRCT-Stop-trans-mCherry (FIG. 6b) the BRCA1-BRCT domain was amplified using the primer and template as indicated in table 1. The PCR fragment was assembled with mCherry (see Example 2) and pET22b (Novagen), which has been digested with NdeI and HindIII, using Gibson reaction (New England Biolabs).

pET22-BRCA1-BRCT-trans-mCherry, pET22-BRCA1-BRCT-Stop-trans-mCherry, library1 and library 2 were transformed into electro-competent Rosetta2(DE3)pLysS cells harboring the protein folding sensor (pSEVA631(Sp)-IbpAp-GFP-ASV). After recovery, transformants were directly inoculated into 2 mL LB medium containing 25 µg/mL chloramphenicol, 50 µg/mL spectinomycin, 100 µg/mL ampicillin, and grown over night at 37° C. and 300 rpm. Cells were transferred into fresh medium and grown at 37° C. and 300 to an $OD_{600}$ of 0.5-0.7. Expression of the human proteins was induced by addition of 0.5 mM IPTG and the growth temperature of the culture was shifted to 30° C. 1 h after induction cells were analyzed by flow cytometry (Instrument: BD FACS-Aria™ SORP cell sorter; Laser 1: 488 nm: >50 mW, Filter: 505LP, 515/20-nm FITC; Laser 2: 561 nm: >50 mW; Filter: 600LP, 610/20-nm PE-Texas Red®).

Figure 5A:
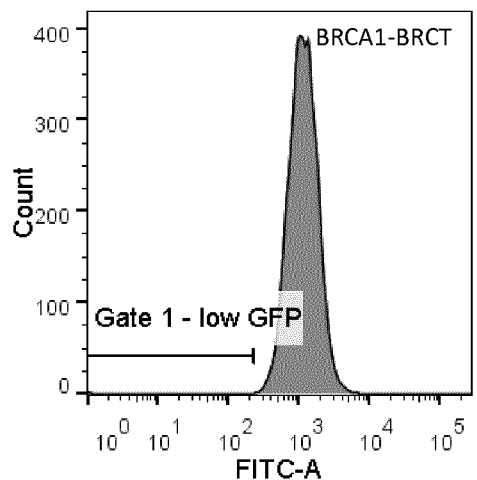
Figure 5B:
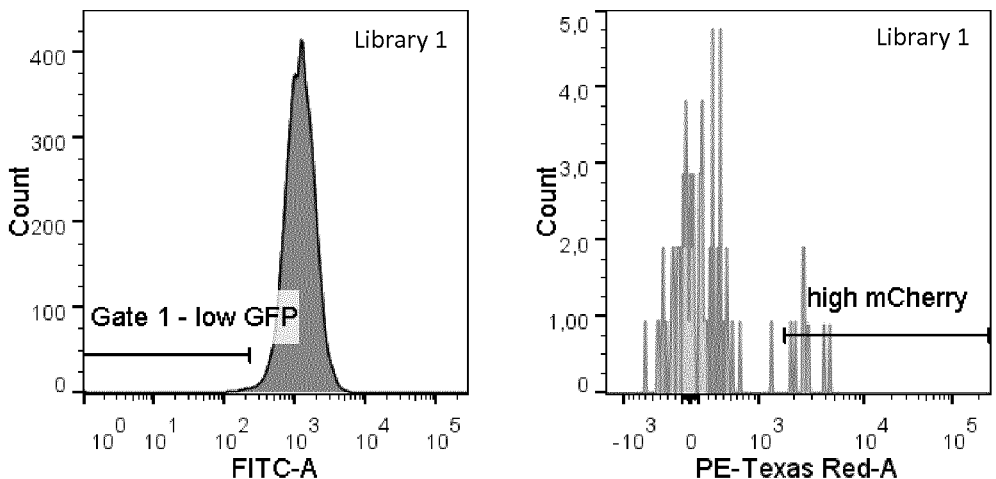
Figure 5C:
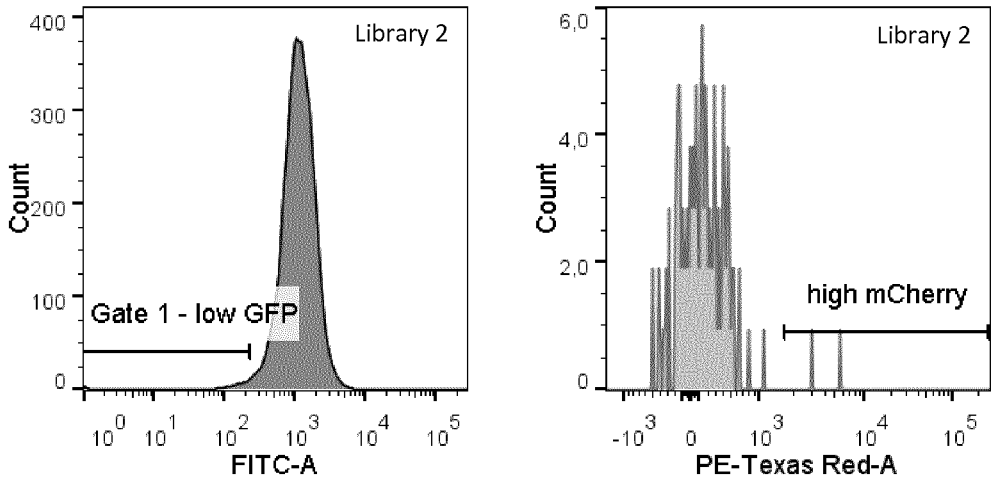

Single cells expressing a BRCA1-BRCT mutant protein with improved folding properties were sorted in 100 µL LB medium supplemented with antibiotics and grown at 37° C. and 300 rpm until they reached stationary phase. Cells were transferred into fresh growth medium and grown to $OD_{600}$ of 0.6. Protein expression was induced by addition of 0.5 mM IPTG and cells were grown for an additional 1 h at 30° C. and 300 rpm. The mCherry and GFP signals were analyzed by flow cytometry (Instrument: BD FACS-Aria™ SORP cell sorter; Laser 1: 488 nm: >50 mW, Filter: 505LP, 515/20-nm FITC; Laser 2: 561 nm: >50 mW; Filter: 600LP, 610/20-nm PE-Texas Red®). FIG. 5A to 5C describes the scenario if only the protein folding sensor is used for sorting of cells that express BRCA1-BRCT mutant proteins with impaired folding properties. In this case the protein translation sensor is not used for determination of the sorting gates. In FIG. 5A a sorting gate is defined including all cells that exhibit a lower GFP signal (FITC-A) than the control cells expressing BRCA1-BRCT. In FIG. 5B (library 1, left panel) and FIG. 5C (library 2, left panel) cells that exhibited a lower GFP-signal than the BRCA1-BRCT expressing control cells were sorted. Analysis of the sorted cells (FIG. 5B & 5C, right panel) showed that the majority of them exhibit diminished mCherry signal, indicating that BRCA1-BRCT is not fully translated in those cells.

Figure 5D:
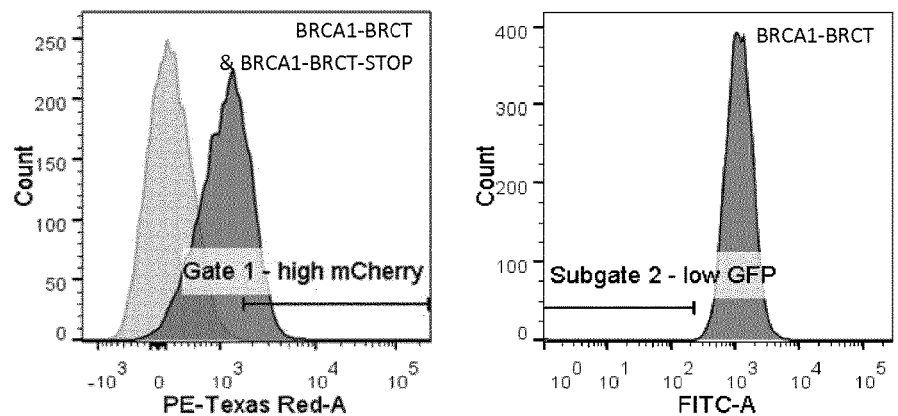
Figure 5E:
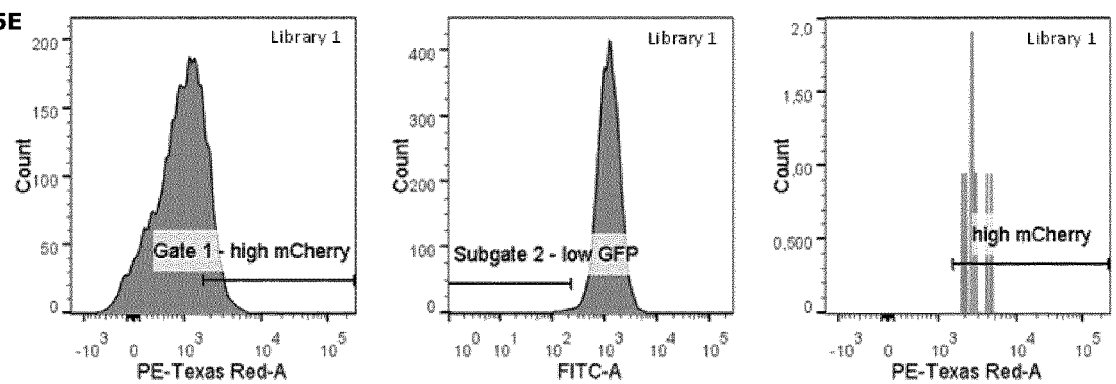
Figure 5F:
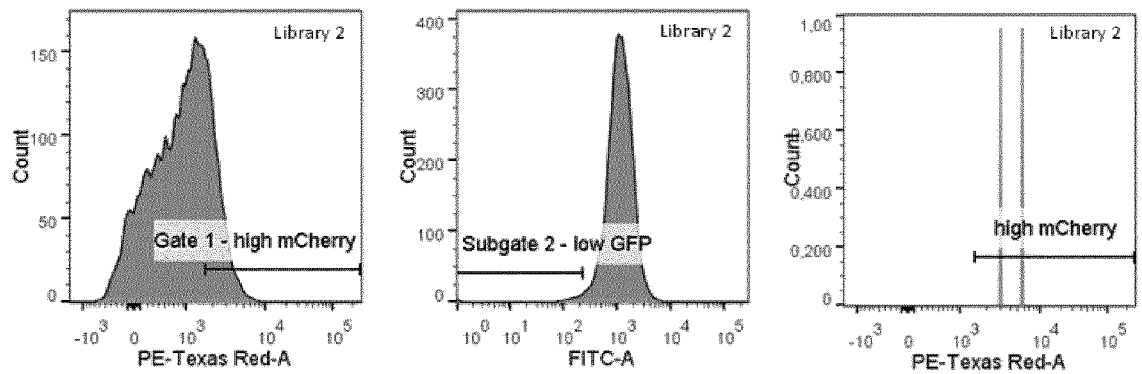

For sorting of BRCA1-BRCT mutants that are expressed and exhibit improved folding properties, two gates were defined by making use of the dual sensor system (FIG. 5D). The left panel shows a comparison of the mCherry signal (PE-Texas Red-A) of pET22-BRCA1-BRCT-trans-mCherry (dark grey) and pET22-BRCA1-BRCT-Stop-trans-mCherry (light grey). Gate 1 includes all constructs that are fully translated, whereas all constructs with a stop-codon upstream of the translation coupling cassette are excluded. Subgate 2 (right panel) comprises all cells that exhibit a lower GFP signal (FITC-A) than BRCA1-BRCT-trans-mCherry. Sorting of mutant BRCA1-BRCT variants with improved folding properties is shown in FIG. 5E (library 1) and 5F (library 2). Only cells included in gate 1 (left panel, FIGS. 5E and 5F) and subgate 2 (middle panel, FIGS. 5E and 5F) were sorted. As shown in the right panel (FIGS. 5E and 5F) all sorted cells exhibit a high mCherry signal, indicating that the dual sensor system is indispensable for sorting of single cells expressing BRCA1-BRCT variants with improved folding properties.

Figure 5G:
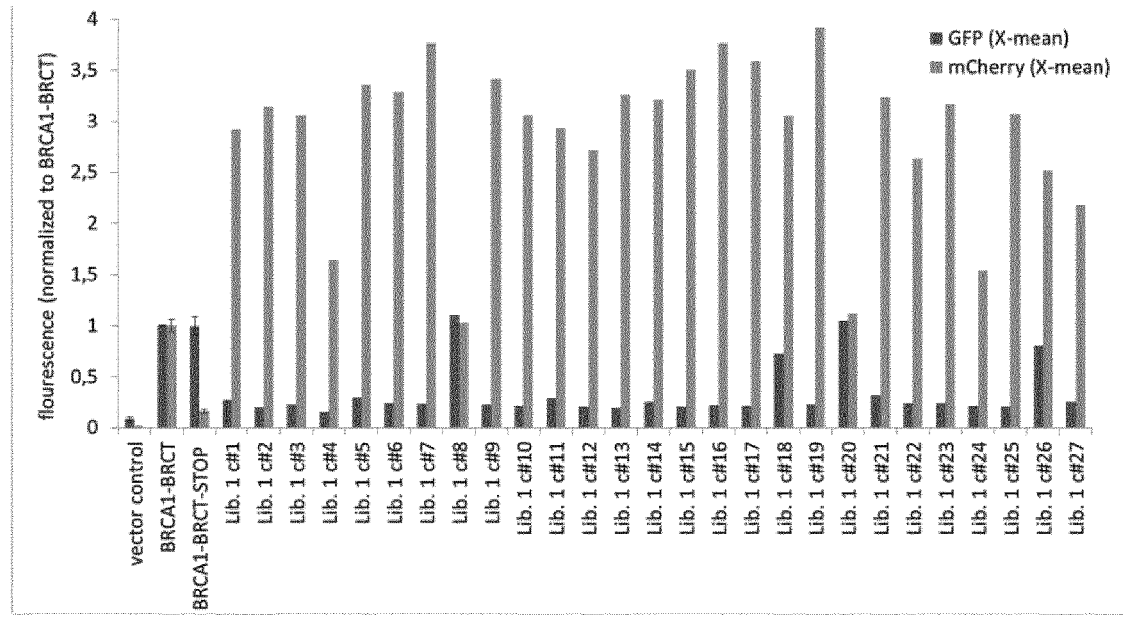
Figure 5G:
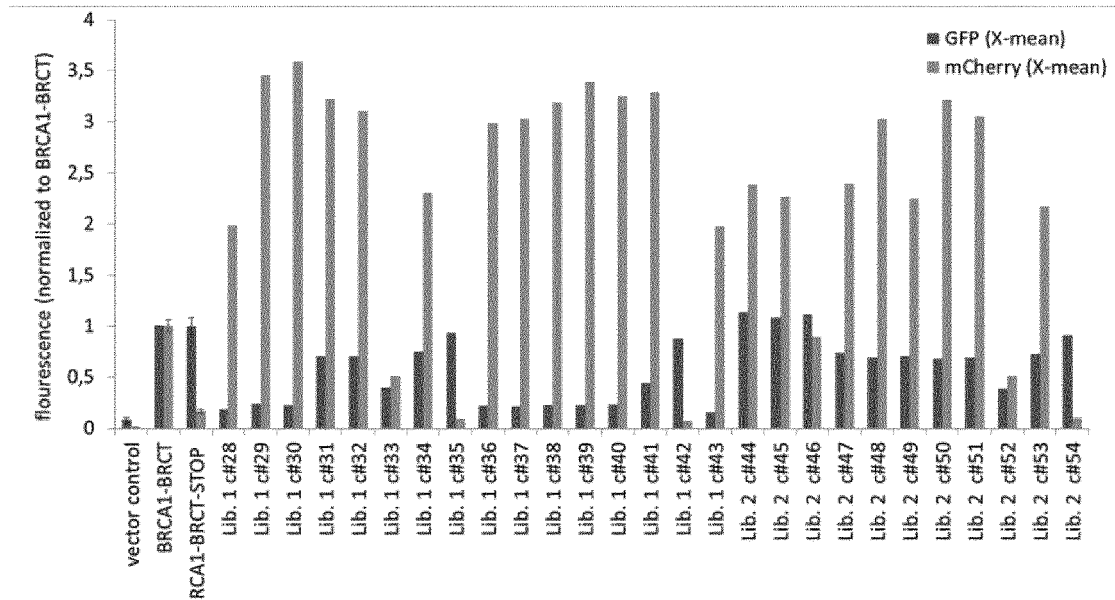

The mCherry (PE-Texas Red-A) and the GFP (FITC-A) signal of 54 sorted single clones were analyzed via flow cytometry after expression of mutant BRCA1-BRCT. As shown in FIG. 5G around 85% of the sorted cells express fully translated protein with exhibits improved folding properties.

Together the data show that the combination of protein translation and the protein folding sensor is crucial for sorting of rare events.

Example 6 - Sequence overview:

| Name | amino acid sequence | nucleotide sequence 5' - 3' |
|---|---|---|
| IbpAp | | SEQ-ID No: 1 |
| GFP-ASV | SEQ-ID No: 14 | SEQ-ID No: 2 |
| GFP-mut3 | SEQ-ID No: 15 | SEQ-ID No: 3 |
| translation coupling cassette | | SEQ-ID No: 4 |
| mCherry | SEQ-ID No: 16 | SEQ-ID No: 5 |
| PARP1-BRCT | SEQ-ID No: 17 | SEQ-ID No: 6 |
| BRCA1-BRCT | SEQ-ID No: 18 | SEQ-ID No: 7 |
| BRCA1-BRCT-STOP | SEQ-ID No: 19 | SEQ-ID No: 8 |
| BRCA1-BRCT-truncated | SEQ-ID No: 20 | SEQ-ID No: 9 |
| p19 | SEQ-ID No: 21 | SEQ-ID No: 10 |
| E6 | SEQ-ID No: 22 | SEQ-ID No: 11 |
| NusA | SEQ-ID No: 23 | SEQ-ID No: 12 |
| SUMO | SEQ-ID No: 24 | SEQ-ID No: 13 |

REFERENCES

Rayees U H Mattoo and Pierre Goloubinoff, "Molecular Chaperones Are Nanomachines That Catalytically Unfold Misfolded and Alternatively Folded Proteins.," Cellular and Molecular Life Sciences: CMLS 71, no. 17 (September 2014): 3311-25, doi:10.1007/s00018-014-1627-y.

Jeffrey G Marblestone et al., "Comparison of SUMO Fusion Technology with Traditional Gene Fusion Systems: Enhanced Expression and Solubility with SUMO.," Protein Science: a Publication of the Protein Society 15, no. 1 (January 2006): 182-89, doi:10.1110/ps.051812706.

Michael R Dyson et al., "Production of Soluble Mammalian Proteins in *Escherichia Coli*: Identification of Protein Features That Correlate with Successful Expression.," BMC Biotechnology 4 (Dec. 14, 2004): 32, doi:10.1186/1472-6750-4-32.

Yan-Ping Shih et al., "High-Throughput Screening of Soluble Recombinant Proteins.," Protein Science: a Publication of the Protein Society 11, no. 7 (July 2002): 1714-19, doi:10.1110/ps.0205202.

Renaud Vincentelli et al., "Automated Expression and Solubility Screening of His-Tagged Proteins in 96-Well Format.," Analytical Biochemistry 346, no. 1 (Nov. 1, 2005): 77-84, doi:10.1016/j.ab.2005.07.039.

Zhenzhen Wang et al., "Coupled Selection of Protein Solubility in *E. Coli* Using Uroporphyrinogen III Methyltransferase as Red Fluorescent Reporter.," Journal of Biotechnology 186 (Jul. 3, 2014): 169-74, doi:10.1016/j.jbiotec.2014.06.025.

Mario Kraft et al., "An Online Monitoring System Based on a Synthetic Sigma32-Dependent Tandem Promoter for Visualization of Insoluble Proteins in the Cytoplasm of *Escherichia Coli*.," Applied Microbiology and Biotechnology 75, no. 2 (May 2007): 397-406, doi:10.1007/s00253-006-0815-6.

Tina Schultz, Lucia Martinez, and Ario de Marco, "The Evaluation of the Factors That Cause Aggregation During Recombinant Expression in *E. Coli* Is Simplified by the Employment of an Aggregation-Sensitive Reporter.," Microbial Cell Factories 5 (2006): 28, doi:10.1186/1475-2859-5-28.

Daniel Mendez-Perez et al., "A Translation-Coupling DNA Cassette for Monitoring Protein Translation in *Escherichia Coli*.," Metabolic Engineering 14, no. 4 (July 2012): 298-305, doi:10.1016/j.ymben.2012.04.005.

Scott A Lesley et al., "Gene Expression Response to Misfolded Protein as a Screen for Soluble Recombinant Protein.," Protein Engineering 15, no. 2 (February 2002): 153-60

Shaner et al. 2005 A guide to choosing fluorescent proteins NATURE METHODS|VOL. 2 NO. 12|DECEMBER pp 905-909

Andersen, J. B., C. Sternberg, L. K. Poulsen, S. P. Bjorn, M. Givskov, and S. Molin. 1998. "New Unstable Variants of Green Fluorescent Protein for Studies of Transient Gene Expression in Bacteria." Applied and Environmental Microbiology 64 (6): 2240-2246.

Butt, T. R., S. C. Edavettal, J. P. Hall, and M. R. Mattern. 2005. "SUMO Fusion Technology for Difficult-to-Express Proteins." Protein Expression and Purification 43 (1): 1-9.

Davis, G. D., C. Elisee, D. M. Newham, and R. G. Harrison. 1999. "New Fusion Protein Systems Designed to Give Soluble Expression in *Escherichia Coli*." Biotechnology and Bioengineering 65 (4): 382-388.

Gregersen N, Bolund L, Bross P. 2005. Protein misfolding, aggregation, and degradation in disease. Mol Biotechnol. 31(2):141-50.

Solubilization and refolding of inclusion body proteins. Singh A, Upadhyay V, Panda A K. Methods Mol Biol. 2015; 1258:283-91. doi: 10.1007/978-1-4939-2205-5_15. Review.

Rudolph and Lilie, 1996. In vitro folding of inclusion body proteins, The FASEB Journal, Vol. 10 49-56.

Ramon A, Senorale-Pose M, Marin M. 2014. Inclusion bodies: not that bad . . . . Front Microbiol, 5:56.

The invention claimed is:

1. A single cell two-cassette reporter system comprising:
   a) a first cassette comprising:
      a target gene comprising a coding sequence having a 5' end and a 3' end;
      a first reporter gene, wherein translation of the first reporter gene is translationally linked to the target gene; and
   b) a second cassette comprising:
      a protein inclusion body responsive promoter operably linked to a second reporter gene.

2. The system according to claim 1, wherein the first cassette further comprises:
   a first reporter gene translation control element configured for controlling translation of the first reporter gene in a transcript of the first cassette;
   a secondary structure-forming sequence that reversibly forms a secondary structure that masks the first reporter gene translation control element and encompasses at least a portion of the 3' end of the coding sequence of the target gene, wherein at least part of the secondary structure-forming sequence is translationally linked with the target gene, wherein the secondary structure-forming sequence is configured so that target gene translation induces unmasking of the first reporter gene translation control element.

3. The system according to claim 1, wherein the target gene is fused to the first reporter gene, wherein the fusion of the target gene to the first reporter gene is configured so that complete target gene translation yields a fusion protein of the target gene and the first reporter gene or a first reporter gene fragment.

4. The system according to claim 1, wherein the second cassette is located in a plasmid having a low copy number.

5. The system according to claim 1, wherein the second and first reporter genes encodes a fluorescent protein, wherein the fluorescent protein encoded by the second reporter gene is different from the fluorescent protein encoded by the first reporter gene.

6. The system according to claim 5, wherein the fluorescent protein is a destabilized GFP, wherein the destabilized GFP is at least 75% identical to the polypeptide sequence of SEQ ID NO: 14.

7. The system according to claim 1, wherein the first reporter gene encodes a polypeptide selected from the group consisting of metabolic enzyme, antibiotic resistance protein, luminescent protein, chemiluminescent protein, and fluorescent protein.

8. The system according to claim 7, wherein the second reporter gene encodes a polypeptide selected from the group consisting of a metabolic enzyme, antibiotic resistance protein, luminescent protein, chemiluminescent protein, and fluorescent protein.

9. The system according to claim 1, wherein the protein inclusion body responsive promoter comprises a promoter that is induced when misfolded protein is present in a cell comprising the system.

10. The system according to claim 1, wherein the protein inclusion body responsive promoter comprises an alternative sigma factor $\sigma^{32}$ (RpoH) controlled promoter.

11. The system according to claim 1, wherein the protein inclusion body responsive promoter is selected from the group consisting of the ibpAB, yrfH, yccV, fsxA, dnaK, htpG, groEL, yhdN, yagU, yciS, ybeD, clpB and the araE promoter.

12. The system according to claim 1, wherein the protein inclusion body responsive promoter comprises a polynucleotide sequence at least 75% identical to the polynucleotide sequence of SEQ ID NO: 1.

13. A vector comprising the system of claim 1.

14. The system according to claim 1, wherein the second cassette is located in a plasmid having a medium copy number.

15. The system according to claim 1, wherein the second reporter gene encodes a polypeptide selected from the group consisting of a metabolic enzyme, antibiotic resistance protein, luminescent protein, chemiluminescent protein, and fluorescent protein.

16. A method of assessing target gene translation and/or target gene product solubility, the method comprising the steps of:
   a) providing the two-cassette reporter system according to claim 1, wherein the first reporter gene encodes for a first report protein capable of generating a first signal, and the second reporter gene encodes a second reporter protein capable of generating a second signal,
   b) expressing the two-cassette reporter system in a host cell
   c) determining the first and/or the second signal using analysis means; and
   d) i) assessing the target gene translation on the basis of the first signal, and/or ii) assessing target gene product solubility on the basis of the second signal by comparison to appropriate control host cells.

17. The method according to claim 16, wherein step b) further comprises contacting said host cell with a plurality of molecules to be screened for pharmacoperone activity, and wherein step d) is a step of assessing target gene product solubility and comprises analysing the second signal to determine which molecules can restore proper folding of the protein.

18. The method according to claim 17, wherein step d) further comprises sorting the cells based on the second signal.

19. The method according to claim 16, wherein the target gene is provided in a library comprising a plurality of vectors comprising the system according to claim 1, wherein the target gene library is expressed in a plurality of host cells, the method further comprising the steps of:
   e) sorting the cells into at least two populations based on the second and optionally the first signal,
   f) isolating the vectors comprised in the cells of the sorted populations,
   g) identifying the sequences of the target genes comprised within said isolated vectors, and
   h) comparing the sequences of the target genes of the two sorted populations.

* * * * *

SEQUENCE LISTING

```
<160> NUMBER OF SEQ ID NOS: 51

<210> SEQ ID NO 1
<211> LENGTH: 295
<212> TYPE: DNA
<213> ORGANISM: Artificial Sequence
<220> FEATURE:
<223> OTHER INFORMATION: IbpAp

<400> SEQUENCE: 1
aattcatctg ttgatcgtgg gtgttggcct gatgagttat agcgatccct tgctgaaaat      60
aacatcatca ttacgtcgca ctgtggcggc tatcgcactt taacgtttcg tgctgccccc     120
tcagtctatg caatagacca taaactgcaa aaaaaagtcc gctgataagg cttgaaaagt     180
tcatttccag acccattttt acatcgtagc cgatgaggac gcgcctgatg ggtgttctgg     240
ctacctgacc tgtccattgt ggaaggtctt acattctcgc tgatttcagg agcta          295

<210> SEQ ID NO 2
<211> LENGTH: 756
<212> TYPE: DNA
<213> ORGANISM: Artificial Sequence
<220> FEATURE:
<223> OTHER INFORMATION: GFP-ASV

<400> SEQUENCE: 2
atgcgtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tcggttatgg tgttcaatgc tttgcgagat acccagatca tatgaaacag     240
catgactttt tcaagagtgc catgcccgaa ggttatgtac aggaaagaac tatattttc      300 aaagatgacg ggaactacaa gacacgtgct gaagtcaagt ttgaaggtga taccttgtt     360 aatagaatcg agttaaaagg tattgatttt aaagaagatg gaaacattct tggacacaaa     420
ttggaataca actataactc acacaatgta tacatcatgg cagacaaaca aaagaatgga     480
atcaaagtta acttcaaaat tagacacaac attgaagatg gaagcgttca actagcagac     540
cattatcaac aaaatactcc aattggcgat ggccctgtcc ttttaccaga caaccattac     600
ctgtccacac aatctgccct ttcgaaagat cccaacgaaa agagagacca catggtcctt     660
```

```
cttgagtttg taacagctgc tgggattaca catggcatgg atgaactata caaaaggcct    720
gcagcaaacg acgaaaacta cgctgcatca gtttaa                              756

<210> SEQ ID NO 3
<211> LENGTH: 717
<212> TYPE: DNA
<213> ORGANISM: Artificial Sequence
<220> FEATURE:
<223> OTHER INFORMATION: GFP-mut3

<400> SEQUENCE: 3
atgcgtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactt tcggttatgg tgttcaatgc tttgcgagat acccagatca tatgaaacag    240
catgactttt tcaagagtgc catgcccgaa ggttatgtac aggaaagaac tatatttttc    300
aaagatgacg ggaactacaa gacacgtgct gaagtcaagt ttgaaggtga tacccttgtt    360
aatagaatcg agttaaaagg tattgatttt aaagaagatg gaaacattct tggacacaaa    420
ttggaataca actataactc acacaatgta tacatcatgg cagacaaaca aaagaatgga    480
atcaaagtta acttcaaaat tagacacaac attgaagatg gaagcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaataa       717

<210> SEQ ID NO 4
<211> LENGTH: 43
<212> TYPE: DNA
<213> ORGANISM: Artificial Sequence
<220> FEATURE:
<223> OTHER INFORMATION: translation coupling cassette

<400> SEQUENCE: 4
actagtcatc atcaccacca tcattaggat ggtggtgatg ata                       43

<210> SEQ ID NO 5
<211> LENGTH: 711
<212> TYPE: DNA
<213> ORGANISM: Artificial Sequence
<220> FEATURE:
<223> OTHER INFORMATION: mCherry

<400> SEQUENCE: 5
atggttagca aaggtgaaga ggataatatg gccatcatca agaatttat gcgctttaaa      60 gtgcacatgg aaggtagcgt taatggccat gaatttgaaa ttgaaggtga aggcgaaggt    120
cgtccgtatg aaggcaccca gaccgcaaaa ctgaaagtta ccaaaggtgg tccgctgccg    180
tttgcatggg atattctgag tccgcagttt atgtatggta gcaaagccta tgttaaacat    240
ccggcagata tcccggatta tctgaaactg agctttccgg aaggttttaa atgggaacgt    300
gtgatgaatt ttgaagatgg tggtgtggtg accgttaccc aggatagcag cctgcaggat    360
ggtgaattta tctataaagt taaactgcgt ggcaccaatt ttccgagtga tggtccggtt    420
atgcagaaaa aaacaatggg ttgggaagca agcagcgaac gtatgtatcc ggaagatggc    480
gcactgaaag gtgaaattaa acagcgcctg aaactgaaag atggtggcca ttatgatgca    540
```

```
gaagttaaaa ccacctataa agccaaaaaa ccggttcagc tgcctggtgc atataacgtt    600
aacattaaac tggatatcac cagccacaac gaggattata ccattgttga acagtatgaa    660
cgtgcagaag gtcgccatag taccggtggt atggatgaac tgtataaatg a             711

<210> SEQ ID NO 6
<211> LENGTH: 347
<212> TYPE: DNA
<213> ORGANISM: Artificial Sequence
<220> FEATURE:
<223> OTHER INFORMATION: PARP1-BRCT

<400> SEQUENCE: 6
gtgaactcct ctgcttcagc agataagcca ttatccaaca tgaagatcct gactctcggg    60
aagctgtccc ggaacaagga tgaagtgaag gccatgattg agaaactcgg ggggaagttg    120
acggggacgg ccaacaaggc ttccctgtgc atcagcacca aaaaggaggt ggaaaagatg    180
aataagaaga tggaggaagt aaaggaagcc aacatccgag ttgtgtctga ggacttcctc    240
caggacgtct ccgcctccac caagagcctt caggagttgt tcttagcgca catcttgtcc    300
ccttgggggg cagaggtgaa ggcagagcct gttgaagttg tggcccc                  347

<210> SEQ ID NO 7
<211> LENGTH: 642
<212> TYPE: DNA
<213> ORGANISM: Artificial Sequence
<220> FEATURE:
<223> OTHER INFORMATION: BRCA1-BRCT

<400> SEQUENCE: 7
gtcaacaaaa gaatgtccat ggtggtgtct ggcctgaccc cagaagaatt tatgctcgtg    60
tacaagtttg ccagaaaaca ccacatcact ttaactaatc taattactga agagactact    120
catgttgtta tgaaaacaga tgctgagttt gtgtgtgaac ggacactgaa atattttcta    180
ggaattgcgg gaggaaaatg gqtagttagc tatttctggg tgacccagtc tattaaagaa    240
agaaaaatgc tgaatgagca tgattttgaa gtcagaggag atgtggtcaa tggaagaaac    300
caccaaggtc caaagcgagc aagagaatcc caggacagaa agatcttcag ggggctagaa    360
atctgttgct atgggccctt caccaacatg cccacagatc aactggaatg gatggtacag    420
ctgtgtggtg cttctgtggt gaaggagctt tcatcattca cccttggcac aggtgtccac    480
ccaattgtgg ttgtgcagcc agatgcctgg acagaggaca atggcttcca tgcaattggg    540
cagatgtgtg aggcacctgt ggtgacccga gagtgggtgt tggacagtgt agcactctac    600
cagtgccagg agctggacac ctacctgata ccccagatcc cc                       642

<210> SEQ ID NO 8
<211> LENGTH: 645
<212> TYPE: DNA
<213> ORGANISM: Artificial Sequence
<220> FEATURE:
<223> OTHER INFORMATION: BRCA1-BRCT-STOP

<400> SEQUENCE: 8
gtcaacaaaa gaatgtccat ggtggtgtct ggcctgaccc cagaagaatt tatgctcgtg    60
tacaagtttg ccagaaaaca ccacatcact ttaactaatc taattactga agagactact    120
catgttgtta tgaaaacaga tgctgagttt gtgtgtgaac ggacactgaa atattttcta    180
ggaattgcgg gaggaaaatg gqtagttagc tatttctggg tgacccagtc tattaaagaa    240
agaaaaatgc tgaatgagca tgattttgaa gtcagaggag atgtggtcaa tggaagaaac    300
```

```
caccaaggtc caaagcgagc aagagaatcc caggacagaa agatcttcag ggggctagaa      360
atctgttgct atgggccctt caccaacatg cccacagatc aactggaatg gatggtacag      420
ctgtgtggtg cttctgtggt gaaggagctt tcatcattca cccttggcac aggtgtccac      480
ccaattgtgg ttgtgcagcc agatgcctgg acagaggaca atggcttcca tgcaattggg      540
cagatgtgtg aggcacctgt ggtgacccga gagtgggtgt tggacagtgt agcactctac      600
cagtgccagg agctggacac ctacctgata ccccagatcc cctaa                     645

<210> SEQ ID NO 9
<211> LENGTH: 561
<212> TYPE: DNA
<213> ORGANISM: Artificial Sequence
<220> FEATURE:
<223> OTHER INFORMATION: BRCA1-BRCT-truncated

<400> SEQUENCE: 9
gtcaacaaaa gaatgtccat ggtggtgtct ggcctgaccc cagaagaatt tatgctcgtg       60
tacaagtttg ccagaaaaca ccacatcact ttaactaatc taattactga agagactact      120
catgttgtta tgaaaacaga tgctgagttt gtgtgtgaac ggacactgaa atattttcta      180
ggaattgcgg gaggaaaatg ggtagttagc tatttctggg tgacccagtc tattaaagaa      240
agaaaaatgc tgaatgagca tgattttgaa gtcagaggag atgtggtcaa tggaagaaac      300
caccaaggtc caaagcgagc aagagaatcc caggacagaa agatcttcag ggggctagaa      360
atctgttgct atgggccctt caccaacatg cccacagatc aactggaatg gatggtacag      420
ctgtgtggtg cttctgtggt gaaggagctt tcatcattca cccttggcac aggtgtccac      480
ccaattgtgg ttgtgcagcc agatgcctgg acagaggaca atggcttcca tgcaattggg      540
cagatgtgtg aggcacctgt g                                                561

<210> SEQ ID NO 10
<211> LENGTH: 495
<212> TYPE: DNA
<213> ORGANISM: Artificial Sequence
<220> FEATURE:
<223> OTHER INFORMATION: p19

<400> SEQUENCE: 10
ctgctggaag aagttcgcgc aggcgatcgt ctgagcggtg cagcagcacg tggtgatgtt       60
caagaagtgc gtcgtctgct gcatcgtgaa ctggttcatc ctgatgcact gaatcgtttt      120
ggtaaaaccg cactgcaggt tatgatgttt ggtagcaccg caattgcact ggaactgctg      180
aaacagggtg caagcccgaa tgttcaggat accagcggca ccagtccggt tcatgatgcc      240
gcacgtaccg gttttctgga tacccctgaaa gttctggttg aacatggtgc agatgttaat      300
gttccggatg gtacaggtgc actgccgatt catctggccg tgcaagaagg tcataccgca      360
gttgttagct ttctggcagc agaaagcgat ctgcatcgtc gtgatgcacg tggtctgaca      420
ccgctggaac tggcactgca gcgtggtgca caggatctgg ttgatattct gcagggtcac      480
atggttgcac cgctg                                                       495

<210> SEQ ID NO 11
<211> LENGTH: 471
<212> TYPE: DNA
<213> ORGANISM: Artificial Sequence
<220> FEATURE:
<223> OTHER INFORMATION: E6
```

<400> SEQUENCE: 11

```
gcgcgctttg aggatccaac acggcgaccc tacaagctac ctgatctgtg cacggaactg      60
aacacttcac tgcaagacat agaaataacc tgtgtatatt gcaagacagt attggaactt     120
acagaggtat ttgaatttgc atttaaagat ttatttgtgg tgtatagaga cagtataccg     180
catgctgcat gccataaatg tatagatttt tattctagaa ttagagaatt aagacattat     240
tcagactctg tgtatggaga cacattggaa aaactaacta acactgggtt atacaattta     300
ttaataaggt gcctgcggtg ccagaaaccg ttgaatccag cagaaaaact tagacacctt     360
aatgaaaaac gacgattcca caacatagct gggcactata gaggccagtg ccattcgtgc     420
tgcaaccgag cacgacagga aagactccaa cgacgcagag aaacacaagt a              471
```

<210> SEQ ID NO 12
<211> LENGTH: 1500
<212> TYPE: DNA
<213> ORGANISM: Artificial Sequence
<220> FEATURE:
<223> OTHER INFORMATION: NusA

<400> SEQUENCE: 12

```
aacaaagaaa ttttggctgt agttgaagcc gtatccaatg aaaaggcgct acctcgcgag      60
aagattttcg aagcattgga aagcgcgctg gcgacagcaa caagaaaaa atatgaacaa     120
gagatcgacg tccgcgtaca gatcgatcgc aaaagcggtg attttgacac tttccgtcgc     180
tggttagttg ttgatgaagt cacccagccg accaaggaaa tcacccttga agccgcacgt     240
tatgaagatg aaagcctgaa cctgggcgat tacgttgaag atcagattga gtctgttacc     300
tttgaccgta tcactaccca gacggcaaaa caggttatcg tgcagaaagt gcgtgaagcc     360
gaacgtgcga tggtggttga tcagttccgt gaacacgaag tgaaatcat caccggcgtg     420
gtgaaaaaag taaaccgcga caacatctct ctggatctgg caacaacgc tgaagccgtg     480
atcctgcgcg aagatatgct gccgcgtgaa aacttccgcc ctggcgaccg cgttcgtggc     540
gtgctctatt ccgttcgccc ggaagcgcgt ggcgcgcaac tgttcgtcac tcgttccaag     600
ccggaaatgc tgatcgaact gttccgtatt gaagtgccag aaatcggcga agaagtgatt     660
gaaattaaag cagcggctcg cgatccgggt tctcgtgcga aaatcgcggt gaaaaccaac     720
gataaacgta tcgatccggt aggtgcttgc gtaggtatgc gtggcgcgcg tgttcaggcg     780
gtgtctactg aactgggtgg cgagcgtatc gatatcgtcc tgtgggatga taacccggcg     840
cagttcgtga ttaacgcaat ggcaccggca gacgttgctt ctatcgtggt ggatgaagat     900
aaacacacca tggatatcgc cgttgaagcc ggtaacctgg cgcaggcgat tggccgtaac     960
ggtcagaacg tgcgtctggc ttcgcagctg agcggttggg aactcaacgt tgatgaccgtt   1020
gacgacctgc aggctaagca tcaggcggaa gcgcacgcag cgatcgacac cttcaccaaa    1080
tatctcgaca tcgacgaaga cttcgcgact gttctggtag aagaaggctt ctcgacgctg    1140
gaagaattgg cctatgtgcc gatgaaagag ctgttggaaa tcgaaggcct tgatgagccg    1200
accgttgaag cactgcgcga gcgtgctaaa aatgcactgg ccaccattgc acaggcccag    1260
gaagaaagcc tcggtgataa caaaccggct gacgatctgc tgaaccttga agggggtagat   1320
cgtgatttgg cattcaaact ggccgcccgt ggcgtttgta cgctggaaga tctcgccgaa    1380
cagggcattg atgatctggc tgatatcgaa gggttgaccg acgaaaaagc cggagcactg    1440
attatggctg cccgtaatat ttgctggttc ggtgacgaag cgggtagcgg ctctggtagc    1500
```

<210> SEQ ID NO 13
<211> LENGTH: 309
<212> TYPE: DNA
<213> ORGANISM: Artificial Sequence
<220> FEATURE:
<223> OTHER INFORMATION: SUMO

<400> SEQUENCE: 13

```
tcggactcag aagtcaatca agaagctaag ccagaggtca agccagaagt caagcctgag    60
actcacatca atttaaaggt gtccgatgga tcttcagaga tcttcttcaa gatcaaaaag   120
accactcctt taagaaggct gatggaagcg ttcgctaaaa gacagggtaa ggaaatggac   180
tccttaagat tcttgtacga cggtattaga attcaagctg atcagacccc tgaagatttg   240
gacatggagg ataacgatat tattgaggct cacagagaac agattggtgg tggtagcggc   300
tctggtagc                                                           309
```

<210> SEQ ID NO 14
<211> LENGTH: 251
<212> TYPE: PRT
<213> ORGANISM: Artificial Sequence
<220> FEATURE:
<223> OTHER INFORMATION: GFP-ASV

<400> SEQUENCE: 14

```
Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Arg Pro
225                 230                 235                 240

Ala Ala Asn Asp Glu Asn Tyr Ala Ala Ser Val
                245                 250
```

```
<210> SEQ ID NO 15
<211> LENGTH: 238
<212> TYPE: PRT
<213> ORGANISM: Artificial Sequence
<220> FEATURE:
<223> OTHER INFORMATION: translation coupling cassette

<400> SEQUENCE: 15

Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 16
<211> LENGTH: 236
<212> TYPE: PRT
<213> ORGANISM: Artificial Sequence
<220> FEATURE:
<223> OTHER INFORMATION: mCherry

<400> SEQUENCE: 16

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80
```

```
Pro Ala Asp Ile Pro Asp Tyr Leu Lys Leu Ser Phe Pro Glu Gly Phe
                85                  90                  95
Lys Trp Glu Arg Val Met Asn Phe Glu Asp Gly Val Val Thr Val
            100                 105                 110
Thr Gln Asp Ser Ser Leu Gln Asp Gly Glu Phe Ile Tyr Lys Val Lys
            115                 120                 125
Leu Arg Gly Thr Asn Phe Pro Ser Asp Gly Pro Val Met Gln Lys Lys
130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
                180                 185                 190
Gln Leu Pro Gly Ala Tyr Asn Val Asn Ile Lys Leu Asp Ile Thr Ser
                195                 200                 205
His Asn Glu Asp Tyr Thr Ile Val Glu Gln Tyr Glu Arg Ala Glu Gly
            210                 215                 220
Arg His Ser Thr Gly Gly Met Asp Glu Leu Tyr Lys
225                 230                 235

<210> SEQ ID NO 17
<211> LENGTH: 116
<212> TYPE: PRT
<213> ORGANISM: Artificial Sequence
<220> FEATURE:
<223> OTHER INFORMATION: PARP1-BRCT

<400> SEQUENCE: 17

Val Asn Ser Ser Ala Ser Ala Asp Lys Pro Leu Ser Asn Met Lys Ile
1               5                   10                  15
Leu Thr Leu Gly Lys Leu Ser Arg Asn Lys Asp Glu Val Lys Ala Met
            20                  25                  30
Ile Glu Lys Leu Gly Gly Lys Leu Thr Gly Thr Ala Asn Lys Ala Ser
            35                  40                  45
Leu Cys Ile Ser Thr Lys Lys Glu Val Glu Lys Met Asn Lys Lys Met
        50                  55                  60
Glu Glu Val Lys Glu Ala Asn Ile Arg Val Val Ser Glu Asp Phe Leu
65                  70                  75                  80
Gln Asp Val Ser Ala Ser Thr Lys Ser Leu Gln Glu Leu Phe Leu Ala
                85                  90                  95
His Ile Leu Ser Pro Trp Gly Ala Glu Val Lys Ala Glu Pro Val Glu
            100                 105                 110
Val Val Ala Pro
            115

<210> SEQ ID NO 18
<211> LENGTH: 214
<212> TYPE: PRT
<213> ORGANISM: Artificial Sequence
<220> FEATURE:
<223> OTHER INFORMATION: BRCA1-BRCT

<400> SEQUENCE: 18

Val Asn Lys Arg Met Ser Met Val Val Ser Gly Leu Thr Pro Glu Glu
1               5                   10                  15
Phe Met Leu Val Tyr Lys Phe Ala Arg Lys His His Ile Thr Leu Thr
```

```
            20                  25                  30
Asn Leu Ile Thr Glu Thr Thr His Val Val Met Lys Thr Asp Ala
            35                  40                  45
Glu Phe Val Cys Glu Arg Thr Leu Lys Tyr Phe Leu Gly Ile Ala Gly
        50                  55                  60
Gly Lys Trp Val Val Ser Tyr Phe Trp Val Thr Gln Ser Ile Lys Glu
 65                  70                  75                  80
Arg Lys Met Leu Asn Glu His Asp Phe Glu Val Arg Gly Asp Val Val
                    85                  90                  95
Asn Gly Arg Asn His Gln Gly Pro Lys Arg Ala Arg Glu Ser Gln Asp
                100                 105                 110
Arg Lys Ile Phe Arg Gly Leu Glu Ile Cys Cys Tyr Gly Pro Phe Thr
            115                 120                 125
Asn Met Pro Thr Asp Gln Leu Glu Trp Met Val Gln Leu Cys Gly Ala
        130                 135                 140
Ser Val Val Lys Glu Leu Ser Ser Phe Thr Leu Gly Thr Gly Val His
145                 150                 155                 160
Pro Ile Val Val Gln Pro Asp Ala Trp Thr Glu Asp Asn Gly Phe
                165                 170                 175
His Ala Ile Gly Gln Met Cys Glu Ala Pro Val Val Thr Arg Glu Trp
            180                 185                 190
Val Leu Asp Ser Val Ala Leu Tyr Gln Cys Gln Glu Leu Asp Thr Tyr
            195                 200                 205
Leu Ile Pro Gln Ile Pro
    210

<210> SEQ ID NO 19
<211> LENGTH: 214
<212> TYPE: PRT
<213> ORGANISM: Artificial Sequence
<220> FEATURE:
<223> OTHER INFORMATION: BRCA1-BRCT-STOP

<400> SEQUENCE: 19

Val Asn Lys Arg Met Ser Met Val Val Ser Gly Leu Thr Pro Glu Glu
 1               5                  10                  15
Phe Met Leu Val Tyr Lys Phe Ala Arg Lys His His Ile Thr Leu Thr
            20                  25                  30
Asn Leu Ile Thr Glu Glu Thr Thr His Val Val Met Lys Thr Asp Ala
            35                  40                  45
Glu Phe Val Cys Glu Arg Thr Leu Lys Tyr Phe Leu Gly Ile Ala Gly
        50                  55                  60
Gly Lys Trp Val Val Ser Tyr Phe Trp Val Thr Gln Ser Ile Lys Glu
 65                  70                  75                  80
Arg Lys Met Leu Asn Glu His Asp Phe Glu Val Arg Gly Asp Val Val
                    85                  90                  95
Asn Gly Arg Asn His Gln Gly Pro Lys Arg Ala Arg Glu Ser Gln Asp
                100                 105                 110
Arg Lys Ile Phe Arg Gly Leu Glu Ile Cys Cys Tyr Gly Pro Phe Thr
            115                 120                 125
Asn Met Pro Thr Asp Gln Leu Glu Trp Met Val Gln Leu Cys Gly Ala
        130                 135                 140
Ser Val Val Lys Glu Leu Ser Ser Phe Thr Leu Gly Thr Gly Val His
145                 150                 155                 160
Pro Ile Val Val Gln Pro Asp Ala Trp Thr Glu Asp Asn Gly Phe
```

```
                    165                 170                 175

His Ala Ile Gly Gln Met Cys Glu Ala Pro Val Val Thr Arg Glu Trp
            180                 185                 190

Val Leu Asp Ser Val Ala Leu Tyr Gln Cys Gln Glu Leu Asp Thr Tyr
        195                 200                 205

Leu Ile Pro Gln Ile Pro
        210

<210> SEQ ID NO 20
<211> LENGTH: 187
<212> TYPE: PRT
<213> ORGANISM: Artificial Sequence
<220> FEATURE:
<223> OTHER INFORMATION: BRCA1-BRCT-truncated

<400> SEQUENCE: 20

Val Asn Lys Arg Met Ser Met Val Val Ser Gly Leu Thr Pro Glu Glu
1               5                   10                  15

Phe Met Leu Val Tyr Lys Phe Ala Arg Lys His His Ile Thr Leu Thr
            20                  25                  30

Asn Leu Ile Thr Glu Glu Thr Thr His Val Val Met Lys Thr Asp Ala
        35                  40                  45

Glu Phe Val Cys Glu Arg Thr Leu Lys Tyr Phe Leu Gly Ile Ala Gly
    50                  55                  60

Gly Lys Trp Val Val Ser Tyr Phe Trp Val Thr Gln Ser Ile Lys Glu
65                  70                  75                  80

Arg Lys Met Leu Asn Glu His Asp Phe Glu Val Arg Gly Asp Val Val
                85                  90                  95

Asn Gly Arg Asn His Gln Gly Pro Lys Arg Ala Arg Glu Ser Gln Asp
            100                 105                 110

Arg Lys Ile Phe Arg Gly Leu Glu Ile Cys Cys Tyr Gly Pro Phe Thr
        115                 120                 125

Asn Met Pro Thr Asp Gln Leu Glu Trp Met Val Gln Leu Cys Gly Ala
    130                 135                 140

Ser Val Val Lys Glu Leu Ser Ser Phe Thr Leu Gly Thr Gly Val His
145                 150                 155                 160

Pro Ile Val Val Val Gln Pro Asp Ala Trp Thr Glu Asp Asn Gly Phe
                165                 170                 175

His Ala Ile Gly Gln Met Cys Glu Ala Pro Val
            180                 185

<210> SEQ ID NO 21
<211> LENGTH: 165
<212> TYPE: PRT
<213> ORGANISM: Artificial Sequence
<220> FEATURE:
<223> OTHER INFORMATION: p19

<400> SEQUENCE: 21

Leu Leu Glu Glu Val Arg Ala Gly Asp Arg Leu Ser Gly Ala Ala Ala
1               5                   10                  15

Arg Gly Asp Val Gln Glu Val Arg Arg Leu Leu His Arg Glu Leu Val
            20                  25                  30

His Pro Asp Ala Leu Asn Arg Phe Gly Lys Thr Ala Leu Gln Val Met
        35                  40                  45

Met Phe Gly Ser Thr Ala Ile Ala Leu Glu Leu Leu Lys Gln Gly Ala
    50                  55                  60
```

-continued

```
Ser Pro Asn Val Gln Asp Thr Ser Gly Thr Ser Pro Val His Asp Ala
 65                  70                  75                  80

Ala Arg Thr Gly Phe Leu Asp Thr Leu Lys Val Leu Val Glu His Gly
                 85                  90                  95

Ala Asp Val Asn Val Pro Asp Gly Thr Gly Ala Leu Pro Ile His Leu
            100                 105                 110

Ala Val Gln Glu Gly His Thr Ala Val Val Ser Phe Leu Ala Ala Glu
        115                 120                 125

Ser Asp Leu His Arg Arg Asp Ala Arg Gly Leu Thr Pro Leu Glu Leu
    130                 135                 140

Ala Leu Gln Arg Gly Ala Gln Asp Leu Val Asp Ile Leu Gln Gly His
145                 150                 155                 160

Met Val Ala Pro Leu
                165
```

<210> SEQ ID NO 22
<211> LENGTH: 157
<212> TYPE: PRT
<213> ORGANISM: Artificial Sequence
<220> FEATURE:
<223> OTHER INFORMATION: E6

<400> SEQUENCE: 22

```
Ala Arg Phe Glu Asp Pro Thr Arg Arg Pro Tyr Lys Leu Pro Asp Leu
  1               5                  10                  15

Cys Thr Glu Leu Asn Thr Ser Leu Gln Asp Ile Glu Ile Thr Cys Val
                 20                  25                  30

Tyr Cys Lys Thr Val Leu Glu Leu Thr Glu Val Phe Glu Phe Ala Phe
             35                  40                  45

Lys Asp Leu Phe Val Val Tyr Arg Asp Ser Ile Pro His Ala Ala Cys
         50                  55                  60

His Lys Cys Ile Asp Phe Tyr Ser Arg Ile Arg Glu Leu Arg His Tyr
 65                  70                  75                  80

Ser Asp Ser Val Tyr Gly Asp Thr Leu Glu Lys Leu Thr Asn Thr Gly
                 85                  90                  95

Leu Tyr Asn Leu Leu Ile Arg Cys Leu Arg Cys Gln Lys Pro Leu Asn
            100                 105                 110

Pro Ala Glu Lys Leu Arg His Leu Asn Glu Lys Arg Arg Phe His Asn
        115                 120                 125

Ile Ala Gly His Tyr Arg Gly Gln Cys His Ser Cys Cys Asn Arg Ala
    130                 135                 140

Arg Gln Glu Arg Leu Gln Arg Arg Glu Thr Gln Val
145                 150                 155
```

<210> SEQ ID NO 23
<211> LENGTH: 500
<212> TYPE: PRT
<213> ORGANISM: Artificial Sequence
<220> FEATURE:
<223> OTHER INFORMATION: NusA

<400> SEQUENCE: 23

```
Asn Lys Glu Ile Leu Ala Val Val Glu Ala Val Ser Asn Glu Lys Ala
  1               5                  10                  15

Leu Pro Arg Glu Lys Ile Phe Glu Ala Leu Glu Ser Ala Leu Ala Thr
                 20                  25                  30

Ala Thr Lys Lys Lys Tyr Glu Gln Glu Ile Asp Val Arg Val Gln Ile
             35                  40                  45
```

```
Asp Arg Lys Ser Gly Asp Phe Asp Thr Phe Arg Arg Trp Leu Val Val
    50                  55                  60
Asp Glu Val Thr Gln Pro Thr Lys Glu Ile Thr Leu Glu Ala Ala Arg
65                  70                  75                  80
Tyr Glu Asp Glu Ser Leu Asn Leu Gly Asp Tyr Val Glu Asp Gln Ile
                85                  90                  95
Glu Ser Val Thr Phe Asp Arg Ile Thr Thr Gln Thr Ala Lys Gln Val
                100                 105                 110
Ile Val Gln Lys Val Arg Glu Ala Glu Arg Ala Met Val Val Asp Gln
            115                 120                 125
Phe Arg Glu His Glu Gly Glu Ile Ile Thr Gly Val Val Lys Lys Val
    130                 135                 140
Asn Arg Asp Asn Ile Ser Leu Asp Leu Gly Asn Asn Ala Glu Ala Val
145                 150                 155                 160
Ile Leu Arg Glu Asp Met Leu Pro Arg Glu Asn Phe Arg Pro Gly Asp
                165                 170                 175
Arg Val Arg Gly Val Leu Tyr Ser Val Arg Pro Glu Ala Arg Gly Ala
                180                 185                 190
Gln Leu Phe Val Thr Arg Ser Lys Pro Glu Met Leu Ile Glu Leu Phe
    195                 200                 205
Arg Ile Glu Val Pro Glu Ile Gly Glu Glu Val Ile Glu Ile Lys Ala
    210                 215                 220
Ala Ala Arg Asp Pro Gly Ser Arg Ala Lys Ile Ala Val Lys Thr Asn
225                 230                 235                 240
Asp Lys Arg Ile Asp Pro Val Gly Ala Cys Val Gly Met Arg Gly Ala
                245                 250                 255
Arg Val Gln Ala Val Ser Thr Glu Leu Gly Gly Glu Arg Ile Asp Ile
                260                 265                 270
Val Leu Trp Asp Asp Asn Pro Ala Gln Phe Val Ile Asn Ala Met Ala
    275                 280                 285
Pro Ala Asp Val Ala Ser Ile Val Val Asp Glu Asp Lys His Thr Met
    290                 295                 300
Asp Ile Ala Val Glu Ala Gly Asn Leu Ala Gln Ala Ile Gly Arg Asn
305                 310                 315                 320
Gly Gln Asn Val Arg Leu Ala Ser Gln Leu Ser Gly Trp Glu Leu Asn
                325                 330                 335
Val Met Thr Val Asp Asp Leu Gln Ala Lys His Gln Ala Glu Ala His
                340                 345                 350
Ala Ala Ile Asp Thr Phe Thr Lys Tyr Leu Asp Ile Asp Glu Asp Phe
            355                 360                 365
Ala Thr Val Leu Val Glu Glu Gly Phe Ser Thr Leu Glu Glu Leu Ala
    370                 375                 380
Tyr Val Pro Met Lys Glu Leu Leu Glu Ile Glu Gly Leu Asp Glu Pro
385                 390                 395                 400
Thr Val Glu Ala Leu Arg Glu Arg Ala Lys Asn Ala Leu Ala Thr Ile
                405                 410                 415
Ala Gln Ala Gln Glu Glu Ser Leu Gly Asp Asn Lys Pro Ala Asp Asp
                420                 425                 430
Leu Leu Asn Leu Glu Gly Val Asp Arg Asp Leu Ala Phe Lys Leu Ala
            435                 440                 445
Ala Arg Gly Val Cys Thr Leu Glu Asp Leu Ala Glu Gln Gly Ile Asp
    450                 455                 460
```

```
Asp Leu Ala Asp Ile Glu Gly Leu Thr Asp Glu Lys Ala Gly Ala Leu
465                 470                 475                 480

Ile Met Ala Ala Arg Asn Ile Cys Trp Phe Gly Asp Glu Ala Gly Ser
                485                 490                 495

Gly Ser Gly Ser
            500

<210> SEQ ID NO 24
<211> LENGTH: 103
<212> TYPE: PRT
<213> ORGANISM: Artificial Sequence
<220> FEATURE:
<223> OTHER INFORMATION: SUMO

<400> SEQUENCE: 24

Ser Asp Ser Glu Val Asn Gln Glu Ala Lys Pro Glu Val Lys Pro Glu
1               5                   10                  15

Val Lys Pro Glu Thr His Ile Asn Leu Lys Val Ser Asp Gly Ser Ser
            20                  25                  30

Glu Ile Phe Phe Lys Ile Lys Lys Thr Thr Pro Leu Arg Arg Leu Met
        35                  40                  45

Glu Ala Phe Ala Lys Arg Gln Gly Lys Glu Met Asp Ser Leu Arg Phe
    50                  55                  60

Leu Tyr Asp Gly Ile Arg Ile Gln Ala Asp Gln Thr Pro Glu Asp Leu
65                  70                  75                  80

Asp Met Glu Asp Asn Asp Ile Ile Glu Ala His Arg Glu Gln Ile Gly
                85                  90                  95

Gly Gly Ser Gly Ser Gly Ser
            100

<210> SEQ ID NO 25
<211> LENGTH: 31
<212> TYPE: DNA
<213> ORGANISM: Artificial Sequence
<220> FEATURE:
<223> OTHER INFORMATION: GFP-fwd

<400> SEQUENCE: 25
agtatctaga atgcgtaaag gagaagaact t                               31

<210> SEQ ID NO 26
<211> LENGTH: 30
<212> TYPE: DNA
<213> ORGANISM: Artificial Sequence
<220> FEATURE:
<223> OTHER INFORMATION: GFP-ASV-rev

<400> SEQUENCE: 26
actgactagt ttaaactgat gcagcgtagt                                30

<210> SEQ ID NO 27
<211> LENGTH: 34
<212> TYPE: DNA
<213> ORGANISM: Artificial Sequence
<220> FEATURE:
<223> OTHER INFORMATION: GFP-mut3-rev

<400> SEQUENCE: 27
actgactagt ttatttgtat agttcatcca tgcc                           34

<210> SEQ ID NO 28
<211> LENGTH: 32
```

<212> TYPE: DNA
<213> ORGANISM: Artificial Sequence
<220> FEATURE:
<223> OTHER INFORMATION: IbpAp-fwd

<400> SEQUENCE: 28
gagcttaatt aaaattcatc tgttgatcgt gg                          32

<210> SEQ ID NO 29
<211> LENGTH: 38
<212> TYPE: DNA
<213> ORGANISM: Artificial Sequence
<220> FEATURE:
<223> OTHER INFORMATION: IbpAp-rev

<400> SEQUENCE: 29
gatatctaga tagctcctga aatcagcgag aatgtaag                    38

<210> SEQ ID NO 30
<211> LENGTH: 55
<212> TYPE: DNA
<213> ORGANISM: Artificial Sequence
<220> FEATURE:
<223> OTHER INFORMATION: mCherry-fwd

<400> SEQUENCE: 30
tcaccaccat cattaggatg gtggtgatga taatggttag caaaggtgaa gagga 55

<210> SEQ ID NO 31
<211> LENGTH: 45
<212> TYPE: DNA
<213> ORGANISM: Artificial Sequence
<220> FEATURE:
<223> OTHER INFORMATION: mCherry-rev

<400> SEQUENCE: 31
ggtgctcgag tgcggccgca agctttcatt tatacagttc atcca            45

<210> SEQ ID NO 32
<211> LENGTH: 49
<212> TYPE: DNA
<213> ORGANISM: Artificial Sequence
<220> FEATURE:
<223> OTHER INFORMATION: BRCA-BRCT-fwd

<400> SEQUENCE: 32
actttaagaa ggagatatac atatggtcaa caaaagaatg tccatggtg        49

<210> SEQ ID NO 33
<211> LENGTH: 55
<212> TYPE: DNA
<213> ORGANISM: Artificial Sequence
<220> FEATURE:
<223> OTHER INFORMATION: BRCA-BRCT-rev-1

<400> SEQUENCE: 33
caccatccta atgatggtgg tgatgatgac tagtggggat ctggggtatc aggta 55

<210> SEQ ID NO 34
<211> LENGTH: 54
<212> TYPE: DNA
<213> ORGANISM: Artificial Sequence
<220> FEATURE:
<223> OTHER INFORMATION: BRCA-BRCT-rev-2

<400> SEQUENCE: 34
caccatccta atgatggtgg tgatgatgac tagtcacagg tgcctcacac atct    54

<210> SEQ ID NO 35
<211> LENGTH: 58
<212> TYPE: DNA
<213> ORGANISM: Artificial Sequence
<220> FEATURE:
<223> OTHER INFORMATION: BRCA1-BRCT-STOP-rev

<400> SEQUENCE: 35
caccatccta atgatggtgg tgatgatgac tagtttaggg gatctggggt atcaggta    58

<210> SEQ ID NO 36
<211> LENGTH: 40
<212> TYPE: DNA
<213> ORGANISM: Artificial Sequence
<220> FEATURE:
<223> OTHER INFORMATION: PARP1-BRCT-fwd

<400> SEQUENCE: 36
actttaagaa ggagatatac atatggtgaa ctcctctgct    40

<210> SEQ ID NO 37
<211> LENGTH: 53
<212> TYPE: DNA
<213> ORGANISM: Artificial Sequence
<220> FEATURE:
<223> OTHER INFORMATION: PARP1-BRCT-rev

<400> SEQUENCE: 37
caccatccta atgatggtgg tgatgatgac tagttggggc cacaacttca aca    53

<210> SEQ ID NO 38
<211> LENGTH: 27
<212> TYPE: DNA
<213> ORGANISM: Artificial Sequence
<220> FEATURE:
<223> OTHER INFORMATION: E6-fwd

<400> SEQUENCE: 38
actttaagaa ggagatatac atatggc    27

<210> SEQ ID NO 39
<211> LENGTH: 28
<212> TYPE: DNA
<213> ORGANISM: Artificial Sequence
<220> FEATURE:
<223> OTHER INFORMATION: P19-fwd

<400> SEQUENCE: 39
actttaagaa ggagatatac atatgctg    28

<210> SEQ ID NO 40
<211> LENGTH: 23
<212> TYPE: DNA
<213> ORGANISM: Artificial Sequence
<220> FEATURE:
<223> OTHER INFORMATION: coupling cassette-rev

<400> SEQUENCE: 40
caccatccta atgatggtgg tga    23

<210> SEQ ID NO 41
<211> LENGTH: 32
<212> TYPE: DNA
<213> ORGANISM: Artificial Sequence
<220> FEATURE:
<223> OTHER INFORMATION: NusA-fwd

<400> SEQUENCE: 41
cgacatatga acaaagaaat tttggctgta gt                                32

<210> SEQ ID NO 42
<211> LENGTH: 46
<212> TYPE: DNA
<213> ORGANISM: Artificial Sequence
<220> FEATURE:
<223> OTHER INFORMATION: NusA-rev

<400> SEQUENCE: 42
atacatatgg ctaccagagc cgctacccgc ttcgtcaccg aaccag                 46

<210> SEQ ID NO 43
<211> LENGTH: 27
<212> TYPE: DNA
<213> ORGANISM: Artificial Sequence
<220> FEATURE:
<223> OTHER INFORMATION: SUMO-fwd

<400> SEQUENCE: 43
gaccatatgt cggactcaga agtcaat                                      27

<210> SEQ ID NO 44
<211> LENGTH: 47
<212> TYPE: DNA
<213> ORGANISM: Artificial Sequence
<220> FEATURE:
<223> OTHER INFORMATION: SUMO-rev

<400> SEQUENCE: 44
atccatatgg ctaccagagc cgctaccacc accaatctgt tctctgt                47

<210> SEQ ID NO 45
<211> LENGTH: 29
<212> TYPE: DNA
<213> ORGANISM: Artificial Sequence
<220> FEATURE:
<223> OTHER INFORMATION: Mut-PARP1-BRCT-fwd

<400> SEQUENCE: 45
gagatataca tatggtgaac tcctctgct                                    29

<210> SEQ ID NO 46
<211> LENGTH: 49
<212> TYPE: DNA
<213> ORGANISM: Artificial Sequence
<220> FEATURE:
<223> OTHER INFORMATION: Mutagenesis-fwd

<400> SEQUENCE: 46
cccctctaga ataattttg tttaacttta agaaggagat atacatatg              49

<210> SEQ ID NO 47
<211> LENGTH: 28
<212> TYPE: DNA
<213> ORGANISM: Artificial Sequence
<220> FEATURE:
<223> OTHER INFORMATION: Mutagenesis-rev

<400> SEQUENCE: 47
cctaatgatg gtggtgatga tgactagt                                     28

```
<210> SEQ ID NO 48
<211> LENGTH: 59
<212> TYPE: DNA
<213> ORGANISM: Artificial Sequence
<220> FEATURE:
<223> OTHER INFORMATION: Library-seq-fwd

<400> SEQUENCE: 48
tcgtcggcag cgtcagatgt gtataagaga cagaacttta agaaggagat atacatatg      59

<210> SEQ ID NO 49
<211> LENGTH: 52
<212> TYPE: DNA
<213> ORGANISM: Artificial Sequence
<220> FEATURE:
<223> OTHER INFORMATION: PARP1-BRCT-int-rev

<400> SEQUENCE: 49
gtctcgtggg ctcggagatg tgtataagag acagtgaagg ctcttggtgg ag             52

<210> SEQ ID NO 50
<211> LENGTH: 53
<212> TYPE: DNA
<213> ORGANISM: Artificial Sequence
<220> FEATURE:
<223> OTHER INFORMATION: PARP1-BRCT-int-fwd

<400> SEQUENCE: 50
tcgtcggcag cgtcagatgt gtataagaga cagaacaagg atgaagtgaa ggc            53

<210> SEQ ID NO 51
<211> LENGTH: 56
<212> TYPE: DNA
<213> ORGANISM: Artificial Sequence
<220> FEATURE:
<223> OTHER INFORMATION: Library-seq-rev

<400> SEQUENCE: 51
gtctcgtggg ctcggagatg tgtataagag acagatgatg gtggtgatga tgacta         56
```